United States Patent
Wang et al.

(10) Patent No.: US 9,476,067 B2
(45) Date of Patent: Oct. 25, 2016

(54) SHUTTLE VECTOR CAPABLE OF TRANSFORMING MULTIPLE GENERA OF CYANOBACTERIA

(71) Applicant: Algenol Biofuels Inc., Fort Myers, FL (US)

(72) Inventors: Kui Wang, Fort Myers, FL (US); Tuo Shi, San Diego, CA (US)

(73) Assignee: Algenol Biotech LLC, Fort Myers, FL (US)

( * ) Notice: Subject to any disclaimer, the term of this patent is extended or adjusted under 35 U.S.C. 154(b) by 0 days.

(21) Appl. No.: 14/737,911

(22) Filed: Jun. 12, 2015

(65) Prior Publication Data

US 2015/0322442 A1   Nov. 12, 2015

Related U.S. Application Data

(63) Continuation of application No. PCT/US2013/077359, filed on Dec. 22, 2013.

(60) Provisional application No. 61/835,007, filed on Jun. 14, 2013, provisional application No. 61/740,709, filed on Dec. 21, 2012.

(51) Int. Cl.
| | |
|---|---|
| *C12P 21/02* | (2006.01) |
| *C12N 15/70* | (2006.01) |
| *C12P 7/06* | (2006.01) |
| *C07K 14/195* | (2006.01) |
| *C12N 15/74* | (2006.01) |

(52) U.S. Cl.
CPC ............. *C12P 7/06* (2013.01); *C07K 14/195* (2013.01); *C12N 15/70* (2013.01); *C12N 15/74* (2013.01); *Y02E 50/17* (2013.01)

(58) Field of Classification Search
None
See application file for complete search history.

(56) References Cited

U.S. PATENT DOCUMENTS

| | | |
|---|---|---|
| 6,306,639 B1 | 10/2001 | Woods et al. |
| 6,699,696 B2 | 3/2004 | Woods et al. |
| 7,968,321 B1 | 6/2011 | Green et al. |
| 7,981,647 B2 | 7/2011 | Berry et al. |
| 8,163,516 B2 | 4/2012 | Dehring et al. |
| 8,216,816 B2 | 7/2012 | Green et al. |
| 8,372,613 B2 | 2/2013 | Fu et al. |
| 8,404,466 B2 | 3/2013 | Baier et al. |
| 8,465,954 B2 | 6/2013 | Green et al. |
| 8,846,369 B2 | 9/2014 | Piven et al. |
| 2002/0042111 A1 | 4/2002 | Woods et al. |
| 2009/0155871 A1 | 6/2009 | Fu et al. |
| 2012/0029248 A1 | 2/2012 | Lu et al. |
| 2012/0115187 A1 | 5/2012 | Retallack |
| 2012/0276637 A1 | 11/2012 | Zhou et al. |
| 2014/0178958 A1 | 6/2014 | Piven et al. |
| 2014/0370575 A1 | 12/2014 | Duhring et al. |

FOREIGN PATENT DOCUMENTS

| | | |
|---|---|---|
| EP | 2285948 B1 | 1/2014 |
| WO | WO9839457 | 9/1998 |
| WO | WO/2007/084477 | 7/2007 |
| WO | WO/2009/062190 | 5/2009 |
| WO | WO/2009/078712 | 6/2009 |
| WO | WO/2009/098089 | 8/2009 |
| WO | WO/2009/111513 | 9/2009 |
| WO | WO/2010/044960 | 4/2010 |
| WO | WO/2011/018116 | 2/2011 |
| WO | WO/2014/100798 | 6/2014 |
| WO | WO/2014/100799 | 6/2014 |

OTHER PUBLICATIONS

Elhai et al., "Conjugal Transfer of DNA to Cyanobacteria," Methods in Enzymology. Academic Press. 167: 747-754 (1988).
Huang et al., "Design and characterization of molecular tools for a Synthetic Biology approach towards developing cyanobacterial biotechnology," Nucleic Acids Research 38(8): 2577-2593 (2010).
Koksharova et al., "Genetic tools for cyanobacteria," Applied Microbiology and Biotechnology 58:123-137 (2002).
Kondo et al., "Circadian Rhythms in Prokaryotes: Luciferase as a Reporter of Circadian Gene Expression in Cyanobacteria," Proceedings of the National Academy of Sciences of the United States of America 90:5672-5676 (1993).
Wolk et al., "Construction of Shuttle Vectors Capable of Conjugative Transfer from *Escherichia coli* to Nitrogen-fixing Filamentous Cyanobacteria," Proceedings of the National Academy of Sciences of the United States of America 81:1561-1565 (1984).
Xu et al., "Expression of Genes in Cyanobacteria: Adaptation of Endogenous Plasmids as Platforms for High-level Gene Expression in *Synechococcus* sp. PCC 7002," Photosynthesis Research Protocols. Humana Press. 684:273-293 (2011).
Deng, M-D et al., "Ethanol Synthesis by Genetic Engineering in Cyanobacteria," Applied and Environmental Microbiology, 65: 523-528 (1999).
Qi et al., "Application of the Synechococcus nirA Promoter to Establish an Inducible Expression System for Engineering the Synechocystis Tocopherol Pathway," Appl. Environ. Microbiol. 71:5678-5684 (2005).
Byrne, Patrick, "Differential and Inducible Expression of Yellow Fluorescent Protein in the Marine Cyanobacterium *Synechococcus* sp. PCC 7002," Thesis, Pennsylvania State University, Department of Chemistry and Molecular Biology, Spring, 2010 (35 pages).
International Search Report and Written Opinion for PCT/US2013/077359, dated Apr. 22, 2014 (15 pages).
International Preliminary Report on Patentability for PCT/US2013/077359, dated Jun. 23, 2015 (9 pages).
Vioque, "Transformation of cyanobacteria," Adv. Exp. Med. Biol. 616:12-22 (2007).
Vermaas, "Molecular genetics of the cyanobacterium *Synechocystis* sp. PCC 6803: Principles and possible biotechnology applications," Jour. Appl. Phycology 8:263-273 (1996).

(Continued)

*Primary Examiner* — Jim Ketter
(74) *Attorney, Agent, or Firm* — Lawrence B. Ebert; David J. Lorenz; Suzanne G. Jepson

(57) ABSTRACT

A plasmid vector for the production of compounds in cyanobacteria is described which is capable of being efficiently transformed to and replicating in a broad range of cyanobacterial species.

26 Claims, 22 Drawing Sheets

(56) References Cited

OTHER PUBLICATIONS

Mermet-Bouvier et al., "Transfer and replication of RSF1010-derived plasmids in several cyanobacteria of the genera Synechocystis and Synechococcus," Current Microbiology 27:323-327 (1993).

Schmetterer et al., "Identification of the region of the plasmid pDUI necessary for replication in *Anabaena* sp. strain M-131," Gene, 62:101-109 (1988).

Walton et al., Nucleic Acids Research, 21 (3) GenBank Sequence Accession No. M81382 (1993).

Houmard et al., "Cyanobacterial genetic tools: Current status," Methods in Enzymology 167:808-847 (1988).

Seery et al., "Comparative analysis of the pC194 group of rolling circle plasmids," Plasmid 3:185-196 (1993).

Larkum et al., "Selection, breeding and engineering of microalgae for bioenergy and biofuel production," Trends in Biotechnology 30:198-205 (2012).

Cormack et al., "FACS-optimized mutants of the green fluorescent protein (GFP)," Gene 173:33-38 (1996).

```
   1 AATTAAAAGTATAAAAATTTTAACGGTTCTCGGTTTGATTATTTTCCGAAAAACCGATAAAATAACTCAAAATATTCAACAAGAATAACC  90

91 CAAAAAACTTATTTGAAACATAAGTATAATAAAACGTTATTACATAATTATatgttaaccgaccaatcgaccaaaagtaaagttaataca 180
                 -35                   -10       M  L  T  D  Q  S  T  K  S  K  V  N  T
                                                ORF1→

181 gaattaccagaaaaagctaagaccgttgtaagtaagacacggtcgaacctaacaagcccttctgaagtacggatagacccctctaggtat 270
      E  L  P  E  K  A  K  T  V  V  S  K  T  R  S  N  L  T  S  P  S  E  V  R  I  D  P  S  R  Y 271 taccccgaaggtgttgagatcgtccctgaacttttgatgattccaaccaagggcgctatcgagcgtaatttttgattggtttacttttcgtt 360
      Y  P  E  G  V  E  I  V  P  E  L  L  M  I  P  T  K  G  A  I  E  R  N  F  D  W  F  T  F  V 361 gggagaaaggtgacgagggagaactttgattctattattgatggattttgtggcggcggcttctgggacattgaaacggaaattgatacg 450
      G  R  K  V  T  R  E  N  F  D  S  I  I  D  G  F  C  G  G  G  F  W  D  I  E  T  E  I  D  T 451 actgtttatgacgctaattttttccctttatagggg cggtgaaaagtatgatttatggtggactaattcactaggaattaagatagcatct 540
      T  V  Y  D  A  N  F  S  L  Y  R  G  G  E  K  Y  D  L  W  W  T  N  S  L  G  I  K  I  A  S 541 aggaaaaatgaagaattagatattgagggaaaattaagctatgaaagctatgatttaatcattacttttagtggtagcactttacaacaa 630
      R  K  N  E  E  L  D  I  E  G  K  L  S  Y  E  S  Y  D  L  I  I  T  F  S  G  S  T  L  Q  Q 631 ctttatggatttaataacctttttgagtcaatgtgcgttggtatatcgtgcatatcagttagggttatatttaactagaatagattttgcc 720
      L  Y  G  F  N  N  L  L  S  Q  C  A  L  V  Y  R  A  Y  Q  L  G  L  Y  L  T  R  I  D  F  A 721 gttacagattattccaagaccttgaatgtatttgatgtcaaactagcattattaaaaggtaattttagaggatttaagagtaaaggtact 810
      V  T  D  Y  S  K  T  L  N  V  F  D  V  K  L  A  L  L  K  G  N  F  R  G  F  K  S  K  G  T 811 aatgaaagtggtacacgaaagattgatgggataactaactattgtggtagtcgtgaatctgagtcaatggtaagaatatatgattgtttt 900
      N  E  S  G  T  R  K  I  D  G  I  T  N  Y  C  G  S  R  E  S  E  S  M  V  R  I  Y  D  C  F 901 aaaaaacatggaataatagccactagattagagaatgaattgaagggagataaagcgaaaaagataggtaatgaactgtgtaaactttat 990
      K  K  H  G  I  I  A  T  R  L  E  N  E  L  K  G  D  K  A  K  K  I  G  N  E  L  C  K  L  Y 991 cggagttttgaagaaaaagtgcacatgtgcaatgaagactcaacgcatggatgcaataaaactaagtcaaaaatcagaaaaactaaagca 1080
      R  S  F  E  E  K  V  H  M  C  N  E  D  S  T  H  G  C  N  K  T  K  S  K  I  R  K  T  K  A 1081 catcataatcaggtattagcaagatatttgatagtgtaattacttcaagtattgatttttattgataggagtaaaaagtggaaaaatgga 1170
      H  H  N  Q  V  L  A  R  Y  F  D  S  V  I  T  S  S  I  D  F  I  D  R  S  K  K  W  K  N  G 1171 agtttaaaacactgtaaaagattatcatggtgggaaaagttcaggga aaaattatcatctagtttgataaaattaagctcacaaatcct 1260
      S  L  K  H  C  K  R  L  S  W  W  E  K  F  R  E  K  L  S  S  S  L  M  K  I  K  L  T  N  P 1261 tttaaaaagcctagtttagctgataatgctaaatggttaatcagacaagttaagggaacaattagtaagttaaaaaatggattatgtgat 1350
      F  K  K  P  S  L  A  D  N  A  K  W  L  I  R  Q  V  K  G  T  I  S  K  L  K  N  G  L  C  D 1351 tttgactttaatcaattaatggaattattaaagcaattagatgatgatagacccaaacctaaaggtatccaagaagaaaaggaattagcg 1440
      F  D  F  N  Q  L  M  E  L  L  K  Q  L  D  D  D  R  P  K  P  K  G  I  Q  E  E  K  E  L  A
```

FIG. 3A(1)

```
1441 attaagatattaaagaaacaaggaattaacgctttatttacccaagatgaactccaagaatttaaagaaagatttggaatagaatttgat 1530
      I  K  I  L  K  K  Q  G  I  N  A  L  F  T  Q  D  E  L  Q  E  F  K  E  R  F  G  I  E  F  D 1531 aaaacaaatcctcatggaactatctttgagtatgataattattttggtgataagttcagtaatgatttaaccattggtgatagagtaaaa 1620
      K  T  N  P  H  G  T  I  F  E  Y  D  N  Y  F  G  D  K  F  S  N  D  L  T  I  G  D  R  V  K 1621 ttcattttagggggtatttggtttaatggaactattaagaagataaataaaacaggtttagaaacagaaaattatgacgttaactttgat 1710
      F  I  L  G  G  I  W  F  N  G  T  I  K  K  I  N  K  T  G  L  E  T  E  N  Y  D  V  N  P  D 1711 gatggcgggttttatagtggtataattccagataatatatttaggcttaagagtagttaaAAAGCGAAACGTGTTTCGTATTTGTATTTA 1800
      D  G  G  F  Y  S  G  I  I  P  D  N  I  F  R  L  K  S  S  *  --------->   <----------  ------
                                                                      IR1              IR1 IR2

1801 ATAAGTCTAAAAAAGTCTGATTTAAGTTGTTTAATTAGGTCATCACGCTGGCGTAGCTAAACCTTAGATGGAATAAGGTCAAAAACATAC 1890
     ---->     ---------->                                                         <----------
            IR3                                                                        IR3

1891 TACAAGACCTGATCGCAATTAGTAAATAAATGATTTATTCTTAATAAGAAATAGCCAAATTAGCCCTAGCCCTCTTAACCACTGAAATAT 1980
     -      <----------
              IR2

1981 TAATTAGTTTGTGAGAAAGTTTCGTGTCAAGAGTGTAACGGAATAAAGTTTTTTCGGTTATTAACTAAGATATGAACTTATTATTATTGT 2070
     ----------------->   ---------------->              -35                  -10
           IR4                    IR5

2071 TCCGAAAAAAGTTTATGCAGTCTCTTGACATGAAatgaaacaaacgtataatcacattacaagggctagggcgatgtttaagcgaagtgat 2160
     <-----------------<---------------          M  N  K  R  I  I  T  L  Q  G  L  G  R  C  L  S  E  V  I
              IR5              IR4  ORF2→

2161 aaaaccaaaccttaaagattcaatttgaGGGTGTTCAGGAGTGATTTAAGACTTGTAAATTAATTTCAACCCTATGAGGATTGAACTAGA 2250
      K  P  N  L  K  D  S  I  *        ---------->  <------------------>            <----------
                                          IR1          IR1           IR2                 IR2

2251 CCCATAAACCCCAAATAAGAGCAAAATACCATCAGCACAGCTTCCGTACCTACCTCGCTTATAAACCGCTTTTTCTTTACTTTTTCATCG 2340

2341 GCTTAACATTCTTACGACTCCTATAGGAGTTGTAGAGTTCTTAAACAATTACTAAACAATTAATATTTTTCGTTAAAGTCGATGGTTAT 2430
              ---------><----------
              IR3           IR3

2431 GGTTGTGTCAGAATGCACATTAGTGTTGGGTTAGTGTGGCGGACATCATTATGATCTCCACTAAATAC 2498
```

FIG. 3A(2)

ABICyano1::pSA131          ABICyano1::pCK5
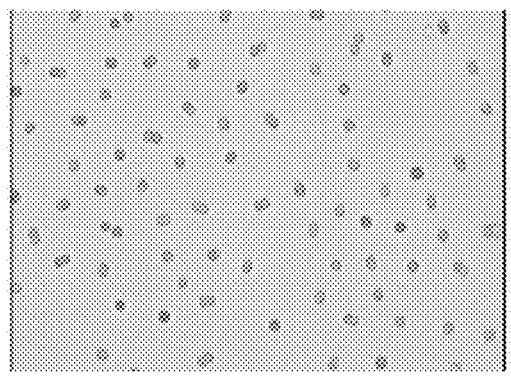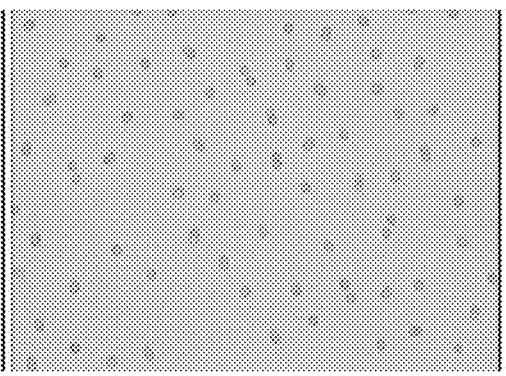
FIG. 18 ic Acids Research 38:2577-2593 (2010).

SEQUENCE LISTING

<160> NUMBER OF SEQ ID NOS: 87

<210> SEQ ID NO 1
<211> LENGTH: 2498
<212> TYPE: DNA
<213> ORGANISM: Cyanobacterium sp.

<400> SEQUENCE: 1

| | | | | | |
|---|---|---|---|---|---|
| aattaaaagt | ataaaaattt | taacggttct | cggtttgatt | attttccgaa | aaaccgataa | 60 |
| aataactcaa | aatattcaac | aagaataacc | caaaaaactt | atttgaaaca | taagtataat | 120 |
| aaaaggttat | tacataatta | tatgttaacc | gaccaatcga | ccaaaagtaa | agttaataca | 180 |
| gaattaccag | aaaaagctaa | gaccgttgta | agtaagacac | ggtcgaacct | aacaagccct | 240 |
| tctgaagtac | ggatagaccc | ctctaggtat | taccccgaag | gtgttgagat | cgtccctgaa | 300 |
| cttttgatga | ttccaaccaa | gggcgctatc | gagcgtaatt | ttgattggtt | tactttcgtt | 360 |
| gggagaaagg | tgacgaggga | gaactttgat | tctattattg | atggattttg | tggcggcggc | 420 |
| ttctgggaca | ttgaaacgga | aattgatacg | actgtttatg | acgctaattt | ttcccttat | 480 |
| aggggcggtg | aaaagtatga | tttatggtgg | actaattcac | taggaattaa | gatagcatct | 540 |
| aggaaaaatg | aagaattaga | tattgaggga | aaattaagct | atgaaagcta | tgatttaatc | 600 |
| attactttta | gtggtagcac | tttacaacaa | ctttatggat | ttaataacct | tttgagtcaa | 660 |
| tgtgcgttgg | tatatcgtgc | atatcagtta | gggttatatt | taactagaat | agattttgcc | 720 |
| gttacagatt | attccaagac | cttgaatgta | tttgatgtca | aactagcatt | attaaaaggt | 780 |
| aattttagag | gatttaagag | taaaggtact | aatgaaagtg | gtacacgaaa | gattgatggg | 840 |
| ataactaact | attgtggtag | tcgtgaatct | gagtcaatgg | taagaatata | tgattgtttt | 900 |
| aaaaaacatg | gaataatagc | cactagatta | gagaatgaat | tgaagggaga | taaagcgaaa | 960 |
| aagataggta | atgaactgtg | taaactttat | cggagttttg | aagaaaaagt | gcatatgtgc | 1020 |
| aatgaagact | caacgcatgg | atgcaataaa | actaagtcaa | aaatcagaaa | aactaaagca | 1080 |
| catcataatc | aggtattagc | aagatatttt | gatagtgtaa | ttacttcaag | tattgatttt | 1140 |
| attgatagga | gtaaaaagtg | gaaaaatgga | agtttaaaac | actgtaaaag | attatcatgg | 1200 |
| tgggaaaagt | tcagggaaaa | attatcatct | agtttgatga | aaattaagct | cacaaatcct | 1260 |
| tttaaaaagc | ctagtttagc | tgataatgct | aaatggttaa | tcagacaagt | taagggaaca | 1320 |
| attagtaagt | taaaaaatgg | attatgtgat | tttgacttta | atcaattaat | ggaattatta | 1380 |
| aagcaattag | atgatgatag | acccaaacct | aaaggtatcc | aagaagaaaa | ggaattagcg | 1440 |
| attaagatat | taagaaaaca | aggaattaac | gctttattta | cccaagatga | actccaagaa | 1500 |
| tttaaagaaa | gatttggaat | agaatttgat | aaaacaaatc | ctcatggaac | tatctttgag | 1560 |
| tatgataatt | attttggtga | taagttcagt | aatgatttaa | ccattggtga | tagagtaaaa | 1620 |
| ttcatttag | ggggtatttg | gtttaatgga | actattaaga | agataaataa | aacaggttta | 1680 |
| gaaacagaaa | attatgacgt | taactttgat | gatggcgggt | tttatagtgg | tataattcca | 1740 |
| gataatatat | ttaggcttaa | gagtagttaa | aaagcgaaac | gtgtttcgta | tttgtattta | 1800 |
| ataagtctaa | aaaagtctga | tttaagttgt | ttaattaggt | catcacgctg | gcgtagctaa | 1860 |
| accttagatg | gaataaggtc | aaaaacatac | tacaagacct | gatcgcaatt | agtaaataaa | 1920 |
| tgatttattc | ttaataagaa | atagccaaat | tagccctagc | cctcttaacc | actgaaatat | 1980 |
| taattagttt | gtgagaaagt | ttcgtgtcaa | gagtgtaacg | gaataaagtt | ttttcggtta | 2040 |
| ttaactaaga | tatgaactta | ttattattgt | tccgaaaaaa | gtttatgcag | tctcttgaca | 2100 |

```
tgaaatgaac aaacgtataa tcacattaca agggctaggg cgatgtttaa gcgaagtgat      2160
aaaaccaaac cttaaagatt caatttgagg gtgttcagga gtgatttaag acttgtaaat      2220
taatttcaac cctatgagga ttgaactaga cccataaacc ccaaataaga gcaaatacc       2280 atcagcacag cttccgtacc tacctcgctt ataaaccgct ttttctttac tttttcatcg      2340
gcttaacatt cttacgactc ctataggagt tgtagagttc ttaaacaatt actaaacaat      2400 taatatttt tcgttaaagt cgatggttat ggttgtgtca gaatgcacat tagtgttggg       2460
ttagtgtggc ggacatcatt atgatctcca ctaaatac                              2498

<210> SEQ ID NO 2
<211> LENGTH: 1629
<212> TYPE: DNA
<213> ORGANISM: Cyanobacterium sp.

<400> SEQUENCE: 2
atgttaaccg accaatcgac caaaagtaaa gttaatacag aattaccaga aaaagctaag        60
accgttgtaa gtaagacacg gtcgaaccta acaagccctt ctgaagtacg gatagacccc      120
tctaggtatt accccgaagg tgttgagatc gtccctgaac ttttgatgat tccaaccaag      180
ggcgctatcg agcgtaattt tgattggttt actttcgttg ggagaaaggt gacgagggag      240
aactttgatt ctattattga tggattttgt ggcggcggct tctgggacat tgaaacggaa      300
attgatacga ctgtttatga cgctaatttt tcccttata ggggcggtga aaagtatgat       360
ttatggtgga ctaattcact aggaattaag atagcatcta ggaaaaatga agaattagat      420
attgagggaa aattaagcta tgaaagctat gatttaatca ttacttttag tggtagcact      480
ttacaacaac tttatggatt taataacctt ttgagtcaat gtgcgttggt atatcgtgca      540
tatcagttag ggttatattt aactagaata gattttgccg ttacagatta ttccaagacc      600
ttgaatgtat ttgatgtcaa actagcatta ttaaaaggta attttagagg attttaagagt     660 aaaggtacta atgaaagtgg tacacgaaag attgatggga taactaacta ttgtggtagt     720
cgtgaatctg agtcaatggt aagaatatat gattgtttta aaaacatgg aataatagcc      780 actagattag agaatgaatt gaagggagat aaagcgaaaa agataggtaa tgaactgtgt     840
aaactttatc ggagttttga agaaaaagtg cacatgtgca atgaagactc aacgcatgga      900
tgcaataaaa ctaagtcaaa aatcagaaaa actaaagcac atcataatca ggtattagca     960
agatattttg atagtgtaat tacttcaagt attgattttt ttgataggag taaaaagtgg    1020
aaaaatggaa gtttaaaaca ctgtaaaaga ttatcatggt gggaaaagtt cagggaaaaa    1080
ttatcatcta gtttgatgaa aattaagctc acaaatcctt ttaaaagcc tagtttagct     1140 gataatgcta aatggttaat cagacaagtt aagggaacaa ttagtaagtt aaaaaatgga    1200
ttatgtgatt ttgactttaa tcaattaatg gaattattaa agcaattaga tgatgataga    1260
cccaaaccta aagtatcca agaagaaaag gaattagcga ttaagatatt aaagaaacaa     1320
ggaattaacg ctttatttac ccaagatgaa ctccaagaat ttaaagaaag atttggaata    1380
gaatttgata aaacaaatcc tcatggaact atctttgagt atgataatta ttttggtgat    1440
aagttcagta atgatttaac cattggtgat agagtaaaat tcattttagg gggtatttgg    1500
tttaatggaa ctattaagaa gataaatatat aacaggtttag aaacagaaaa ttatgacgtt    1560
aactttgatg atggcgggtt ttatagtggt ataattccag ataatatatt taggcttaag    1620
agtagttaa                                                            1629
```

<210> SEQ ID NO 3
<211> LENGTH: 542
<212> TYPE: PRT
<213> ORGANISM: Cyanobacterium sp.

<400> SEQUENCE: 3

```
Met Leu Thr Asp Gln Ser Thr Lys Ser Lys Val Asn Thr Glu Leu Pro
1               5                   10                  15

Glu Lys Ala Lys Thr Val Val Ser Lys Thr Arg Ser Asn Leu Thr Ser
            20                  25                  30

Pro Ser Glu Val Arg Ile Asp Pro Ser Arg Tyr Tyr Pro Glu Gly Val
        35                  40                  45

Glu Ile Val Pro Glu Leu Leu Met Ile Pro Thr Lys Gly Ala Ile Glu
    50                  55                  60

Arg Asn Phe Asp Trp Phe Thr Phe Val Gly Arg Lys Val Thr Arg Glu
65                  70                  75                  80

Asn Phe Asp Ser Ile Ile Asp Gly Phe Cys Gly Gly Phe Trp Asp
                85                  90                  95

Ile Glu Thr Glu Ile Asp Thr Thr Val Tyr Asp Ala Asn Phe Ser Leu
            100                 105                 110

Tyr Arg Gly Gly Glu Lys Tyr Asp Leu Trp Trp Thr Asn Ser Leu Gly
        115                 120                 125

Ile Lys Ile Ala Ser Arg Lys Asn Glu Glu Leu Asp Ile Glu Gly Lys
    130                 135                 140

Leu Ser Tyr Glu Ser Tyr Asp Leu Ile Ile Thr Phe Ser Gly Ser Thr
145                 150                 155                 160

Leu Gln Gln Leu Tyr Gly Phe Asn Asn Leu Leu Ser Gln Cys Ala Leu
                165                 170                 175

Val Tyr Arg Ala Tyr Gln Leu Gly Leu Tyr Leu Thr Arg Ile Asp Phe
            180                 185                 190

Ala Val Thr Asp Tyr Ser Lys Thr Leu Asn Val Phe Asp Val Lys Leu
        195                 200                 205

Ala Leu Leu Lys Gly Asn Phe Arg Gly Phe Lys Ser Lys Gly Thr Asn
    210                 215                 220

Glu Ser Gly Thr Arg Lys Ile Asp Gly Ile Thr Asn Tyr Cys Gly Ser
225                 230                 235                 240

Arg Glu Ser Glu Ser Met Val Arg Ile Tyr Asp Cys Phe Lys Lys His
                245                 250                 255

Gly Ile Ile Ala Thr Arg Leu Glu Asn Glu Leu Lys Gly Asp Lys Ala
            260                 265                 270

Lys Lys Ile Gly Asn Glu Leu Cys Lys Leu Tyr Arg Ser Phe Glu Glu
        275                 280                 285

Lys Val His Met Cys Asn Glu Asp Ser Thr His Gly Cys Asn Lys Thr
    290                 295                 300

Lys Ser Lys Ile Arg Lys Thr Lys Ala His His Asn Gln Val Leu Ala
305                 310                 315                 320

Arg Tyr Phe Asp Ser Val Ile Thr Ser Ser Ile Asp Phe Ile Asp Arg
                325                 330                 335

Ser Lys Lys Trp Lys Asn Gly Ser Leu Lys His Cys Lys Arg Leu Ser
            340                 345                 350

Trp Trp Glu Lys Phe Arg Glu Lys Leu Ser Ser Ser Leu Met Lys Ile
        355                 360                 365

Lys Leu Thr Asn Pro Phe Lys Lys Pro Ser Leu Ala Asp Asn Ala Lys
    370                 375                 380
```

```
Trp Leu Ile Arg Gln Val Lys Gly Thr Ile Ser Lys Leu Lys Asn Gly
385                 390                 395                 400

Leu Cys Asp Phe Asp Phe Asn Gln Leu Met Glu Leu Leu Lys Gln Leu
            405                 410                 415

Asp Asp Asp Arg Pro Lys Pro Lys Gly Ile Gln Glu Glu Lys Glu Leu
            420                 425                 430

Ala Ile Lys Ile Leu Lys Lys Gln Gly Ile Asn Ala Leu Phe Thr Gln
            435                 440                 445

Asp Glu Leu Gln Glu Phe Lys Glu Arg Phe Gly Ile Glu Phe Asp Lys
            450                 455                 460

Thr Asn Pro His Gly Thr Ile Phe Glu Tyr Asp Asn Tyr Phe Gly Asp
465                 470                 475                 480

Lys Phe Ser Asn Asp Leu Thr Ile Gly Asp Arg Val Lys Phe Ile Leu
            485                 490                 495

Gly Gly Ile Trp Phe Asn Gly Thr Ile Lys Lys Ile Asn Lys Thr Gly
            500                 505                 510

Leu Glu Thr Glu Asn Tyr Asp Val Asn Phe Asp Asp Gly Gly Phe Tyr
            515                 520                 525

Ser Gly Ile Ile Pro Asp Asn Ile Phe Arg Leu Lys Ser Ser
            530                 535                 540

<210> SEQ ID NO 4
<211> LENGTH: 10
<212> TYPE: PRT
<213> ORGANISM: Cyanobacterium sp. ABICyano2

<400> SEQUENCE: 4

Glu Thr Glu Asn Tyr Asp Val Asn Phe Asp
1               5                   10

<210> SEQ ID NO 5
<211> LENGTH: 11
<212> TYPE: PRT
<213> ORGANISM: Artificial sequence
<220> FEATURE:
<223> OTHER INFORMATION: consensus sequence
<220> FEATURE:
<221> NAME/KEY: MISC_FEATURE
<222> LOCATION: (2)..(3)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa can be any naturally occurring amino acid
<220> FEATURE:
<221> NAME/KEY: MISC_FEATURE
<222> LOCATION: (9)..(10)
<223> OTHER INFORMATION: Xaa can be any naturally occurring amino acid

<400> SEQUENCE: 5

Glu Xaa Xaa Lys Tyr Xaa Val Lys Xaa Xaa Asp
1               5                   10

<210> SEQ ID NO 6
<211> LENGTH: 4122
<212> TYPE: DNA
<213> ORGANISM: Artificial Sequence
<220> FEATURE:
<223> OTHER INFORMATION: Synthetic plasmid vector construct

<400> SEQUENCE: 6
aattaaaagt ataaaaattt taacggttct cggtttgatt attttccgaa aaaccgataa      60
```

```
aataactcaa aatattcaac aagaataacc caaaaaactt atttgaaaca taagtataat      120
aaaaggttat tacataatta tatgttaacc gaccaatcga ccaaaagtaa agttaataca      180
gaattaccag aaaaagctaa gaccgttgta agtaagacac ggtcgaacct aacaagccct      240
tctgaagtac ggatagaccc ctctaggtat tacccgaag gtgttgagat cgtccctgaa       300
cttttgatga ttccaaccaa gggcgctatc gagcgtaatt ttgattggtt tactttcgtt     360
gggagaaagg tgacgaggga gaactttgat tctattattg atggattttg tggcggcggc     420
ttctgggaca ttgaaacgga aattgatacg actgtttatg acgctaattt ttccctttat     480 agggcggtg aaaagtatga tttatggtgg actaattcac taggaattaa gatagcatct       540
aggaaaaatg aagaattaga tattgaggga aaattaagct atgaaagcta tgatttaatc     600 attacttta gtggtagcac tttacaacaa ctttatggat ttaataaccct tttgagtcaa      660 tgtgcgttgg tatatcgtgc atatcagtta gggttatatt taactagaat agattttgcc     720
gttacagatt attccaagac cttgaatgta tttgatgtca aactagcatt attaaaaggt     780
aattttagag gatttaagag taaaggtact aatgaaagtg gtacacgaaa gattgatggg    840
ataactaact attgtggtag tcgtgaatct gagtcaatgg taagaatata tgattgtttt     900 aaaaacatg gaataatagc cactagatta gagaatgaat tgaagggaga taaagcgaaa       960
aagataggta atgaactgtg taaactttat cggagttttg aagaaaaagt gcatatgtgc     1020
aatgaagact caacgcatgg atgcaataaa actaagtcaa aaatcagaaa aactaaagca     1080
catcataatc aggtattagc aagatatttt gatagtgtaa ttacttcaag tattgatttt    1140
attgatagga gtaaaaagtg gaaaaatgga agtttaaaac actgtaaaag attatcatgg     1200
tgggaaaagt tcagggaaaa attatcatct agtttgatga aaattaagct cacaaatcct     1260
tttaaaaagc ctagtttagc tgataatgct aaatggttaa tcagacaagt taagggaaca     1320
attagtaagt taaaaaatgg attatgtgat tttgactta atcaattaat ggaattatta      1380
aagcaattag atgatgatag acccaaacct aaaggtatcc aagaagaaaa ggaattagcg     1440
attaagatat taaagaaaca aggaattaac gctttattta cccaagatga actccaagaa    1500
tttaaagaaa gatttggaat agaatttgat aaaacaaatc ctcatggaac tatctttgag    1560
tatgataatt attttggtga taagttcagt aatgatttaa ccattggtga tagagtaaaa    1620 ttcatttag ggggtatttg gtttaatgga actattaaga agataaataa aacaggttta       1680
gaaacagaaa attatgacgt taactttgat gatggcgggt tttatagtgg tataattcca     1740
gataatatat ttaggcttaa gagtagttaa aaagcgaaac gtgtttcgta tttgtatta      1800 ataagtctaa aaaagtctga tttaagttgt ttaattaggt catcacgctg gcgtagctaa    1860
accttagatg gaataaggtc aaaaacatac tacaagacct gatcgcaatt agtaaataaa    1920
tgatttattc ttaataagaa atagccaaat tagcccttct agacctagga cagctgtctc     1980
ttatacacat ctcaaatgca ttgatcagca gttcaacctg ttgatagtac gtactaagct    2040
ctcatgtttc acgtactaag ctctcatgtt aacgtacta agctctcatg tttaacgaac     2100
taaaccctca tggctaacgt actaagctct catggctaac gtactaagct ctcatgtttc    2160
acgtactaag ctctcatgtt tgaacaataa aattaatata aatcagcaac ttaaatagcc    2220
tctaaggttt taagttttat aagaaaaaaa agaatatata aggcttttaa agcttttaag    2280
gtttaacggt tgtggacaac aagccaggga tgtaacgcac tgagaagccc ttagagcctc     2340
tcaaagcaat tttgagtgac acaggaacac ttcgaaccgt acgggtcgac gaattcggat    2400
ccgagctcac tagtcatatg agatctctgc agactgtgca cgatatccaa ttgcatggaa    2460
```

| | | | |
|---|---|---|---|
| aaaacgacaa | ttacaagaaa gtaaaactta tgtcatctat atgcttcgtg tatattaact | 2520 |
| tcctgttaca | gagctttaca aaactctcat taatccttta gactaagttt agtcagttcc | 2580 |
| aatctgaaca | tcgacaaata cataaggaat tataaccaag catgcaacgt gaagctgtta | 2640 |
| ttgcagaagt | ttctactcaa ttatctgaag ttgtaggtgt tatcgaaaga catttagaac | 2700 |
| ccaccttgtt | agcagtacat ttgtacggaa gtgctgtaga tggaggtctc aaaccccatt | 2760 |
| ctgacattga | tttattggtt acagtaactg ttcgtctcga cgaaaccacc cgccgtgctt | 2820 |
| tgattaacga | tttattagaa acaagtgcct ctccaggtga atccgaaatc ttgagagctg | 2880 |
| ttgaggtaac | aatcgttgta catgacgata ttatcccttg cgttatccc gctaagcgtg | 2940 |
| aattacaatt | tggagaatgg caacgtaatg atattttagc aggtatcttt gaacctgcaa | 3000 |
| ctattgatat | tgacttagct attttgttaa ccaaagctag agaacattct gttgcattag | 3060 |
| taggacccgc | tgccgaagag ttgtttgatc ccgtacctga gcaagattta tttgaagctc | 3120 |
| tcaacgaaac | tttaacctta tggaactccc ctcccgattg ggcaggtgat gaacgtaacg | 3180 |
| ttgtattaac | cttgtctcgc atttggtaca gtgctgtaac tggtaaaatt gcacctaaag | 3240 |
| acgttgccgc | tgattgggca atggaaagat tacccgccca atatcaaccc gtaattttag | 3300 |
| aagctcgtca | agcctatttg ggtcaagagg aagatagatt agcttctcgt gcagatcaat | 3360 |
| tagaagaatt | tgttcattat gtgaaaggag aaatcacaaa agtagttggg aaataaaagc | 3420 |
| ttccatggca | gcacgcttgg actcctgttg atagatccag taatgacctc agaactccat | 3480 |
| ctggatttgt | tcagaacgct cggttgccgc cgggcgtttt ttattggtga aatccaagc | 3540 |
| actgctagct | tgagatgtgt ataagagaca gctgttctag aagccctctt aaccactgaa | 3600 |
| atattaatta | gtttgtgaga agtttcgtg tcaagagtgt aacggaataa agttttttcg | 3660 |
| gttattaact | aagatatgaa cttattatta ttgttccgaa aaagtttat gcagtctctt | 3720 |
| gacatgaaat | gaacaaacgt ataatcacat tacaagggct agggcgatgt ttaagcgaag | 3780 |
| tgataaaacc | aaaccttaaa gattcaattt gagggtgttc aggagtgatt taagacttgt | 3840 |
| aaattaattt | caaccctatg aggattgaac tagaccccata aaccccaaat aagagcaaaa | 3900 |
| taccatcagc | acagcttccg tacctacctc gcttataaac cgcttttct ttacttttc | 3960 |
| atcggcttaa | cattcttacg actcctatag gagttgtaga gttcttaaac aattactaaa | 4020 |
| caattaatat | ttttcgtta aagtcgatgg ttatggttgt gtcagaatgc acattagtgt | 4080 |
| tgggttagtg | tggcggacat cattatgatc tccactaaat ac | 4122 |

<210> SEQ ID NO 7
<211> LENGTH: 792
<212> TYPE: DNA
<213> ORGANISM: Artificial sequence
<220> FEATURE:
<223> OTHER INFORMATION: Codon optimized version of aadA gene sequence originally from Shigella flexneri

<400> SEQUENCE: 7

| | | | |
|---|---|---|---|
| atgcgtgaag | ctgttattgc agaagtttct actcaattat ctgaagttgt aggtgttatc | 60 |
| gaaagacatt | tagaacccac cttgttagca gtacatttgt acggaagtgc tgtagatgga | 120 |
| ggtctcaaac | cccattctga cattgattta ttggttacag taactgttcg tctcgacgaa | 180 |
| accacccgcc | gtgctttgat taacgattta ttagaaacaa gtgcctctcc aggtgaatcc | 240 |
| gaaatcttga | gagctgttga ggtaacaatc gttgtacatg acgatattat cccttggcgt | 300 |
| tatcccgcta | agcgtgaatt acaatttgga gaatggcaac gtaatgatat tttagcaggt | 360 |

```
atctttgaac ctgcaactat tgatattgac ttagctattt tgttaaccaa agctagagaa     420
cattctgttg cattagtagg acccgctgcc gaagagttgt ttgatcccgt acctgagcaa     480
gatttatttg aagctctcaa cgaaacttta accttatgga actcccctcc cgattgggca     540
ggtgatgaac gtaacgttgt attaaccttg tctcgcattt ggtacagtgc tgtaactggt     600
aaaattgcac ctaaagacgt tgccgctgat tgggcaatgg aaagattacc cgcccaatat     660
caacccgtaa ttttagaagc tcgtcaagcc tatttgggtc aagaggaaga tagattagct     720
tctcgtgcag atcaattaga agaatttgtt cattatgtga aaggagaaat cacaaaagta     780
gttgggaaat aa                                                         792
```

<210> SEQ ID NO 8
<211> LENGTH: 263
<212> TYPE: PRT
<213> ORGANISM: Shigella flexneri

<400> SEQUENCE: 8

```
Met Arg Glu Ala Val Ile Ala Glu Val Ser Thr Gln Leu Ser Glu Val
1               5                   10                  15

Val Gly Val Ile Glu Arg His Leu Glu Pro Thr Leu Leu Ala Val His
            20                  25                  30

Leu Tyr Gly Ser Ala Val Asp Gly Gly Leu Lys Pro His Ser Asp Ile
        35                  40                  45

Asp Leu Leu Val Thr Val Thr Val Arg Leu Asp Glu Thr Thr Arg Arg
    50                  55                  60

Ala Leu Ile Asn Asp Leu Leu Glu Thr Ser Ala Ser Pro Gly Glu Ser
65                  70                  75                  80

Glu Ile Leu Arg Ala Val Glu Val Thr Ile Val Val His Asp Asp Ile
                85                  90                  95

Ile Pro Trp Arg Tyr Pro Ala Lys Arg Glu Leu Gln Phe Gly Glu Trp
            100                 105                 110

Gln Arg Asn Asp Ile Leu Ala Gly Ile Phe Glu Pro Ala Thr Ile Asp
        115                 120                 125

Ile Asp Leu Ala Ile Leu Leu Thr Lys Ala Arg Glu His Ser Val Ala
    130                 135                 140

Leu Val Gly Pro Ala Ala Glu Glu Leu Phe Asp Pro Val Pro Glu Gln
145                 150                 155                 160

Asp Leu Phe Glu Ala Leu Asn Glu Thr Leu Thr Leu Trp Asn Ser Pro
                165                 170                 175

Pro Asp Trp Ala Gly Asp Glu Arg Asn Val Val Leu Thr Leu Ser Arg
            180                 185                 190

Ile Trp Tyr Ser Ala Val Thr Gly Lys Ile Ala Pro Lys Asp Val Ala
        195                 200                 205

Ala Asp Trp Ala Met Glu Arg Leu Pro Ala Gln Tyr Gln Pro Val Ile
    210                 215                 220

Leu Glu Ala Arg Gln Ala Tyr Leu Gly Gln Glu Glu Asp Arg Leu Ala
225                 230                 235                 240

Ser Arg Ala Asp Gln Leu Glu Glu Phe Val His Tyr Val Lys Gly Glu
                245                 250                 255

Ile Thr Lys Val Val Gly Lys
            260
```

<210> SEQ ID NO 9
<211> LENGTH: 168

```
<212> TYPE: DNA
<213> ORGANISM: Synechocystis sp. PCC6803

<400> SEQUENCE: 9
catggaaaaa acgacaatta caagaaagta aaacttatgt catctatatg cttcgtgtat      60
attaacttcc tgttacagag ctttacaaaa ctctcattaa tcctttagac taagtttagt     120
cagttccaat ctgaacatcg acaaatacat aaggaattat aaccaagc                  168

<210> SEQ ID NO 10
<211> LENGTH: 368
<212> TYPE: DNA
<213> ORGANISM: Escherichia coli

<400> SEQUENCE: 10
gatcagcagt tcaacctgtt gatagtacgt actaagctct catgtttcac gtactaagct      60
ctcatgttta acgtactaag ctctcatgtt taacgaacta aaccctcatg ctaacgtac     120 taagctctca tggctaacgt actaagctct catgtttcac gtactaagct ctcatgtttg     180
aacaataaaa ttaatataaa tcagcaactt aaatagcctc taaggtttta agttttataa     240
gaaaaaaaag aatatataag gcttttaaag cttttaaggt ttaacggttg tggacaacaa     300
gccagggatg taacgcactg agaagccctt agagcctctc aaagcaattt tgagtgacac     360
aggaacac                                                              368

<210> SEQ ID NO 11
<211> LENGTH: 5185
<212> TYPE: DNA
<213> ORGANISM: Artificial sequence
<220> FEATURE:
<223> OTHER INFORMATION: Synthetic plasmid vector construct

<400> SEQUENCE: 11
aattaaaagt ataaaatttt taacggttct cggtttgatt attttccgaa aaaccgataa      60 ataactcaa atattcaac aagaataacc caaaaaactt atttgaaaca taagtataat     120
aaaaggttat tacataatta tatgttaacc gaccaatcga ccaaaagtaa agttaataca     180
gaattaccag aaaaagctaa gaccgttgta agtaagacac ggtcgaacct aacaagccct     240
tctgaagtac ggatagaccc ctctaggtat taccccgaag gtgttgagat cgtccctgaa     300
cttttgatga ttccaaccaa gggcgctatc gagcgtaatt ttgattggtt tactttcgtt     360
gggagaaagg tgacgaggga gaactttgat tctattattg atggattttg tggcggcggc     420
ttctgggaca ttgaaacgga aattgatacg actgtttatg acgctaattt ttcccttttat     480 aggggcggtg aaaagtatga tttatggtgg actaattcac taggaattaa gatagcatct     540
aggaaaaatg aagaattaga tattgaggga aaattaagct atgaaagcta tgatttaatc     600 attacttta gtggtagcac tttacaacaa ctttatggat ttaataacct tttgagtcaa     660
tgtgcgttgg tatatcgtgc atatcagtta gggttatatt taactagaat agattttgcc     720
gttacagatt attccaagac cttgaatgta tttgatgtca aactagcatt attaaaaggt     780
aattttagag gatttaagag taaaggtact aatgaaagtg gtacacgaaa gattgatggg     840
ataactaact attgtggtag tcgtgaatct gagtcaatgg taagaatata tgattgtttt     900
aaaaaacatg gaataatagc cactagatta gagaatgaat tgaagggaga taaagcgaaa     960
aagataggta atgaactgtg taaactttat cggagttttg aagaaaaagt gcatatgtgc    1020
aatgaagact caacgcatgg atgcaataaa actaagtcaa aaatcagaaa aactaaagca    1080
```

```
catcataatc aggtattagc aagatatttt gatagtgtaa ttacttcaag tattgatttt    1140
attgatagga gtaaaaagtg gaaaaatgga agtttaaaac actgtaaaag attatcatgg    1200
tgggaaaagt tcagggaaaa attatcatct agtttgatga aaattaagct cacaaatcct    1260
tttaaaaagc ctagtttagc tgataatgct aaatggttaa tcagacaagt taagggaaca    1320
attagtaagt taaaaaatgg attatgtgat tttgacttta atcaattaat ggaattatta    1380
aagcaattag atgatgatag acccaaacct aaaggtatcc aagaagaaaa ggaattagcg    1440
attaagatat taaagaaaca aggaattaac gctttattta cccaagatga actccaagaa    1500
tttaaagaaa gatttggaat agaatttgat aaaacaaatc ctcatggaac tatctttgag    1560
tatgataatt attttggtga taagttcagt aatgatttaa ccattggtga tagagtaaaa    1620
ttcattttag ggggtatttg gtttaatgga actattaaga agataaataa aacaggttta    1680
gaaacagaaa attatgacgt taactttgat gatggcgggt tttatagtgg tataattcca    1740
gataatatat ttaggcttaa gagtagttaa aaagcgaaac gtgtttcgta tttgtattta    1800
ataagtctaa aaaagtctga tttaagttgt ttaattaggt catcacgctg gcgtagctaa    1860
accttagatg gaataaggtc aaaaacatac tacaagacct gatcgcaatt agtaaataaa    1920
tgatttattc ttaataagaa atagccaaat tagcccttct agacctagga cagctgtctc    1980
ttatacacat ctcaaatgca ttgatcagca gttcaacctg ttgatagtac gtactaagct    2040
ctcatgtttc acgtactaag ctctcatgtt taacgtacta agctctcatg tttaacgaac    2100
taaaccctca tggctaacgt actaagctct catggctaac gtactaagct ctcatgtttc    2160
acgtactaag ctctcatgtt tgaacaataa aattaatata aatcagcaac ttaaatagcc    2220
tctaaggttt taagttttat aagaaaaaaa agaatatata aggcttttaa agcttttaag    2280
gtttaacggt tgtggacaac aagccaggga tgtaacgcac tgagaagccc ttagagcctc    2340
tcaaagcaat tttgagtgac acaggaacac ttcgaaccgt acgggtcgac acaatctgag    2400
aatcccctgc aacattactt aacaaaaaag caggaataaa attaacaaga tgtaacagac    2460
ataagtccca tcaccgttgt ataaagttaa ctgtgggatt gcaaaagcat tcaagcctag    2520
gcgctgagct gtttgagcat cccggtggcc cttgtcgctg cctccgtgtt tctccctgga    2580
tttatttagg taatatctct cataaatccc cgggtagtta acgaaagtta atggagatca    2640
gtaacaataa ctctagggtc attactttgg actccctcag tttatccggg ggaattgtgt    2700
ttaagaaaat cccaactcat aaagtcaagt aggagattaa ttcaatgaat tctaaaggtg    2760
aagagctttt caccggagtt gtcccaattc tagttgaatt agatggtgac gttaatgggc    2820
ataagtttag tgtttctggt gaaggtgaag agacgcgac ttacggaaaa ctaactctaa    2880
agtttatttg tactacagga aaattacctg tgccctggcc taccttggtt acaacttttg    2940
cgtatggact acagtgtttt gctcgctatc cggatcacat gaaacagcat gatttcttta    3000
aaagtgctat gcctgaggga tatgtacagg aagaaccat cttttttaaa gatgatggaa    3060
actataagac ccgtgcagaa gttaaatttg aaggggatac tctggttaac agaattgaat    3120
taaaaggcat agattttaaa gaagatggaa atattttagg tcataagctg gaatataatt    3180
ataattctca taacgtttat atcatggctg ataaacaaaa gaatggtatt aaagtaaatt    3240
ttaaaattag acataatatc gaagatggat cagtacaatt agctgatcat tatcaacaaa    3300
atacccccat tggcgatgga cccgtcttac ttcccgataa tcattatta tccactcaat    3360 ctgccttaag taaagatcct aatgagaaga gagatcacat ggtttattta gaatttgtta    3420
ctgccgctgg aataacacat ggtatggatg agttatacaa ataatgagct cactagtcat    3480
```

```
atgagatctc tgcagactgt gcacgatatc caattgcatg gaaaaaacga caattacaag      3540
aaagtaaaac ttatgtcatc tatatgcttc gtgtatatta acttcctgtt acagagcttt      3600
acaaaactct cattaatcct ttagactaag tttagtcagt tccaatctga acatcgacaa      3660
atacataagg aattataacc aagcatgcaa cgtgaagctg ttattgcaga gtttctact       3720 caattatctg aagttgtagg tgttatcgaa agacatttag aacccacctt gttagcagta      3780
catttgtacg gaagtgctgt agatggaggt ctcaaacccc attctgacat tgatttattg      3840
gttacagtaa ctgttcgtct cgacgaaacc acccgccgtg ctttgattaa cgatttatta     3900
gaaacaagtg cctctccagg tgaatccgaa atcttgagag ctgttgaggt aacaatcgtt      3960
gtacatgacg atattatccc ttggcgttat cccgctaagc gtgaattaca atttggagaa      4020
tggcaacgta atgatatttt agcaggtatc tttgaacctg caactattga tattgactta      4080
gctattttgt taaccaaagc tagagaacat tctgttgcat tagtaggacc cgctgccgaa      4140
gagttgtttg atcccgtacc tgagcaagat ttatttgaag ctctcaacga aactttaacc      4200
ttatggaact cccctcccga ttgggcaggt gatgaacgta acgttgtatt aaccttgtct      4260
cgcatttggt acagtgctgt aactggtaaa attgcaccta agacgttgc cgctgattgg       4320 gcaatggaaa gattacccgc ccaatatcaa cccgtaattt tagaagctcg tcaagcctat     4380
ttgggtcaag aggaagatag attagcttct cgtgcagatc aattagaaga atttgttcat     4440
tatgtgaaag gagaaatcac aaaagtagtt gggaaataaa agcttccatg gcagcacgct      4500
tggactcctg ttgatagatc cagtaatgac ctcagaactc catctggatt tgttcagaac      4560
gctcggttgc cgccgggcgt tttttattgg tgagaatcca agcactgcta gcttgagatg      4620
tgtataagag acagctgttc tagaagcccct cttaaccact gaaatattaa ttagtttgtg     4680
agaaagtttc gtgtcaagag tgtaacggaa taaagttttt tcggttatta actaagatat      4740
gaacttatta ttattgttcc gaaaaaagtt tatgcagtct cttgacatga aatgaacaaa      4800
cgtataatca cattacaagg gctagggcga tgtttaagcg aagtgataaa accaaacctt      4860
aaagattcaa tttgagggtg ttcaggagtg atttaagact tgtaaattaa tttcaaccct     4920
atgaggattg aactagaccc ataaacccca aataagagca aaataccatc agcacagctt      4980
ccgtacctac ctcgcttata aaccgctttt tctttacttt ttcatcggct taacattctt      5040
acgactccta taggagttgt agagttctta aacaattact aaacaattaa tattttttcg      5100
ttaaagtcga tggttatggt tgtgtcagaa tgcacattag tgttgggtta gtgtggcgga      5160
catcattatg atctccacta aatac                                            5185
```

<210> SEQ ID NO 12
<211> LENGTH: 717
<212> TYPE: DNA
<213> ORGANISM: Artificial sequence
<220> FEATURE:
<223> OTHER INFORMATION: Codon-optimized version of a modified GFP variant gene

<400> SEQUENCE: 12

```
atgtccaaag gtgaagagct tttcaccgga gttgtcccaa ttctagttga attagatggt        60
gacgttaatg ggcataagtt tagtgttct ggtgaaggtg aaggagacgc gacttacgga       120
aaactaactc taaagtttat ttgtactaca ggaaaattac ctgtgccctg gcctaccttg      180
gttacaactt ttgcgtatgg actacagtgt tttgctcgct atccggatca catgaaacag      240
catgatttct ttaaaagtgc tatgcctgag ggatatgtac aggaaagaac catcttttt       300
```

```
aaagatgatg gaaactataa gacccgtgca gaagttaaat ttgaagggga tactctggtt    360
aacagaattg aattaaaagg catagatttt aagaagatg gaaatatttt aggtcataag    420
ctggaatata attataattc tcataacgtt tatatcatgg ctgataaaca aaagaatggt    480
attaaagtaa attttaaaat tagacataat atcgaagatg gatcagtaca attagctgat    540
cattatcaac aaaataccc cattggcgat ggacccgttt tacttcccga taatcattat    600
ttatccactc aatctgcctt aagtaaagat cctaatgaga agagagatca catggtttta    660
ttagaatttg ttactgccgc tggaataaca catggtatgg atgagttata caaataa      717
```

<210> SEQ ID NO 13
<211> LENGTH: 239
<212> TYPE: PRT
<213> ORGANISM: Artificial sequence
<220> FEATURE:
<223> OTHER INFORMATION: Translation of codon optimized version of modified GFP variant gene

<400> SEQUENCE: 13

```
Met Ala Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Phe Ser Tyr Gly Val Gln Cys Phe Ser Arg Tyr Pro Asp His Met Lys
65                  70                  75                  80

Arg His Asp Phe Phe Lys Ser Ala Met Pro Glu Gly Tyr Val Gln Glu
                85                  90                  95

Arg Thr Ile Ser Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr His Gly Met Asp Glu Leu Tyr Lys
225                 230                 235
```

<210> SEQ ID NO 14
<211> LENGTH: 720
<212> TYPE: DNA
<213> ORGANISM: Artificial sequence
<220> FEATURE:
<223> OTHER INFORMATION: Modified GFP (GFPmut2) gene

<400> SEQUENCE: 14

```
atggctagta aaggagaaga acttttcact ggagttgtcc caattcttgt tgaattagat      60
ggtgatgtta atgggcacaa attttctgtc agtggagagg gtgaaggtga tgcaacatac     120
ggaaaactta cccttaaatt tatttgcact actggaaaac tacctgttcc ttggccaaca     180
cttgtcacta ctttctctta tggtgttcaa tgcttttcaa gatacccaga tcatatgaag     240
cggcacgact tcttcaagag cgccatgcct gagggtacg tgcaggagag gaccatctct      300
ttcaaggacg acgggaacta caagacacgt gctgaagtca gtttgaggg agacaccctc      360
gtcaacagga tcgagcttaa gggaatcgat ttcaaggagg acggaaacat cctcggccac     420
aagttggaat acaactacaa ctcccacaac gtatacatca cggcagacaa acaaaagaat     480
ggaatcaaag ctaacttcaa aattagacac aacattgaag atggaagcgt tcaactagca     540
gaccattatc aacaaaatac tccaattggc gatggccctg tccttttacc agacaaccat     600
tacctgtcca cacaatctgc cctttcgaaa gatcccaacg aaaagagaga ccacatggtc     660
cttcttgagt ttgtaacagc tgctgggatt acacatggca tggatgaact atacaaataa     720
```

<210> SEQ ID NO 15
<211> LENGTH: 18
<212> TYPE: DNA
<213> ORGANISM: Cyanobacterium sp. ABICyano2

<400> SEQUENCE: 15

```
tagcaagata ttttgata                                                    18
```

<210> SEQ ID NO 16
<211> LENGTH: 354
<212> TYPE: DNA
<213> ORGANISM: Synechocystis sp. PCC6803

<400> SEQUENCE: 16

```
acaatctgag aatcccctgc aacattactt aacaaaaaag caggaataaa attaacaaga      60
tgtaacagac ataagtccca tcaccgttgt ataaagttaa ctgtgggatt gcaaaagcat     120
tcaagcctag gcgctgagct gtttgagcat cccggtggcc cttgtcgctg cctccgtgtt     180
tctccctgga tttatttagg taatatctct cataaatccc cgggtagtta acgaaagtta     240
atggagatca gtaacaataa ctctagggtc attactttgg actccctcag tttatccggg     300
ggaattgtgt ttaagaaaat cccaactcat aaagtcaagt aggagattaa ttca           354
```

<210> SEQ ID NO 17
<211> LENGTH: 278
<212> TYPE: DNA
<213> ORGANISM: Cyanobacterium sp. ABICyano1

<400> SEQUENCE: 17

```
aattaataac ttcttcctgt acgggcgaat ggccatttgc tcctaactaa ctccgtactg      60
ctttgcggaa cgagcgtagc gaactctccg aattactaag ccttcatccc tgatagatgc     120
aaaaaacgaa ttaaaattat gtgtaaaaag aaaatgtgtc tttatttagt agtcaaagtt     180
acaaatatt aagaatcaaa ttaataatgt attgggcagt taagtatata agtctttaaa      240
tatttatttg tattcaatat attaaccgag gacaaatt                              278
```

<210> SEQ ID NO 18
<211> LENGTH: 205
<212> TYPE: DNA
<213> ORGANISM: Cyanobacterium sp. ABICyano1

<400> SEQUENCE: 18

```
tagagtatga taaaatgaca aggaaaggat tattttctct tgtttaaatt ctcaagattc      60
ttatgcttat ttattttatg taagtgtctc ttttccttga aatagaaaga aaaaagtggc     120
taattttgag aaaagctaac aacgctttgg ttaactaaaa atcaaaagtg agattactga     180
tcgcttaaga aatggagtat tgatt                                          205
```

<210> SEQ ID NO 19
<211> LENGTH: 214
<212> TYPE: DNA
<213> ORGANISM: Cyanobacterium sp. ABICyano1

<400> SEQUENCE: 19

```
agagttatat ttacatagtg tgtgcgagta agggcaactt ttgtaggtag atgaataaac      60
ctcaaattac tcatcttaaa agacgatatt tttaatctat tcttctgtaa taaaatactt    120
ctttcgatag agatatttaa tacttttgag agatgaaaat aatttcaata attgtcatga    180
tagagagtaa gtgcaaataa gaaaaaattg attt                                214
```

<210> SEQ ID NO 20
<211> LENGTH: 338
<212> TYPE: DNA
<213> ORGANISM: Cyanobacterium sp. ABICyano1

<400> SEQUENCE: 20

```
gcagttagat aaataagtaa tgagcgggag aaatagggc aaatggccat tcgcccctac       60
agggaggtgg caggtgttag ggtgtttagg ggatgaggtg atgagggtag agggagataa     120
ggtgtcgggt ttcagatttc aggttttaga agaaagtaac gagtaattat caactattca     180
ctattcacta ttgcctgttg cccttctctc cttgaaatat aaaaaaatgt aaaaatatca     240
ttaagaaaag taacaaaata aacagaaagg ttgacaaagt tgacgcttta atatccgtat     300
gttagcttta taacaacgaa atcaacggag gagtgaaa                             338
```

<210> SEQ ID NO 21
<211> LENGTH: 408
<212> TYPE: DNA
<213> ORGANISM: Cyanobacterium sp. ABICyano1

<400> SEQUENCE: 21

```
cttgaaaaag ttgaggtatt aatagagctt gataaatgat aataaaaaca gatttagctc      60
ttatttttaag ggaaaaagaa ataaataaaa tattagtaaa tatcaaaaat atcagccttt    120
caaaaataat ttgactcttt tcaaaaaaaa atgttatctt taaggtatgc tttaaacctt    180
aaatacttct attggtaaca ctgttctcaa tcttatttca gattttccca ttgagcataa    240
ataaaatatt aagcagaagt agaaaaggtt gatattagca ataataaaaa ttaacaataa    300
aatgtgaaaa cagattacta ctgattattt attgccatga gctaattagt ataatttgt     360
cttttttgat cgaaaaatga aatttttaa gcggaggaac tgaaaatt                  408
```

<210> SEQ ID NO 22
<211> LENGTH: 411
<212> TYPE: DNA
<213> ORGANISM: Cyanobacterium sp. ABICyano1

<400> SEQUENCE: 22

```
tatttatata taaactcgaa taaaattatc aatataaagt caaactatat ctatcctatt      60
```

-continued

```
ttaactgcta ttggtaagtc ccttaattag tgttggggtg aatagatttt aaaagggcaa      120
accccccttt atcctccctc gagagggggg agggcaaaag gcaagggggca agggaaaaat     180 taagaattaa gaattaaaaa ctccgaacac ctgtaggggc gaatagccat tcgcttcccc     240 tcatccccc atctcccaa caccctaagc ccctactcgt tactcattta tttacatcat       300
ttatttacat cattaagaaa agtaacaaat tttgacaagt agtcttttga caggaaaaag    360
caaattctcg aagatgaaaa aatagaaaa aaattcaatc ttacagtaac g               411
```

```
<210> SEQ ID NO 23
<211> LENGTH: 211
<212> TYPE: DNA
<213> ORGANISM: Cyanobacterium sp. ABICyano1

<400> SEQUENCE: 23
gtgatatttg gtttattcta tattttcctt aagtaaaaat tcagtcatga gggaaacttt      60
tgttaaaatt tgctttaaat taataggaag atcattaaga aaatcttaaa aagattgagt     120
ttttagatcg aaattattga agaaaaatta acagggttc tgctcaaaat tttattaaat     180
tactctactg tagtaaagga gaaatttat t                                    211
```

```
<210> SEQ ID NO 24
<211> LENGTH: 542
<212> TYPE: DNA
<213> ORGANISM: Cyanobacterium sp. ABICyano1

<400> SEQUENCE: 24
gaatagttga taattactcg ttactcatta ctcacttaaa cctgccacct gatacctgcc      60
acctctcccc ccatcacctc atccctcaa cattccgaac cccttgacac tttgaactaa     120
aattgtatta aagtgcaaat ctggacgggg ttaaccagtg tgacttataa tagtaaacgc    180
tgttttttat aataaataag ctaaatattt aaaaactatg agtaaatata cactaaatgg    240
tactagacgt aagcagaaaa gaacctccgg ttttccgcgcc cgtatgagaa ccaaaaatgg   300
tagaaaagta attcaagctc gtcgtaataa gggtagaaaa agattagcag tataaaatta   360
ctgttaaata aggaagctaa gtttagcatt ttaagtttga tattactaat cattaaatttt   420 actgtgaaat ataggtggga ctaccatcaa agcatcgact gaaacggcgt ttaaatttcc    480 aatctgtttta tcaacagggt attcgccgct ctagtcgtta ttttattgtc cgagggttac    540
gg                                                                   542
```

```
<210> SEQ ID NO 25
<211> LENGTH: 380
<212> TYPE: DNA
<213> ORGANISM: Cyanobacterium sp. ABICyano1

<400> SEQUENCE: 25
ataaccaatg ggacttgaat tttagatcca tttatttaat tctattttttg ttacatttct    60 ttatattaat cagaattatg ttactttgtt ttgtttatg tcgttacctt attgaagaaa     120
gagtggatga gaaggtaaat gacggggcat aaatatcgat tcgttgtcag aataagctgt    180
tttattcact taactggttg tttgccaatt tctccctaat tcccataact tgtataacta    240
aatttaataa tcaattttag taaattaaga ataggttaaa agtagtattt agaattaagt    300 taacttttaat aaatttcctg tattttttta tagaaaaaag tataaaataa aaacatatca    360 aaaagtttg aaatgacaat                                                 380
```

<210> SEQ ID NO 26
<211> LENGTH: 41
<212> TYPE: DNA
<213> ORGANISM: Artificial Sequence
<220> FEATURE:
<223> OTHER INFORMATION: Synthetic promoter sequence

<400> SEQUENCE: 26
ggcgaattga cattgtgagc ggataacaat ataatgtgtg g                 41

<210> SEQ ID NO 27
<211> LENGTH: 604
<212> TYPE: DNA
<213> ORGANISM: Nostoc sp. PCC7120

<400> SEQUENCE: 27
gataacatca ccgtcgttat cgtcgcttta gaataacgtt cccaaaatag ctcatttcca    60
actggcaact cacaaccaaa aaccgcattt ttagtaaata tactcagcaa tttgttcaac   120
ctgagcattt ttcccatttg caacttgata caaatatttt tagcagcaaa ttttcctact   180
gccagcttag tttacataaa ttttgtctgt tgacatcttg cacacaataa ggtatggcgc   240
atataatgcg atattactac cattaattta ctacctagtc attaacgtct cccgccagag   300
aacagttttg aataggtagt caattttagg tattgaacct gctgtaaatt tattaaatcg   360
atgaatttcc ccgaaatctg ctctagcaga cttgggttat ataccagtag ctcaggtgc    420 aaaacaacaa agcacaaatt ttacccatta aggatatagg caatctgtca aatagttgtt   480
atctttctta atacagagga ataatcaaca atatggggca ggtactaact aaagtcctat   540
gcctgtgggg cttctgtaac cgacataacc tttacgcgtt gtcttttagg agtctgttat   600
gaac                                                               604

<210> SEQ ID NO 28
<211> LENGTH: 267
<212> TYPE: DNA
<213> ORGANISM: Synechocystis sp. PCC6803

<400> SEQUENCE: 28
tcgacatcag gaattgtaat tagaaagtcc aaaaattgta atttaaaaaa cagtcaatgg    60
agagcattgc cataagtaaa ggcatcccct gcgtgataag attaccttca gaaaacagat   120
agttgctggg ttatcgcaga ttttttctcgc aaccaaataa ctgtaaataa taactgtctc   180
tggggcgacg gtaggcttta tattgccaaa tttcgcccgt gggagaaagc taggctattc   240
aatgtttatg gaggactgac ctagatg                                      267

<210> SEQ ID NO 29
<211> LENGTH: 123
<212> TYPE: DNA
<213> ORGANISM: Synechococcus sp. PCC 7002

<400> SEQUENCE: 29
tcgactgtgg tctgtctttg ttcgctgatc taaacaatac ctgaataatt gttcatgtgt    60
taatctaaaa atgtgaacaa tcgttcaact atttaagaca ataccttgga ggtttaaacc   120
atg                                                                123

<210> SEQ ID NO 30
<211> LENGTH: 792
<212> TYPE: DNA
<213> ORGANISM: Shigella flexneri

<400> SEQUENCE: 30

```
atgagggaag cggtgatcgc cgaagtatcg actcaactat cagaggtagt tggcgtcatc    60
gagcgccatc tcgaaccgac gttgctggcc gtacatttgt acggctccgc agtggatggc   120
ggcctgaagc cacacagtga tattgatttg ctggttacgg tgaccgtaag gcttgatgaa   180
acaacgcggc gagctttgat caacgacctt ttggaaactt cggcttcccc tggagagagc   240
gagattctcc gcgctgtaga agtcaccatt gttgtgcacg acgacatcat tccgtggcgt   300
tatccagcta agcgcgaact gcaatttgga gaatggcagc gcaatgacat tcttgcaggt   360
atcttcgagc cagccacgat cgacattgat ctggctatct tgctgacaaa agcaagagaa   420
catagcgttg ccttggtagg tccagcggcg gaggaactct ttgatccggt tcctgaacag   480
gatctatttg aggcgctaaa tgaaaccta acgctatgga actcgccgcc cgactgggct   540
ggcgatgagc gaaatgtagt gcttacgttg tcccgcattt ggtacagcgc agtaaccggc   600
aaaatcgcgc cgaaggatgt cgctgccgac tgggcaatgg agcgcctgcc ggcccagtat   660
cagcccgtca tacttgaagc tagacaggct tatcttggac aagaagaaga tcgcttggcc   720
tcgcgcgcag atcagttgga gaatttgtc cactacgtga aggcgagat caccaaggta   780
gtcggcaaat aa                                                       792
```

<210> SEQ ID NO 31
<211> LENGTH: 263
<212> TYPE: PRT
<213> ORGANISM: Shigella flexneri

<400> SEQUENCE: 31

```
Met Arg Glu Ala Val Ile Ala Glu Val Ser Thr Gln Leu Ser Glu Val
1               5                   10                  15

Val Gly Val Ile Glu Arg His Leu Glu Pro Thr Leu Leu Ala Val His
            20                  25                  30

Leu Tyr Gly Ser Ala Val Asp Gly Gly Leu Lys Pro His Ser Asp Ile
        35                  40                  45

Asp Leu Leu Val Thr Val Thr Val Arg Leu Asp Glu Thr Thr Arg Arg
    50                  55                  60

Ala Leu Ile Asn Asp Leu Leu Glu Thr Ser Ala Ser Pro Gly Glu Ser
65                  70                  75                  80

Glu Ile Leu Arg Ala Val Glu Val Thr Ile Val Val His Asp Asp Ile
                85                  90                  95

Ile Pro Trp Arg Tyr Pro Ala Lys Arg Glu Leu Gln Phe Gly Glu Trp
            100                 105                 110

Gln Arg Asn Asp Ile Leu Ala Gly Ile Phe Glu Pro Ala Thr Ile Asp
        115                 120                 125

Ile Asp Leu Ala Ile Leu Leu Thr Lys Ala Arg Glu His Ser Val Ala
    130                 135                 140

Leu Val Gly Pro Ala Ala Glu Glu Leu Phe Asp Pro Val Pro Glu Gln
145                 150                 155                 160

Asp Leu Phe Glu Ala Leu Asn Glu Thr Leu Thr Leu Trp Asn Ser Pro
                165                 170                 175

Pro Asp Trp Ala Gly Asp Glu Arg Asn Val Val Leu Thr Leu Ser Arg
            180                 185                 190

Ile Trp Tyr Ser Ala Val Thr Gly Lys Ile Ala Pro Lys Asp Val Ala
        195                 200                 205

Ala Asp Trp Ala Met Glu Arg Leu Pro Ala Gln Tyr Gln Pro Val Ile
    210                 215                 220
```

```
Leu Glu Ala Arg Gln Ala Tyr Leu Gly Gln Glu Asp Arg Leu Ala
225                 230                 235                 240

Ser Arg Ala Asp Gln Leu Glu Glu Phe Val His Tyr Val Lys Gly Glu
                245                 250                 255

Ile Thr Lys Val Val Gly Lys
            260
```

<210> SEQ ID NO 32
<211> LENGTH: 753
<212> TYPE: DNA
<213> ORGANISM: Campylobacter jejuni

<400> SEQUENCE: 32

```
atgaaatata tcgatgaaat tcaaattctg ggaaaatgtt cagagggtat gtctccagca      60
gaagtatata aatgccagct taaaaatact gtatgctatc tgaaaaaaat tgacgatata     120
ttttcaaaaa ccacatacag cgtgaaaaga gaagctgaga tgatgatgtg gttatccgat     180
aaactgaaag taccagatgt aatcgaatac ggagtacgag aacattcaga atatttgatc     240
atgagtgagt taaggggggaa acacatagat tgctttattg atcatccaat aaaatatatt     300
gagtgcttgg taaacgcact tcatcagcta caagcaatag atataagaaa ctgcccattt     360
tcatccaaaa tagatgttcg attaaaagaa ctaaaatatc ttttggataa cagaattgcc     420
gatattgatg tatcgaattg ggaagataca acagaatttg atgatccaat gacgttatat     480
cagtggcttt gcgaaaatca acctcaagaa gaactgtgtc tctctcatgg agatatgagc     540
gctaattttt ttgtatctca tgatggaata tattttatg atttggcaag atgtggagtt     600
gcagacaaat ggttggatat agcatttgt gtcagagaga ttcgagaata ttatcctgat     660
tctgattatg aaaaattctt ttttaacatg ttgggacttg aaccggatta taaaaaaatt     720
aactattaca ttttattaga tgagatgttt tag                                   753
```

<210> SEQ ID NO 33
<211> LENGTH: 250
<212> TYPE: PRT
<213> ORGANISM: Campylobacter jejuni

<400> SEQUENCE: 33

```
Met Lys Tyr Ile Asp Glu Ile Gln Ile Leu Gly Lys Cys Ser Glu Gly
1               5                   10                  15

Met Ser Pro Ala Glu Val Tyr Lys Cys Gln Leu Lys Asn Thr Val Cys
            20                  25                  30

Tyr Leu Lys Lys Ile Asp Asp Ile Phe Ser Lys Thr Thr Tyr Ser Val
        35                  40                  45

Lys Arg Glu Ala Glu Met Met Met Trp Leu Ser Asp Lys Leu Lys Val
    50                  55                  60

Pro Asp Val Ile Glu Tyr Gly Val Arg Glu His Ser Glu Tyr Leu Ile
65                  70                  75                  80

Met Ser Glu Leu Arg Gly Lys His Ile Asp Cys Phe Ile Asp His Pro
                85                  90                  95

Ile Lys Tyr Ile Glu Cys Leu Val Asn Ala Leu His Gln Leu Gln Ala
            100                 105                 110

Ile Asp Ile Arg Asn Cys Pro Phe Ser Ser Lys Ile Asp Val Arg Leu
        115                 120                 125

Lys Glu Leu Lys Tyr Leu Leu Asp Asn Arg Ile Ala Asp Ile Asp Val
    130                 135                 140
```

Ser Asn Trp Glu Asp Thr Thr Glu Phe Asp Asp Pro Met Thr Leu Tyr
145                 150                 155                 160

Gln Trp Leu Cys Glu Asn Gln Pro Gln Glu Glu Leu Cys Leu Ser His
            165                 170                 175

Gly Asp Met Ser Ala Asn Phe Phe Val Ser His Asp Gly Ile Tyr Phe
        180                 185                 190

Tyr Asp Leu Ala Arg Cys Gly Val Ala Asp Lys Trp Leu Asp Ile Ala
    195                 200                 205

Phe Cys Val Arg Glu Ile Arg Glu Tyr Tyr Pro Asp Ser Asp Tyr Glu
210                 215                 220

Lys Phe Phe Asn Met Leu Gly Leu Glu Pro Asp Tyr Lys Lys Ile
225                 230                 235                 240

Asn Tyr Tyr Ile Leu Leu Asp Glu Met Phe
            245                 250

<210> SEQ ID NO 34
<211> LENGTH: 753
<212> TYPE: DNA
<213> ORGANISM: Artificial sequence
<220> FEATURE:
<223> OTHER INFORMATION: Codon optimized version of the aphA7 gene
      originally from Campylobacter jejuni

<400> SEQUENCE: 34
atgaaatata ttgatgaaat ccaaattttg ggtaaatgta gtgaaggaat gtccccagca      60
gaagtttata atgtcaact caaaaatact gtttgttatt aaagaaaat tgatgacatt      120 ttctctaaaa ccactattc cgttaaacgt gaagctgaaa tgatgatgtg gttaagcgat      180
aaattaaaag ttcctgatgt aattgagtac ggtgtacgtg aacattctga atacttgatt      240
atgagtgaac ttcgtggaaa acatattgat tgcttcattg accatcctat caaatatatt      300
gaatgtttag taaacgcact ccaccaatta caggccattg atattagaaa ttgtcctttt      360
tcctctaaaa ttgatgtacg tctcaaggaa ttaaaatatc tcctcgataa tagaattgct      420
gatattgatg tctctaactg ggaagatact accgagtttg acgatcccat gacccttat      480 caatggctct gtgaaaacca gccccaagaa gaattatgtt tatctcacgg tgatatgtca      540
gcaaactttt ttgtaagcca tgatggaatc tacttctatg acttagctcg ttgtggagta      600
gccgataaat ggctagatat tgcttttgt gtacgtgaaa ttagagaata ttaccctgac      660
tccgattatg agaaattttt ctttaatatg ttaggtttgg aaccagatta caagaaaatt      720
aactactata ttttgttaga tgaaatgttt taa                                  753

<210> SEQ ID NO 35
<211> LENGTH: 250
<212> TYPE: PRT
<213> ORGANISM: Campylobacter jejuni

<400> SEQUENCE: 35

Met Lys Tyr Ile Asp Glu Ile Gln Ile Leu Gly Lys Cys Ser Glu Gly
1               5                   10                  15

Met Ser Pro Ala Glu Val Tyr Lys Cys Gln Leu Lys Asn Thr Val Cys
            20                  25                  30

Tyr Leu Lys Lys Ile Asp Asp Ile Phe Ser Lys Thr Thr Tyr Ser Val
        35                  40                  45

Lys Arg Glu Ala Glu Met Met Met Trp Leu Ser Asp Lys Leu Lys Val
    50                  55                  60

Pro Asp Val Ile Glu Tyr Gly Val Arg Glu His Ser Glu Tyr Leu Ile

```
                65                  70                  75                  80
Met Ser Glu Leu Arg Gly Lys His Ile Asp Cys Phe Ile Asp His Pro
                    85                  90                  95

Ile Lys Tyr Ile Glu Cys Leu Val Asn Ala Leu His Gln Leu Gln Ala
                100                 105                 110

Ile Asp Ile Arg Asn Cys Pro Phe Ser Ser Lys Ile Asp Val Arg Leu
            115                 120                 125

Lys Glu Leu Lys Tyr Leu Leu Asp Asn Arg Ile Ala Asp Ile Asp Val
        130                 135                 140

Ser Asn Trp Glu Asp Thr Thr Glu Phe Asp Asp Pro Met Thr Leu Tyr
145                 150                 155                 160

Gln Trp Leu Cys Glu Asn Gln Pro Gln Glu Leu Cys Leu Ser His
                165                 170                 175

Gly Asp Met Ser Ala Asn Phe Phe Val Ser His Asp Gly Ile Tyr Phe
                180                 185                 190

Tyr Asp Leu Ala Arg Cys Gly Val Ala Asp Lys Trp Leu Asp Ile Ala
            195                 200                 205

Phe Cys Val Arg Glu Ile Arg Glu Tyr Tyr Pro Asp Ser Asp Tyr Glu
        210                 215                 220

Lys Phe Phe Asn Met Leu Gly Leu Glu Pro Asp Tyr Lys Lys Ile
225                 230                 235                 240

Asn Tyr Tyr Ile Leu Leu Asp Glu Met Phe
                245                 250

<210> SEQ ID NO 36
<211> LENGTH: 534
<212> TYPE: DNA
<213> ORGANISM: Pseudomonas aeruginosa

<400> SEQUENCE: 36
atgttacgca gcagcaacga tgttacgcag cagggcagtc gccctaaaac aaagttaggt      60
ggctcaagta tgggcatcat tcgcacatgt aggctcggcc ctgaccaagt caaatccatg     120
cgggctgctc ttgatctttt cggtcgtgag ttcggagacg tagccaccta ctcccaacat     180
cagccggact ccgattacct cgggaacttg ctccgtagta agacattcat cgcgcttgct     240
gccttcgacc aagaagcggt tgttggcgct ctcgcggctt acgttctgcc caggtttgag     300
cagccgcgta gtgagatcta tatctatgat ctcgcagtct ccggcgagca ccggaggcag     360
ggcattgcca ccgcgctcat caatctcctc aagcatgagg ccaacgcgct tggtgcttat     420
gtgatctacg tgcaagcaga ttacggtgac gatcccgcag tggctctcta tacaaagttg     480
ggcatacggg aagaagtgat gcactttgat atcgacccaa gtaccgccac ctaa           534

<210> SEQ ID NO 37
<211> LENGTH: 177
<212> TYPE: PRT
<213> ORGANISM: Pseudomonas aeruginosa

<400> SEQUENCE: 37

Met Leu Arg Ser Ser Asn Asp Val Thr Gln Gln Gly Ser Arg Pro Lys
1               5                   10                  15

Thr Lys Leu Gly Gly Ser Ser Met Gly Ile Ile Arg Thr Cys Arg Leu
            20                  25                  30

Gly Pro Asp Gln Val Lys Ser Met Arg Ala Ala Leu Asp Leu Phe Gly
        35                  40                  45

Arg Glu Phe Gly Asp Val Ala Thr Tyr Ser Gln His Gln Pro Asp Ser
```

```
Asp Tyr Leu Gly Asn Leu Leu Arg Ser Lys Thr Phe Ile Ala Leu Ala
 65                  70                  75                  80

Ala Phe Asp Gln Glu Ala Val Val Gly Ala Leu Ala Ala Tyr Val Leu
                 85                  90                  95

Pro Arg Phe Glu Gln Pro Arg Ser Glu Ile Tyr Ile Tyr Asp Leu Ala
            100                 105                 110

Val Ser Gly Glu His Arg Arg Gln Gly Ile Ala Thr Ala Leu Ile Asn
        115                 120                 125

Leu Leu Lys His Glu Ala Asn Ala Leu Gly Ala Tyr Val Ile Tyr Val
    130                 135                 140

Gln Ala Asp Tyr Gly Asp Pro Ala Val Ala Leu Tyr Thr Lys Leu
145                 150                 155                 160

Gly Ile Arg Glu Glu Val Met His Phe Asp Ile Asp Pro Ser Thr Ala
                165                 170                 175

Thr

<210> SEQ ID NO 38
<211> LENGTH: 534
<212> TYPE: DNA
<213> ORGANISM: Artificial sequence
<220> FEATURE:
<223> OTHER INFORMATION: Codon optimized version of accC1 gene
      originally from Pseudomonas aeruginosa

<400> SEQUENCE: 38
atgttacgtt cttccaacga tgttacacaa cagggtagtc gtcctaaaac caaattagga      60
ggtagttcta tgggtatcat tagaacctgt cgtttaggtc ccgatcaagt taagagtatg     120
cgtgctgcat tagatttatt cggtcgtgaa tttggtgatg tagccaccta tagtcaacat     180
caacctgatt ccgactattt gggtaatctc ttacgctcta aaaccttcat tgccttagct     240
gcatttgacc aagaagctgt agtgggtgct ttggccgctt atgttttacc agatttgaa     300 caaccacgtt ctgaaatcta tatttatgat ttggctgttt ctggtgagca tcgtcgccaa     360
ggtatcgcta ccgctttaat caacttattg aaacacgaag ctaatgcttt aggtgcctat     420
gtaatttatg tgcaagcaga ctatggtgat gaccctgctg ttgctttata taaaaactc     480 ggtattagag aagaagttat gcactttgat attgacccta gtactgcaac ctaa           534

<210> SEQ ID NO 39
<211> LENGTH: 177
<212> TYPE: PRT
<213> ORGANISM: Pseudomonas aeruginosa

<400> SEQUENCE: 39

Met Leu Arg Ser Ser Asn Asp Val Thr Gln Gln Gly Ser Arg Pro Lys
 1               5                  10                  15

Thr Lys Leu Gly Gly Ser Ser Met Gly Ile Ile Arg Thr Cys Arg Leu
                20                  25                  30

Gly Pro Asp Gln Val Lys Ser Met Arg Ala Ala Leu Asp Leu Phe Gly
            35                  40                  45

Arg Glu Phe Gly Asp Val Ala Thr Tyr Ser Gln His Gln Pro Asp Ser
        50                  55                  60

Asp Tyr Leu Gly Asn Leu Leu Arg Ser Lys Thr Phe Ile Ala Leu Ala
 65                  70                  75                  80

Ala Phe Asp Gln Glu Ala Val Val Gly Ala Leu Ala Ala Tyr Val Leu
                 85                  90                  95
```

```
Pro Arg Phe Glu Gln Pro Arg Ser Glu Ile Tyr Ile Tyr Asp Leu Ala
            100                 105                 110
Val Ser Gly Glu His Arg Arg Gln Gly Ile Ala Thr Ala Leu Ile Asn
        115                 120                 125
Leu Leu Lys His Glu Ala Asn Ala Leu Gly Ala Tyr Val Ile Tyr Val
    130                 135                 140
Gln Ala Asp Tyr Gly Asp Pro Ala Val Ala Leu Tyr Thr Lys Leu
145                 150                 155                 160
Gly Ile Arg Glu Glu Val Met His Phe Asp Ile Asp Pro Ser Thr Ala
                165                 170                 175
Thr
```

<210> SEQ ID NO 40
<211> LENGTH: 1710
<212> TYPE: DNA
<213> ORGANISM: Zymomonas mobilis

<400> SEQUENCE: 40

```
atgaattctt atactgtcgg tacctattta gcggagcggc ttgtccagat tggtctcaag      60
catcacttcg cagtcgcggg cgactacaac ctcgtccttc ttgacaacct gcttttgaac     120
aaaaacatgg agcaggttta ttgctgtaac gaactgaact gcggtttcag tgcagaaggt     180
tatgctcgtg ccaaaggcgc agcagcagcc gtcgttacct acagcgtcgg tgcgctttcc     240
gcatttgatg ctatcggtgg cgcctatgca gaaaaccttc cggttatcct gatctccggt     300
gctccgaaca caatgatca cgctgctggt cacgtgttgc atcacgctct tggcaaaacc     360
gactatcact atcagttgga atggccaag aacatcacgg ccgcagctga agcgatttac     420
accccagaag aagctccggc taaaatcgat cacgtgatta aaactgctct tcgtgagaag     480
aagccggttt atctcgaaat cgcttgcaac attgcttcca tgccctgcgc cgctcctgga     540
ccggcaagcg cattgttcaa tgacgaagcc agcgacgaag cttctttgaa tgcagcggtt     600
gaagaaaccc tgaaattcat cgccaaccgc gacaaagttg ccgtcctcgt cggcagcaag     660
ctgcgcgcag ctggtgctga agaagctgct gtcaaatttg ctgatgctct cggtggcgca     720
gttgctacca tggctgctgc aaaaagcttc ttcccagaag aaaacccgca ttacatcggt     780
acctcatggg gtgaagtcag ctatccgggc gttgaaaaga cgatgaaaga agccgatgcg     840
gttatcgctc tggctcctgt cttcaacgac tactccacca ctggttggac ggatattcct     900
gatcctaaga aactggttct cgctgaaccg cgttctgtcg tcgttaacgg cgttcgcttc     960
cccagcgttc atctgaaaga ctatctgacc cgtttggctc agaaagtttc caagaaaacc    1020
ggtgctttgg acttcttcaa atccctcaat gcaggtgaac tgaagaaagc cgctccggct    1080
gatccgagtg ctccgttggt caacgcagaa atcgcccgtc aggtcgaagc tcttctgacc    1140
ccgaacacga cggttattgc tgaaaccggt gactcttggt tcaatgctca gcgcatgaag    1200
ctcccgaacg gtgctcgcgt tgaatatgaa atgcagtggg gtcacatcgg ttggtccgtt    1260
cctgccgcct tcggttatgc cgtcggtgct ccggaacgtc gcaacatcct catggttggt    1320
gatggttcct tccagctgac ggctcaggaa gtcgctcaga tggttcgcct gaaactgccg    1380
gttatcatct tcttgatcaa taactatggt tacaccatcg aagttatgat ccatgatggt    1440
ccgtacaaca acatcaagaa ctgggattat gccggtctga tggaagtgtt caacggtaac    1500
ggtggttatg acagcggtgc tggtaaaggc ctgaaggcta aaccggtgg cgaactggca    1560
gaagctatca aggttgctct ggcaaacacc gacggcccaa ccctgatcga atgcttcatc    1620
```
ggtcgtgaag actgcactga agaattggtc aaatggggta agcgcgttgc tgccgccaac    1680
agccgtaagc ctgttaacaa gctcctctag                                     1710

<210> SEQ ID NO 41
<211> LENGTH: 569
<212> TYPE: PRT
<213> ORGANISM: Zymomonas mobilis

<400> SEQUENCE: 41

Met Asn Ser Tyr Thr Val Gly Thr Tyr Leu Ala Glu Arg Leu Val Gln
1               5                   10                  15

Ile Gly Leu Lys His His Phe Ala Val Ala Gly Asp Tyr Asn Leu Val
            20                  25                  30

Leu Leu Asp Asn Leu Leu Leu Asn Lys Asn Met Glu Gln Val Tyr Cys
        35                  40                  45

Cys Asn Glu Leu Asn Cys Gly Phe Ser Ala Glu Gly Tyr Ala Arg Ala
    50                  55                  60

Lys Gly Ala Ala Ala Ala Val Val Thr Tyr Ser Val Gly Ala Leu Ser
65                  70                  75                  80

Ala Phe Asp Ala Ile Gly Gly Ala Tyr Ala Glu Asn Leu Pro Val Ile
                85                  90                  95

Leu Ile Ser Gly Ala Pro Asn Asn Asp His Ala Ala Gly His Val
            100                 105                 110

Leu His His Ala Leu Gly Lys Thr Asp Tyr His Tyr Gln Leu Glu Met
        115                 120                 125

Ala Lys Asn Ile Thr Ala Ala Ala Glu Ala Ile Tyr Thr Pro Glu Glu
    130                 135                 140

Ala Pro Ala Lys Ile Asp His Val Ile Lys Thr Ala Leu Arg Glu Lys
145                 150                 155                 160

Lys Pro Val Tyr Leu Glu Ile Ala Cys Asn Ile Ala Ser Met Pro Cys
                165                 170                 175

Ala Ala Pro Gly Pro Ala Ser Ala Leu Phe Asn Asp Glu Ala Ser Asp
            180                 185                 190

Glu Ala Ser Leu Asn Ala Ala Val Glu Glu Thr Leu Lys Phe Ile Ala
        195                 200                 205

Asn Arg Asp Lys Val Ala Val Leu Val Gly Ser Lys Leu Arg Ala Ala
    210                 215                 220

Gly Ala Glu Glu Ala Ala Val Lys Phe Ala Asp Ala Leu Gly Gly Ala
225                 230                 235                 240

Val Ala Thr Met Ala Ala Ala Lys Ser Phe Phe Pro Glu Glu Asn Pro
                245                 250                 255

His Tyr Ile Gly Thr Ser Trp Gly Glu Val Ser Tyr Pro Gly Val Glu
            260                 265                 270

Lys Thr Met Lys Glu Ala Asp Ala Val Ile Ala Leu Ala Pro Val Phe
        275                 280                 285

Asn Asp Tyr Ser Thr Thr Gly Trp Thr Asp Ile Pro Asp Pro Lys Lys
    290                 295                 300

Leu Val Leu Ala Glu Pro Arg Ser Val Val Asn Gly Val Arg Phe
305                 310                 315                 320

Pro Ser Val His Leu Lys Asp Tyr Leu Thr Arg Leu Ala Gln Lys Val
                325                 330                 335

Ser Lys Lys Thr Gly Ala Leu Asp Phe Phe Lys Ser Leu Asn Ala Gly
            340                 345                 350

```
Glu Leu Lys Lys Ala Ala Pro Ala Asp Pro Ser Ala Pro Leu Val Asn
            355                 360                 365

Ala Glu Ile Ala Arg Gln Val Glu Ala Leu Leu Thr Pro Asn Thr Thr
    370                 375                 380

Val Ile Ala Glu Thr Gly Asp Ser Trp Phe Asn Ala Gln Arg Met Lys
385                 390                 395                 400

Leu Pro Asn Gly Ala Arg Val Glu Tyr Glu Met Gln Trp Gly His Ile
                405                 410                 415

Gly Trp Ser Val Pro Ala Ala Phe Gly Tyr Ala Val Gly Ala Pro Glu
            420                 425                 430

Arg Arg Asn Ile Leu Met Val Gly Asp Gly Ser Phe Gln Leu Thr Ala
            435                 440                 445

Gln Glu Val Ala Gln Met Val Arg Leu Lys Leu Pro Val Ile Ile Phe
    450                 455                 460

Leu Ile Asn Asn Tyr Gly Tyr Thr Ile Glu Val Met Ile His Asp Gly
465                 470                 475                 480

Pro Tyr Asn Asn Ile Lys Asn Trp Asp Tyr Ala Gly Leu Met Glu Val
                485                 490                 495

Phe Asn Gly Asn Gly Gly Tyr Asp Ser Gly Ala Gly Lys Gly Leu Lys
            500                 505                 510

Ala Lys Thr Gly Gly Glu Leu Ala Glu Ala Ile Lys Val Ala Leu Ala
            515                 520                 525

Asn Thr Asp Gly Pro Thr Leu Ile Glu Cys Phe Ile Gly Arg Glu Asp
    530                 535                 540

Cys Thr Glu Glu Leu Val Lys Trp Gly Lys Arg Val Ala Ala Ala Asn
545                 550                 555                 560

Ser Arg Lys Pro Val Asn Lys Leu Leu
                565

<210> SEQ ID NO 42
<211> LENGTH: 1710
<212> TYPE: DNA
<213> ORGANISM: Artificial Sequence
<220> FEATURE:
<223> OTHER INFORMATION: Codon optimized version of PDC gene from
      Zymomonas mobilis

<400> SEQUENCE: 42
atgaattctt acactgttgg aacctattta gcagaacgtt tagttcaaat tggtctcaaa      60
caccattttg cagtagctgg tgattataat ttagttttat tggataactt attgttaaat     120
aagaatatgg aacaagtgta ttgttgtaat gaattaaact gtggtttttc tgctgaggga     180
tatgctcgtg caaaaggtgc tgccgcagca gttgttactt attctgttgg agcattaagt     240
gcttttgacg ctattggagg tgcttatgca gaaaatttac ctgtaatctt aatctctggt     300
gcacccaata caacgatca cgctgctggt catgtattgc atcatgcttt aggtaaaacc     360
gattatcatt accaattaga aatggcaaaa aatattaccg ctgccgcaga agctatttat     420
actcccgaag aagcacctgc taagatcgat cacgtaatta aaaccgctct ccgtgagaaa     480
aaacccgtat atttagaaat cgcttgcaat atcgcttcta tgccttgtgc agctcctgga     540
cctgctagtg ctttatttaa cgatgaagca tctgatgagg ctagtttaaa tgccgctgtt     600
gaagaaactt tgaaatttat tgctaatcgt gataaagtag ctgtttagt tggttctaaa     660 ctccgtgccg ctggtgcaga agaagcggct gtaaaattcg cagatgcctt aggaggtgct     720
gttgccacaa tggcagccgc taaaagtttt tccccgaag aaaatcctca ttacattggt     780
```

```
acttcttggg gtgaggtatc ttaccctggt gtagaaaaaa ccatgaagga agctgatgca      840
gtaattgcat tagctcctgt tttcaatgat tactctacca ctggttggac tgatattcca      900
gaccccaaaa aattagtttt agcagaacct cgctctgtag ttgtgaatgg tgttagattt      960
cccagtgtac atctcaaaga ttatttaact cgtttagctc aaaaagtgag taaaaagact     1020
ggcgcactcg atttctttaa atctttaaat gctggtgaat aaagaaagc agctcctgct      1080 gatcccagtg ctcctttagt gaatgccgaa atcgcaagac aagttgaagc cttgttaact     1140
cctaacacta ccgttattgc cgagactggt gatagttggt tcaatgctca acgcatgaaa     1200
ttacccaatg gtgctcgtgt tgagtatgaa atgcaatggg gtcacattgg atggtctgtt     1260
cctgctgcat ttggatatgc agttggagca cctgagcgta gaaacatttt aatggtaggt     1320
gatggttctt tccaactcac tgctcaagaa gttgcacaaa tggtacgttt aaaattgcct     1380
gttattatct ttctcattaa caactatggt tacaccattg aagttatgat tcatgatggt     1440
ccttataata acattaagaa ttgggattac gcaggtttaa tggaggtatt taacggtaat     1500
ggtggatacg acagtggagc aggtaaagga ttaaaagcta aaacaggagg tgagttagct     1560
gaagcaatta agtagctttt agccaataca gatggtccta ccttaatcga atgtttcatt     1620
ggacgtgaag attgtactga agagttagtt aaatggggaa agcgtgttgc cgctgcaaat     1680
tctcgtaaac ctgtaaacaa actcttgtag                                      1710
```

```
<210> SEQ ID NO 43
<211> LENGTH: 569
<212> TYPE: PRT
<213> ORGANISM: Zymomonas mobilis

<400> SEQUENCE: 43

Met Asn Ser Tyr Thr Val Gly Thr Tyr Leu Ala Glu Arg Leu Val Gln
1               5                   10                  15

Ile Gly Leu Lys His His Phe Ala Val Ala Gly Asp Tyr Asn Leu Val
            20                  25                  30

Leu Leu Asp Asn Leu Leu Leu Asn Lys Asn Met Glu Gln Val Tyr Cys
        35                  40                  45

Cys Asn Glu Leu Asn Cys Gly Phe Ser Ala Glu Gly Tyr Ala Arg Ala
    50                  55                  60

Lys Gly Ala Ala Ala Val Val Thr Tyr Ser Val Gly Ala Leu Ser
65                  70                  75                  80

Ala Phe Asp Ala Ile Gly Gly Ala Tyr Ala Glu Asn Leu Pro Val Ile
                85                  90                  95

Leu Ile Ser Gly Ala Pro Asn Asn Asn Asp His Ala Ala Gly His Val
            100                 105                 110

Leu His His Ala Leu Gly Lys Thr Asp Tyr His Tyr Gln Leu Glu Met
        115                 120                 125

Ala Lys Asn Ile Thr Ala Ala Ala Glu Ala Ile Tyr Thr Pro Glu Glu
    130                 135                 140

Ala Pro Ala Lys Ile Asp His Val Ile Lys Thr Ala Leu Arg Glu Lys
145                 150                 155                 160

Lys Pro Val Tyr Leu Glu Ile Ala Cys Asn Ile Ala Ser Met Pro Cys
                165                 170                 175

Ala Ala Pro Gly Pro Ala Ser Ala Leu Phe Asn Asp Glu Ala Ser Asp
            180                 185                 190

Glu Ala Ser Leu Asn Ala Ala Val Glu Glu Thr Leu Lys Phe Ile Ala
        195                 200                 205
```

Asn Arg Asp Lys Val Ala Val Leu Val Gly Ser Lys Leu Arg Ala Ala
    210                 215                 220

Gly Ala Glu Glu Ala Ala Val Lys Phe Ala Asp Ala Leu Gly Gly Ala
225                 230                 235                 240

Val Ala Thr Met Ala Ala Lys Ser Phe Phe Pro Glu Glu Asn Pro
            245                 250                 255

His Tyr Ile Gly Thr Ser Trp Gly Glu Val Ser Tyr Pro Gly Val Glu
            260                 265                 270

Lys Thr Met Lys Glu Ala Asp Ala Val Ile Ala Leu Ala Pro Val Phe
        275                 280                 285

Asn Asp Tyr Ser Thr Thr Gly Trp Thr Asp Ile Pro Asp Pro Lys Lys
290                 295                 300

Leu Val Leu Ala Glu Pro Arg Ser Val Val Asn Gly Val Arg Phe
305                 310                 315                 320

Pro Ser Val His Leu Lys Asp Tyr Leu Thr Arg Leu Ala Gln Lys Val
            325                 330                 335

Ser Lys Lys Thr Gly Ala Leu Asp Phe Phe Lys Ser Leu Asn Ala Gly
            340                 345                 350

Glu Leu Lys Lys Ala Ala Pro Ala Asp Pro Ser Ala Pro Leu Val Asn
        355                 360                 365

Ala Glu Ile Ala Arg Gln Val Glu Ala Leu Leu Thr Pro Asn Thr Thr
370                 375                 380

Val Ile Ala Glu Thr Gly Asp Ser Trp Phe Asn Ala Gln Arg Met Lys
385                 390                 395                 400

Leu Pro Asn Gly Ala Arg Val Glu Tyr Glu Met Gln Trp Gly His Ile
            405                 410                 415

Gly Trp Ser Val Pro Ala Ala Phe Gly Tyr Ala Val Gly Ala Pro Glu
            420                 425                 430

Arg Arg Asn Ile Leu Met Val Gly Asp Gly Ser Phe Gln Leu Thr Ala
        435                 440                 445

Gln Glu Val Ala Gln Met Val Arg Leu Lys Leu Pro Val Ile Ile Phe
450                 455                 460

Leu Ile Asn Asn Tyr Gly Tyr Thr Ile Glu Val Met Ile His Asp Gly
465                 470                 475                 480

Pro Tyr Asn Asn Ile Lys Asn Trp Asp Tyr Ala Gly Leu Met Glu Val
            485                 490                 495

Phe Asn Gly Asn Gly Gly Tyr Asp Ser Gly Ala Gly Lys Gly Leu Lys
            500                 505                 510

Ala Lys Thr Gly Gly Glu Leu Ala Glu Ala Ile Lys Val Ala Leu Ala
        515                 520                 525

Asn Thr Asp Gly Pro Thr Leu Ile Glu Cys Phe Ile Gly Arg Glu Asp
530                 535                 540

Cys Thr Glu Glu Leu Val Lys Trp Gly Lys Arg Val Ala Ala Ala Asn
545                 550                 555                 560

Ser Arg Lys Pro Val Asn Lys Leu Leu
            565

<210> SEQ ID NO 44
<211> LENGTH: 1011
<212> TYPE: DNA
<213> ORGANISM: Synechocystis sp. 6803

<400> SEQUENCE: 44
atgattaaag cctacgctgc cctggaagcc aacggaaaac tccaacccctt tgaatacgac    60

```
cccggtgccc tgggtgctaa tgaggtggag attgaggtgc agtattgtgg ggtgtgccac    120
agtgatttgt ccatgattaa taacgaatgg ggcatttcca attacccct agtgccgggt     180 catgaggtgg tgggtactgt ggccgccatg ggcgaagggg tgaaccatgt tgaggtgggg    240
gatttagtgg ggctgggttg gcattcgggc tactgcatga cctgccatag ttgtttatct    300
ggctaccaca acctttgtgc cacggcggaa tcgaccattg tgggccacta cggtggcttt    360
ggcgatcggg ttcgggccaa gggagtcagc gtggtgaaat acctaaagg cattgaccta     420 gccagtgccg ggccctttt ctgtggagga attaccgttt tcagtcctat ggtggaactg     480
agtttaaagc ccactgcaaa agtggcagtg atcggcattg ggggcttggg ccatttagcg    540 gtgcaattc tccgggcctg gggctgtgaa gtgactgcct ttacctccag tgccaggaag    600
caaacggaag tgttggaatt gggcgctcac cacatactag attccaccaa tccagaggcg    660
atcgccagtg cggaaggcaa atttgactat attatctcca ctgtgaacct gaagcttgac    720
tggaacttat acatcagcac cctggcgccc cagggacatt tccactttgt tggggtggtg    780
ttggagcctt tggatctaaa tcttttcccc cttttgatgg gacaacgctc cgtttctgcc    840
tccccagtgg gtagtcccgc caccattgcc accatgttgg actttgctgt gcgccatgac    900
attaaacccg tggtggaaca atttagcttt gatcagatca cgaggcgat cgcccatcta     960 gaaagcggca agcccattga tcgggtagtg ctcagccata gtaaaaatta g             1011
```

<210> SEQ ID NO 45
<211> LENGTH: 336
<212> TYPE: PRT
<213> ORGANISM: Synechocystis sp. 6803

<400> SEQUENCE: 45

```
Met Ile Lys Ala Tyr Ala Ala Leu Glu Ala Asn Gly Lys Leu Gln Pro
1               5                   10                  15

Phe Glu Tyr Asp Pro Gly Ala Leu Gly Ala Asn Glu Val Glu Ile Glu
            20                  25                  30

Val Gln Tyr Cys Gly Val Cys His Ser Asp Leu Ser Met Ile Asn Asn
        35                  40                  45

Glu Trp Gly Ile Ser Asn Tyr Pro Leu Val Pro Gly His Glu Val Val
    50                  55                  60

Gly Thr Val Ala Ala Met Gly Glu Gly Val Asn His Val Glu Val Gly
65                  70                  75                  80

Asp Leu Val Gly Leu Gly Trp His Ser Gly Tyr Cys Met Thr Cys His
                85                  90                  95

Ser Cys Leu Ser Gly Tyr His Asn Leu Cys Ala Thr Ala Glu Ser Thr
            100                 105                 110

Ile Val Gly His Tyr Gly Gly Phe Gly Asp Arg Val Arg Ala Lys Gly
        115                 120                 125

Val Ser Val Val Lys Leu Pro Lys Gly Ile Asp Leu Ala Ser Ala Gly
    130                 135                 140

Pro Leu Phe Cys Gly Gly Ile Thr Val Phe Ser Pro Met Val Glu Leu
145                 150                 155                 160

Ser Leu Lys Pro Thr Ala Lys Val Ala Val Ile Gly Ile Gly Gly Leu
                165                 170                 175

Gly His Leu Ala Val Gln Phe Leu Arg Ala Trp Gly Cys Glu Val Thr
            180                 185                 190

Ala Phe Thr Ser Ser Ala Arg Lys Gln Thr Glu Val Leu Glu Leu Gly
        195                 200                 205
```

Ala His His Ile Leu Asp Ser Thr Asn Pro Glu Ala Ile Ser Ala
    210                 215                 220

Glu Gly Lys Phe Asp Tyr Ile Ile Ser Thr Val Asn Leu Lys Leu Asp
225                 230                 235                 240

Trp Asn Leu Tyr Ile Ser Thr Leu Ala Pro Gln Gly His Phe His Phe
                245                 250                 255

Val Gly Val Val Leu Glu Pro Leu Asp Leu Asn Leu Phe Pro Leu Leu
            260                 265                 270

Met Gly Gln Arg Ser Val Ser Ala Ser Pro Val Gly Ser Pro Ala Thr
        275                 280                 285

Ile Ala Thr Met Leu Asp Phe Ala Val Arg His Asp Ile Lys Pro Val
290                 295                 300

Val Glu Gln Phe Ser Phe Asp Gln Ile Asn Glu Ala Ile Ala His Leu
305                 310                 315                 320

Glu Ser Gly Lys Ala His Tyr Arg Val Val Leu Ser His Ser Lys Asn
                325                 330                 335

<210> SEQ ID NO 46
<211> LENGTH: 1011
<212> TYPE: DNA
<213> ORGANISM: Artificial sequence
<220> FEATURE:
<223> OTHER INFORMATION: Codon optimized version of ADH gene originally
      from Synechocystis PCC 6803

<400> SEQUENCE: 46
atgattaagg cttatgctgc attagaagct aatggtaaat acaaccttt tgaatacgat        60 cccggtgctt taggtgcaaa tgaagtagaa attgaggttc agtattgtgg tgtatgtcat       120
tctgatttat ctatgattaa caacgaatgg ggaatttcca attatccctt agttcctgga       180
cacgaagttg ttggtactgt agcagctatg ggagaaggag ttaatcatgt tgaagtaggt       240
gacttagtag tttgggatg gcattctggt tactgtatga cctgtcatag ttgtttatct       300
ggttatcaca acttatgtgc aactgctgaa agtaccattg ttggtcatta cggtggtttt       360
ggtgatagag taagagctaa aggagttagt gttgttaaat taccaaaagg tatcgactta       420
gcaagtgcag gtcctctctt ttgtggggt attactgttt ttagtcctat ggttgaatta       480
agtttaaagc aactgcaaa agtagccgtc attggtattg gaggattggg acacttagct       540
gttcaatttc tccgtgcatg gggatgtgaa gttactgcct tacttctag tgctcgtaaa       600 caaaccgagg tattagaatt aggagcacac catatcttag attccaccaa ccctgaagct       660
atcgctagtg cagagggaaa attcgattat attattagta ctgttaattt gaaattagat       720
tggaacctct acatctctac tttagctccc caaggtcatt ttcactttgt tggagttgta       780
ttagaacccc tcgatttaaa cttattccct ttattaatgg gacaacgttc tgttagtgca       840
tctcctgttg gatctcccgc tactattgct accatgttag attttgcagt acgtcacgat       900
attaaacctg tagtagaaca attctctttc gatcaaatca cgaagctat tgctcattta       960 gaaagtggta aggctcatta ccgtgttgtt ttatctcact ctaaaaacta a              1011

<210> SEQ ID NO 47
<211> LENGTH: 336
<212> TYPE: PRT
<213> ORGANISM: Synechocystis sp. 6803

<400> SEQUENCE: 47

Met Ile Lys Ala Tyr Ala Ala Leu Glu Ala Asn Gly Lys Leu Gln Pro
1               5                   10                  15

```
Phe Glu Tyr Asp Pro Gly Ala Leu Gly Ala Asn Glu Val Glu Ile Glu
             20                  25                  30
Val Gln Tyr Cys Gly Val Cys His Ser Asp Leu Ser Met Ile Asn Asn
         35                  40                  45
Glu Trp Gly Ile Ser Asn Tyr Pro Leu Val Pro Gly His Glu Val Val
 50                  55                  60
Gly Thr Val Ala Ala Met Gly Glu Gly Val Asn His Val Glu Val Gly
 65                  70                  75                  80
Asp Leu Val Gly Leu Gly Trp His Ser Gly Tyr Cys Met Thr Cys His
                 85                  90                  95
Ser Cys Leu Ser Gly Tyr His Asn Leu Cys Ala Thr Ala Glu Ser Thr
                100                 105                 110
Ile Val Gly His Tyr Gly Gly Phe Gly Asp Arg Val Arg Ala Lys Gly
             115                 120                 125
Val Ser Val Val Lys Leu Pro Lys Gly Ile Asp Leu Ala Ser Ala Gly
130                 135                 140
Pro Leu Phe Cys Gly Gly Ile Thr Val Phe Ser Pro Met Val Glu Leu
145                 150                 155                 160
Ser Leu Lys Pro Thr Ala Lys Val Ala Val Ile Gly Ile Gly Gly Leu
                165                 170                 175
Gly His Leu Ala Val Gln Phe Leu Arg Ala Trp Gly Cys Glu Val Thr
             180                 185                 190
Ala Phe Thr Ser Ser Ala Arg Lys Gln Thr Glu Val Leu Glu Leu Gly
         195                 200                 205
Ala His His Ile Leu Asp Ser Thr Asn Pro Glu Ala Ile Ala Ser Ala
 210                 215                 220
Glu Gly Lys Phe Asp Tyr Ile Ile Ser Thr Val Asn Leu Lys Leu Asp
225                 230                 235                 240
Trp Asn Leu Tyr Ile Ser Thr Leu Ala Pro Gln Gly His Phe His Phe
                245                 250                 255
Val Gly Val Val Leu Glu Pro Leu Asp Leu Asn Leu Phe Pro Leu Leu
             260                 265                 270
Met Gly Gln Arg Ser Val Ser Ala Ser Pro Val Gly Ser Pro Ala Thr
         275                 280                 285
Ile Ala Thr Met Leu Asp Phe Ala Val Arg His Asp Ile Lys Pro Val
 290                 295                 300
Val Glu Gln Phe Ser Phe Asp Gln Ile Asn Glu Ala Ile Ala His Leu
305                 310                 315                 320
Glu Ser Gly Lys Ala His Tyr Arg Val Val Leu Ser His Ser Lys Asn
                325                 330                 335

<210> SEQ ID NO 48
<211> LENGTH: 1474
<212> TYPE: DNA
<213> ORGANISM: Cyanobacterium sp. ABICyano1

<400> SEQUENCE: 48
agagtttgat cctggctcag gatgaacgct ggcggtatgc ctaacacatg caagtcgaac      60
ggtctcttcg agatagtggc ggacgggtga aggaacgcgt gagaacctgc ctcaaggtcg     120
gggacaacag ttggaaacga ctgctaatac cggatgagcc gaataggtaa agatttatc     180 gcctagagag gggctcgcgt ctgattagct agatggtgag gtaaaggctt accatggcga     240
cgatcagtag ctggtctgag aggatgagca gccacactgg gactgagaca cggcccagac     300
```

| | |
|---|---:|
| tcctacggga ggcagcagtg gggaattttc gcaatgggc gaaagcctga cggagcaata | 360 |
| ccgcgtgagg gaggaaggct cttgggttgt aaacctcaaa acttagggaa gaaaaaaatg | 420 |
| acggtaccta atgtaagcat cggctaactc cgtgccagca gccgcggtaa tacggaggat | 480 |
| gcaagcgtta tccggaatca ttgggcgtaa agagtccgta ggtggcactt caagtctgct | 540 |
| ttcaaagacc gaagctcaac ttcggaaagg gagtggaaac tgaagagcta gagtatagta | 600 |
| ggggtagagg gaattcctag tgtagcggtg aaatgcgtag agattaggaa gaacaccagt | 660 |
| ggcgaaggcg ctctactggg catatactga cactgaggga cgaaagctag gggagcgaaa | 720 |
| gggattagat accccctgtag tcctagcggt aaacgatgga tactaggcgt agtgctgtta | 780 |
| gaaggactgt gccgaagcta acgcgttaag tatcccgcct ggggagtacg cacgcaagtg | 840 |
| tgaaactcaa aggaattgac ggggacccgc acaagcggtg gagtatgtgg tttaattcga | 900 |
| tgcaacgcga agaaccttac caaggcttga catcctgcga atcttggaga aatctgagag | 960 |
| tgcctaaggg aacgcagaga caggtggtgc atggctgtcg tcagctcgtg tcgtgagatg | 1020 |
| ttgggttaag tcccgcaacg agcgcaaccc tcgtccttag ttgccagcat taagttgggg | 1080 |
| actctaggga gaccgccggg gagaactcgg aggaaggtgg ggatgacgtc aagtcagcat | 1140 |
| gccccttacg tcttgggcta cacacgtact acaatggttg gacaaaggg gagcgaaacc | 1200 |
| gcgaggtgga gcgaatctca tcaaacccag ccacagttca gattgcaggc tgaaactcgc | 1260 |
| ctgcatgaag aggaatcgc tagtaatcgc aggtcagcat actgcggtga atccgttccc | 1320 |
| gggtcttgta cacaccgccc gtcacaccat ggaagttggt cacgcccgaa gtcgttattc | 1380 |
| taacccaagt ggaaggagac gccgaaggtg ggactagtga ctggggtgaa gtcgtaacaa | 1440 |
| ggtagccgta ccggaaggtg tggctggatc acct | 1474 |

<210> SEQ ID NO 49
<211> LENGTH: 1474
<212> TYPE: DNA
<213> ORGANISM: Cyanobacterium sp. ABICyano2

<400> SEQUENCE: 49

| | |
|---|---:|
| agagtttgat cctggctcag gatgaacgct ggcggtatgc ctaacacatg caagtcgaac | 60 |
| gggctcttcg gagctagtgg cggacgggtg aggaacgcgt gagaacctgc ctcaaggtcg | 120 |
| gggacaacag ttgaaaacga ctgctaatac cggatgagcc gaataggtaa agatttatc | 180 |
| gccttgagag gggctcgcgt ctgattagct agatggtgag gtaaaggctt accatggcga | 240 |
| cgatcagtag ctggtctgag aggatgagca gccacactgg gactgagaca cggcccagac | 300 |
| tcctacggga ggcagcagtg gggaattttc cgcaatgggc gaaagcctga cggagcaata | 360 |
| ccgcgtgagg gaggaaggct cttgggttgt aaacctcaaa acttagggaa gaaaaaaatg | 420 |
| acggtaccta atgtaagcat cggctaactc cgtgccagca gccgcggtaa tacggaggat | 480 |
| gcaagcgtta tccggaatca ttgggcgtaa agagtccgta ggtggcactt caagtctgct | 540 |
| ttcaaagacc gaagctcaac ttcggaaagg gagtggaaac tgaagagcta gagtatagta | 600 |
| ggggtagagg gaattcctag tgtagcggtg aaatgcgtag agattaggaa gaacaccagt | 660 |
| ggcgaaggcg ctctactggg catatactga cactgaggga cgaaagctag gggagcgaaa | 720 |
| gggattagat accccctgtag tcctagcggt aaacgatgga tactaggcgt agtgctgtaa | 780 |
| aagggactgt gccgaagcta acgcgttaag tatcccgcct ggggagtacg cacgcaagtg | 840 |
| tgaaactcaa aggaattgac ggggacccgc acaagcggtg gagtatgtgg tttaattcga | 900 |
| tgcaacgcga agaaccttac caaggcttga catcctgcga atcttgatga aagttgagag | 960 |

```
tgcctaaggg aacgcagaga caggtggtgc atggctgtcg tcagctcgtg tcgtgagatg    1020
ttgggttaag tcccgcaacg agcgcaaccc tcgtccttag ttgccagcat taagttgggg    1080
actctaggga gaccgccggg gagaactcgg aggaaggtgg ggatgacgtc aagtcagcat    1140
gccccttacg tcttgggcta cacacgtact acaatggttg ggacaaaggg gagcgaagcc    1200
gcgaggtgga gcgaatctca tcaaacccag ccacagttca gattgcaggc tgaaactcgc    1260
ctgcatgaag gaggaatcgc tagtaatcgc aggtcagcat actgcggtga atccgttccc    1320
gggtcttgta cacaccgccc gtcacaccat ggaagttggt cacgcccgaa gtcgttattc    1380
taacccaagt ggaaggagac gccgaaggtg ggactagtga ctggggtgaa gtcgtaacaa    1440
ggtagccgta ccggaaggtg tggctggatc acct                                1474

<210> SEQ ID NO 50
<211> LENGTH: 45
<212> TYPE: DNA
<213> ORGANISM: Artificial Sequence
<220> FEATURE:
<223> OTHER INFORMATION: PCR primer

<400> SEQUENCE: 50
tagttctaga agccctctta accactgaaa tattaattag tttgt                     45

<210> SEQ ID NO 51
<211> LENGTH: 47
<212> TYPE: DNA
<213> ORGANISM: Artificial Sequence
<220> FEATURE:
<223> OTHER INFORMATION: PCR primer

<400> SEQUENCE: 51
tgattctaga agggctaatt tggctatttc ttattaagaa taaatca                   47

<210> SEQ ID NO 52
<211> LENGTH: 19
<212> TYPE: DNA
<213> ORGANISM: Artificial Sequence
<220> FEATURE:
<223> OTHER INFORMATION: PCR primer

<400> SEQUENCE: 52
agctttacaa aactctcat                                                  19

<210> SEQ ID NO 53
<211> LENGTH: 23
<212> TYPE: DNA
<213> ORGANISM: Artificial Sequence
<220> FEATURE:
<223> OTHER INFORMATION: PCR primer

<400> SEQUENCE: 53
acgggttgat attgggcggg taa                                             23

<210> SEQ ID NO 54
<211> LENGTH: 24
<212> TYPE: DNA
<213> ORGANISM: Artificial Sequence
<220> FEATURE:
<223> OTHER INFORMATION: PCR primer

<400> SEQUENCE: 54
tttatttacc caagatgaac tcca                                            24
```

<210> SEQ ID NO 55
<211> LENGTH: 24
<212> TYPE: DNA
<213> ORGANISM: Artificial Sequence
<220> FEATURE:
<223> OTHER INFORMATION: PCR primer

<400> SEQUENCE: 55
gtactatcaa caggttgaac tgct                                              24

<210> SEQ ID NO 56
<211> LENGTH: 28
<212> TYPE: DNA
<213> ORGANISM: Artificial Sequence
<220> FEATURE:
<223> OTHER INFORMATION: PCR primer

<400> SEQUENCE: 56
tgggcataag tttagtgttt ctggtgaa                                          28

<210> SEQ ID NO 57
<211> LENGTH: 25
<212> TYPE: DNA
<213> ORGANISM: Artificial Sequence
<220> FEATURE:
<223> OTHER INFORMATION: PCR primer

<400> SEQUENCE: 57
accatgtgtt attccagcgg cagta                                             25

<210> SEQ ID NO 58
<211> LENGTH: 29
<212> TYPE: DNA
<213> ORGANISM: Artificial Sequence
<220> FEATURE:
<223> OTHER INFORMATION: PCR Primer

<400> SEQUENCE: 58
ccgtcgacga aaggggaac agggaaaag                                          29

<210> SEQ ID NO 59
<211> LENGTH: 31
<212> TYPE: DNA
<213> ORGANISM: Artificial Sequence
<220> FEATURE:
<223> OTHER INFORMATION: PCR primer

<400> SEQUENCE: 59
ccgaattcat tgtgttttt tatttttaca g                                       31

<210> SEQ ID NO 60
<211> LENGTH: 26
<212> TYPE: DNA
<213> ORGANISM: Artificial Sequence
<220> FEATURE:
<223> OTHER INFORMATION: PCR primer

<400> SEQUENCE: 60
tgccgtcaaa aggtaaagga atagat                                            26

<210> SEQ ID NO 61
<211> LENGTH: 24
<212> TYPE: DNA
<213> ORGANISM: Artificial Sequence
<220> FEATURE:
<223> OTHER INFORMATION: PCR primer

```
<400> SEQUENCE: 61
gtctcaagcc aaatgccgtg cgat                                          24

<210> SEQ ID NO 62
<211> LENGTH: 27
<212> TYPE: DNA
<213> ORGANISM: Artificial Sequence
<220> FEATURE:
<223> OTHER INFORMATION: PCR primer

<400> SEQUENCE: 62
tcaaccaagg gtttttaacc tccgcaa                                       27

<210> SEQ ID NO 63
<211> LENGTH: 31
<212> TYPE: DNA
<213> ORGANISM: Artificial Sequence
<220> FEATURE:
<223> OTHER INFORMATION: PCR primer

<400> SEQUENCE: 63
gcagggttct cctcgctcga caatgaacta t                                  31

<210> SEQ ID NO 64
<211> LENGTH: 25
<212> TYPE: DNA
<213> ORGANISM: Artificial Sequence
<220> FEATURE:
<223> OTHER INFORMATION: PCR primer

<400> SEQUENCE: 64
gtattgtggg gtgtgccaca gtgat                                         25

<210> SEQ ID NO 65
<211> LENGTH: 23
<212> TYPE: DNA
<213> ORGANISM: Artificial Sequence
<220> FEATURE:
<223> OTHER INFORMATION: PCR primer

<400> SEQUENCE: 65
aatgccgatc actgccactt ttg                                           23

<210> SEQ ID NO 66
<211> LENGTH: 20
<212> TYPE: DNA
<213> ORGANISM: Artificial Sequence
<220> FEATURE:
<223> OTHER INFORMATION: PCR primer

<400> SEQUENCE: 66
agtggattct tggcagaacg                                               20

<210> SEQ ID NO 67
<211> LENGTH: 29
<212> TYPE: DNA
<213> ORGANISM: Artificial Sequence
<220> FEATURE:
<223> OTHER INFORMATION: PCR primer

<400> SEQUENCE: 67
cagcagtgaa aatagcgtat acattgcaa                                     29

<210> SEQ ID NO 68
```

<211> LENGTH: 7094
<212> TYPE: DNA
<213> ORGANISM: Artificial Sequence
<220> FEATURE:
<223> OTHER INFORMATION: Synthetically created cassette sequence for
      ethanol production

<400> SEQUENCE: 68

| | | | | | |
|---|---|---|---|---|---|
| aattaaaagt | ataaaaattt | taacggttct | cggtttgatt | attttccgaa | aaaccgataa | 60 |
| aataactcaa | atattcaac | aagaataacc | caaaaaactt | atttgaaaca | taagtataat | 120 |
| aaaaggttat | tacataatta | tatgttaacc | gaccaatcga | ccaaaagtaa | agttaataca | 180 |
| gaattaccag | aaaaagctaa | gaccgttgta | agtaagacac | ggtcgaacct | aacaagccct | 240 |
| tctgaagtac | ggatagaccc | ctctaggtat | taccccgaag | gtgttgagat | cgtccctgaa | 300 |
| cttttgatga | ttccaaccaa | gggcgctatc | gagcgtaatt | ttgattggtt | tactttcgtt | 360 |
| gggagaaagg | tgacgaggga | gaactttgat | tctattattg | atggattttg | tggcggcggc | 420 |
| ttctgggaca | ttgaaacgga | aattgatacg | actgtttatg | acgctaattt | ttcccttttat | 480 |
| aggggcggtg | aaaagtatga | tttatggtgg | actaattcac | taggaattaa | gatagcatct | 540 |
| aggaaaaatg | aagaattaga | tattgaggga | aaattaagct | atgaaagcta | tgatttaatc | 600 |
| attacttta | gtggtagcac | tttacaacaa | ctttatggat | ttaataaccct | tttgagtcaa | 660 |
| tgtgcgttgg | tatatcgtgc | atatcagtta | ggttatatt | taactagaat | agattttgcc | 720 |
| gttacagatt | attccaagac | cttgaatgta | tttgatgtca | aactagcatt | attaaaaggt | 780 |
| aattttagag | gatttaagag | taaaggtact | aatgaaagtg | gtacacgaaa | gattgatggg | 840 |
| ataactaact | attgtggtag | tcgtgaatct | gagtcaatgg | taagaatata | tgattgtttt | 900 |
| aaaaaacatg | gaataatagc | cactagatta | gagaatgaat | tgaagggaga | taaagcgaaa | 960 |
| aagataggta | atgaactgtg | taaactttat | cggagttttg | aagaaaaagt | gcacatgtgc | 1020 |
| aatgaagact | caacgcatgg | atgcaataaa | actaagtcaa | aaatcagaaa | aactaaagca | 1080 |
| catcataatc | aggtattagc | aagatatttt | gatagtgtaa | ttacttcaag | tattgatttt | 1140 |
| attgatagga | gtaaaaagtg | gaaaatgga | agtttaaaac | actgtaaaag | attatcatgg | 1200 |
| tgggaaaagt | tcagggaaaa | attatcatct | agtttgatga | aaattaagct | cacaaatcct | 1260 |
| tttaaaaagc | ctagtttagc | tgataatgct | aaatggttaa | tcagacaagt | taagggaaca | 1320 |
| attagtaagt | taaaaatgg | attatgtgat | tttgactta | atcaattaat | ggaattatta | 1380 |
| aagcaattag | atgatgatag | acccaaacct | aaaggtatcc | aagaagaaaa | ggaattagcg | 1440 |
| attaagatat | taaagaaaca | aggaattaac | gctttattta | cccaagatga | actccaagaa | 1500 |
| tttaagaaa | gatttggaat | agaatttgat | aaaacaaatc | ctcatggaac | tatctttgag | 1560 |
| tatgataatt | attttggtga | taagttcagt | aatgatttaa | ccattggtga | tagagtaaaa | 1620 |
| ttcatttag | ggggtatttg | gttaatggga | actattaaga | agataaataa | aacaggttta | 1680 |
| gaaacagaaa | attatgacgt | taactttgat | gatggcgggt | tttatagtgg | tataattcca | 1740 |
| gataatatat | ttaggcttaa | gagtagttaa | aaagcgaaac | gtgtttcgta | tttgtattta | 1800 |
| ataagtctaa | aaaagtctga | tttaagttgt | ttaattaggt | catcacgctg | gcgtagctaa | 1860 |
| accttagatg | gaataaggtc | aaaaacatac | tacaagacct | gatcgcaatt | agtaaataaa | 1920 |
| tgatttattc | ttaataagaa | atagccaaat | tagcccttct | agacctagga | cagctgtctc | 1980 |
| ttatacacat | ctcaaatgca | ttgatcagca | gttcaacctg | ttgatagtac | gtactaagct | 2040 |
| ctcatgtttc | acgtactaag | ctctcatgtt | taacgtacta | agctctcatg | tttaacgaac | 2100 |

```
taaaccctca tggctaacgt actaagctct catggctaac gtactaagct ctcatgtttc    2160
acgtactaag ctctcatgtt tgaacaataa aattaatata aatcagcaac ttaaatagcc    2220
tctaaggttt taagttttat aagaaaaaaa agaatatata aggcttttaa accttttcga    2280
accgtacgta ggtcgacaat taataacttc ttcctgtacg ggcgaatggc catttgctcc    2340
taactaactc cgtactgctt tgcggaacga gcgtagcgaa ctctccgaat tactaagcct    2400
tcatccctga tagatgcaaa aaacgaatta aaattatgtg taaaagaaa atgtgtcttt    2460 atttagtagt caaagttaca aaatattaag aatcaaatta ataatgtatt gggcagttaa    2520
gtatataagt cttaaatat ttatttgtat tcaatatatt aaccgaggac aaattatgaa    2580
ttcttacact gttggaacct atttagcaga acgtttagtt caaattggtc tcaaacacca    2640
ttttgcagta gctggtgatt ataatttagt tttattggat aacttattgt taaataagaa    2700
tatggaacaa gtgtattgtt gtaatgaatt aaactgtggt ttttctgctg agggatatgc    2760
tcgtgcaaaa ggtgctgccg cagcagttgt tacttattct gttggagcat taagtgcttt    2820
tgacgctatt ggaggtgctt atgcagaaaa tttacctgta atcttaatct ctggtgcacc    2880
caataacaac gatcacgctg ctggtcatgt attgcatcat gctttaggta aaaccgatta    2940
tcattaccaa ttagaaatgg caaaaaatat taccgctgcc gcagaagcta tttatactcc    3000
cgaagaagca cctgctaaga tcgatcacgt aattaaaacc gctctccgtg agaaaaaacc    3060
cgtatattta gaaatcgctt gcaatatcgc ttctatgcct tgtgcagctc ctggacctgc    3120
tagtgcttta tttaacgatg aagcatctga tgaggctagt ttaaatgccg ctgttgaaga    3180
aactttgaaa tttattgcta atcgtgataa agtagctgtt ttagttggtt ctaaactccg    3240
tgccgctggt gcagaagaag cggctgtaaa attcgcagat gccttaggag gtgctgttgc    3300
cacaatggca gccgctaaaa gttttttccc cgaagaaaat cctcattaca ttggtacttc    3360
ttggggtgag gtatcttacc ctggtgtaga aaaaaccatg aaggaagctg atgcagtaat    3420
tgcattagct cctgttttca atgattactc taccactggt tggactgata ttccagaccc    3480
caaaaaatta gttttagcag aacctcgctc tgtagttgtg aatggtgtta gatttcccag    3540
tgtacatctc aaagattatt taactcgttt agctcaaaaa gtgagtaaaa agactggcgc    3600
actcgatttc tttaaatctt taaatgctgg tgaattaaag aaagcagctc ctgctgatcc    3660
cagtgctcct ttagtgaatg ccgaaatcgc aagacaagtt gaagccttgt taactcctaa    3720
cactaccgtt attgccgaga ctggtgatag ttggttcaat gctcaacgca tgaaattacc    3780
caatggtgct cgtgttgagt atgaaatgca atggggtcac attggatggt ctgttcctgc    3840
tgcatttgga tatgcagttg gagcacctga gcgtagaaac attttaatgg taggtgatgg    3900 ttcttttccaa ctcactgctc aagaagttgc acaaatggta cgtttaaaat tgcctgttat    3960
tatctttctc attaacaact atggttacac cattgaagtt atgattcatg atggtcctta    4020
taataacatt aagaattggg attacgcagg tttaatggag gtatttaacg gtaatggtgg    4080
atacgacagt ggagcaggta aaggattaaa agctaaaaca ggaggtgagt tagctgaagc    4140
aattaaagta gctttagcca atacagatgg tcctacctta atcgaatgtt tcattggacg    4200
tgaagattgt actgaagagt tagttaaatg gggaaagcgt gttgccgctg caaattctcg    4260
taaacctgta aacaaactct tgtagttagg atccgagctc actagtacat aattaggaga    4320
aattaataca tatgattaag gcttatgctg cattagaagc taatggtaaa ttacaacctt    4380
ttgaatacga tcccggtgct ttaggtgcaa atgaagtaga aattgaggtt cagtattgtg    4440
gtgtatgtca ttctgattta tctatgatta acaacgaatg gggaatttcc aattatcct    4500
```

```
tagttcctgg acacgaagtt gttggtactg tagcagctat gggagaagga gttaatcatg   4560
ttgaagtagg tgacttagta ggtttgggat ggcattctgg ttactgtatg acctgtcata   4620
gttgtttatc tggttatcac aacttatgtg caactgctga aagtaccatt gttggtcatt   4680
acggtggttt tggtgataga gtaagagcta aaggagttag tgttgttaaa ttaccaaaag   4740
gtatcgactt agcaagtgca ggtcctctct tttgtggggg tattactgtt tttagtccta   4800
tggttgaatt aagtttaaag ccaactgcaa agtagccgt cattggtatt ggaggattgg   4860
gacacttagc tgttcaattt ctccgtgcat ggggatgtga agttactgcc tttacttcta   4920
gtgctcgtaa acaaaccgag gtattagaat taggagcaca ccatatctta gattccacca   4980
accctgaagc tatcgctagt gcagagggaa aattcgatta tattattagt actgttaatt   5040
tgaaattaga ttggaacctc tacatctcta ctttagctcc ccaaggtcat tttcactttg   5100
ttggagttgt attagaaccc ctcgatttaa acttattccc tttattaatg ggacaacgtt   5160
ctgttagtgc atctcctgtt ggatctcccg ctactattgc taccatgtta gattttgcag   5220
tacgtcacga tattaaacct gtagtagaac aattctcttt cgatcaaatc aacgaagcta   5280
ttgctcattt agaaagtggt aaggctcatt accgtgttgt tttatctcac tctaaaaact   5340
aactagatct ctgcagagaa tataaaaagc cagattatta atccggcttt tttattattt   5400
aaatactgtg cacgatatcc aattgcatgg aaaaaacgac aattacaaga aagtaaaact   5460
tatgtcatct atatgcttcg tgtatattaa cttcctgtta cagagcttta caaaactctc   5520
attaatcctt tagactaagt ttagtcagtt ccaatctgaa catcgacaaa tacataagga   5580
attataacca agcatgcaac gtgaagctgt tattgcagaa gtttctactc aattatctga   5640
agttgtaggt gttatcgaaa gacatttaga acccaccttg ttagcagtac atttgtacgg   5700
aagtgctgta gatggaggtc tcaaaccccca ttctgacatt gatttattgg ttacagtaac   5760
tgttcgtctc gacgaaacca cccgccgtgc tttgattaac gatttattag aaacaagtgc   5820
ctctccaggt gaatccgaaa tcttgagagc tgttgaggta acaatcgttg tacatgacga   5880
tattatccct tggcgttatc ccgctaagcg tgaattacaa tttggagaat ggcaacgtaa   5940 tgatattta gcaggtatct ttgaacctgc aactattgat attgacttag ctattttgtt   6000
aaccaaagct agagaacatt ctgttgcatt agtaggaccc gctgccgaag agttgtttga   6060
tcccgtacct gagcaagatt tatttgaagc tctcaacgaa actttaacct tatggaactc   6120
ccctcccgat tgggcaggtg atgaacgtaa cgttgtatta accttgtctc gcatttggta   6180
cagtgctgta actggtaaaa ttgcacctaa agacgttgcc gctgattggg caatggaaag   6240
attacccgcc caatatcaac ccgtaatttt agaagctcgt caagcctatt gggtcaaga   6300 ggaagataga ttagcttctc gtgcagatca attagaagaa tttgttcatt atgtgaaagg   6360
agaaatcaca aaagtagttg ggaaataaaa gcttccatgg cagcacgctt ggactcctgt   6420
tgatagatcc agtaatgacc tcagaactcc atctggattt gttcagaacg ctcggttgcc   6480
gccgggcgtt ttttattggt gagaatccaa gcactgctag cttgagatgt gtataagaga   6540
cagctgttct agaagccctc ttaaccactg aaatattaat tagtttgtga gaaagtttcg   6600
tgtcaagagt gtaacggaat aaagtttttt cggttattaa ctaagatatg aacttattat   6660
tattgttccg aaaaaagttt atgcagtctc ttgacatgaa atgaacaaac gtataatcac   6720
attacaaggg ctagggcgat gtttaagcga agtgataaaa ccaaaccttaa agattcaat   6780 ttgagggtgt tcaggagtga tttaagactt gtaaattaat ttcaacccta tgaggattga   6840
```

```
actagaccca taaaccccaa ataagagcaa ataccatca gcacagcttc cgtacctacc    6900
tcgcttataa accgctttt ctttactttt tcatcggctt aacattctta cgactcctat    6960
aggagttgta gagttcttaa acaattacta aacaattaat attttttcgt taaagtcgat    7020
ggttatggtt gtgtcagaat gcacattagt gttgggttag tgtggcggac atcattatga    7080
tctccactaa atac                                                      7094
```

<210> SEQ ID NO 69
<211> LENGTH: 327
<212> TYPE: DNA
<213> ORGANISM: Cynobacterium sp. ABICyano1

<400> SEQUENCE: 69

```
tgagaaaaag tgtaaacaaa tattaagaaa aagatcagaa aaatttaaca acacgtaata     60
aaaaaatgcg tcactacggg ttataaattt acatgaaagg ttaaaacact tttctgagac    120
gattttgata aaaagttgt caaaaaatta agtttcttta caaatgctta acaaaaactt    180
ggttttaagc acaaaataag agagactaat ttgcagaagt tttacaagga aatcttgaag    240
aaaaagatct aagtaaaacg actctgttta accaaaattt aacaaattta acaaaacaaa    300
ctaaatctat taggagatta actaagc                                         327
```

<210> SEQ ID NO 70
<211> LENGTH: 574
<212> TYPE: DNA
<213> ORGANISM: Artificial Sequence
<220> FEATURE:
<223> OTHER INFORMATION: Plasmid Vector

<400> SEQUENCE: 70

```
tctagaccta ggacagctgt ctcttataca catctcaaat gctgatcagc agttcaacct     60
gttgatagta cgtactaagc tctcatgttt cacgtactaa gctctcatgt ttaacgtact    120
aagctctcat gtttaacgaa ctaaaccctc atggctaacg tactaagctc tcatggctaa    180
cgtactaagc tctcatgttt cacgtactaa gctctcatgt ttgaacaata aaattaatat    240
aaatcagcaa cttaaatagc ctctaaggtt ttaagtttta taagaaaaaa aagaatatat    300
aaggctttta aagttcgaac cgtacgggtc gacgaattcg gatccgagct cactagtcat    360
atgagatctc tgcagactgt gcacgatatc caattggcat gcaagcttcc atggcagcac    420
gcttggactc ctgttgatag atccagtaat gacctcagaa ctccatctgg atttgttcag    480
aacgctcggt tgccgccggg cgttttttat tggtgagaat ccaagcactg ctagcttgag    540
atgtgtataa gagacagctg tctctagacc tagg                                574
```

<210> SEQ ID NO 71
<211> LENGTH: 20
<212> TYPE: DNA
<213> ORGANISM: Artificial Sequence
<220> FEATURE:
<223> OTHER INFORMATION: PCR primer

<400> SEQUENCE: 71

```
gtgcagctcc tggacctgct                                                 20
```

<210> SEQ ID NO 72
<211> LENGTH: 24
<212> TYPE: DNA
<213> ORGANISM: Artificial Sequence
<220> FEATURE:
<223> OTHER INFORMATION: PCR primer

```
<400> SEQUENCE: 72
gaattttccc tctgcactag cgat                                          24

<210> SEQ ID NO 73
<211> LENGTH: 26
<212> TYPE: DNA
<213> ORGANISM: Artificial Sequence
<220> FEATURE:
<223> OTHER INFORMATION: PCR primer

<400> SEQUENCE: 73
accgtacggg tcgacaatta ataact                                        26

<210> SEQ ID NO 74
<211> LENGTH: 22
<212> TYPE: DNA
<213> ORGANISM: Artificial Sequence
<220> FEATURE:
<223> OTHER INFORMATION: PCR primer

<400> SEQUENCE: 74
aagaaatcga gtgcgccagt ct                                            22

<210> SEQ ID NO 75
<211> LENGTH: 30
<212> TYPE: DNA
<213> ORGANISM: Artificial Sequence
<220> FEATURE:
<223> OTHER INFORMATION: PCR primer

<400> SEQUENCE: 75
tagagtatga taaaatgaca aggaaaggat                                    30

<210> SEQ ID NO 76
<211> LENGTH: 22
<212> TYPE: DNA
<213> ORGANISM: Artificial Sequence
<220> FEATURE:
<223> OTHER INFORMATION: PCR primer

<400> SEQUENCE: 76
aagaaatcga gtgcgccagt ct                                            22

<210> SEQ ID NO 77
<211> LENGTH: 32
<212> TYPE: DNA
<213> ORGANISM: Artificial Sequence
<220> FEATURE:
<223> OTHER INFORMATION: PCR primer

<400> SEQUENCE: 77
gttgaggtat taatagagct tgataaatga ta                                 32

<210> SEQ ID NO 78
<211> LENGTH: 22
<212> TYPE: DNA
<213> ORGANISM: Artificial Sequence
<220> FEATURE:
<223> OTHER INFORMATION: PCR primer

<400> SEQUENCE: 78
aagaaatcga gtgcgccagt ct                                            22

<210> SEQ ID NO 79
```

```
<211> LENGTH: 28
<212> TYPE: DNA
<213> ORGANISM: Artificial Sequence
<220> FEATURE:
<223> OTHER INFORMATION: PCR primer

<400> SEQUENCE: 79
tgagaaaaag tgtaaacaaa tattaaga                                             28

<210> SEQ ID NO 80
<211> LENGTH: 22
<212> TYPE: DNA
<213> ORGANISM: Artificial Sequence
<220> FEATURE:
<223> OTHER INFORMATION: PCR primer

<400> SEQUENCE: 80
aagaaatcga gtgcgccagt ct                                                   22

<210> SEQ ID NO 81
<211> LENGTH: 1059
<212> TYPE: DNA
<213> ORGANISM: Escherichia coli

<400> SEQUENCE: 81
gtagaaaaga tcaaaggatc ttcttgagat cctttttttc tgcgcgtaat ctgctgcttg          60
caaacaaaaa aaccaccgct accagcggtg gtttgtttgc cggatcaaga gctaccaact         120 cttttttccga aggtaactgg cttcagcaga gcgcagatac caaatactgt ccttctagtg        180
tagccgtagt taggccacca cttcaagaac tctgtagcac cgcctacata cctcgctctg         240
ctaatcctgt taccagtggc tgctgccagt ggcgataagt cgtgtcttac cgggttggac         300
tcaagacgat agttaccgga taaggcgcag cggtcgggct gaacggggggg ttcgtgcaca        360 cagcccagct tggagcgaac gacctacacc gaactgagat acctacagcg tgagctatga         420
gaaagcgcca cgcttcccga agggagaaag cggacaggta tccggtaag cggcagggtc          480 ggaacaggag agcgcacgag ggagcttcca gggggaaacg cctggtatct ttatagtcct         540
gtcgggtttc gccacctctg acttgagcgt cgatttttgt gatgctcgtc aggggggcgg         600
agcctatgga aaaacgccag caacgcggcc ttttttacggt tcctggcctt ttgctggcct        660
tttgctcaca tgttctttcc tgcgttatcc cctgattctg tggataaccg tattaccgcc         720
tttgagtgag ctgataccgc tcgccgcagc cgaacgaccg agcgcagcga gtcagtgagc         780
gaggaagcgg aagagcgcct gatgcggtat tttctcctta cgcatctgtg cggtatttca         840
caccgcatat ggtgcactct cagtacaatc tgctctgatg ccgcatagtt aagccagtat         900
acactccgct atcgctacgt gactgggtca tggctgcgcc ccgacacccg ccaacacccg         960
ctgacgcgcc ctgacgggct tgtctgctcc cggcatccgc ttacagacaa gctgtgaccg        1020
tctccgggag ctgcatgtgt cagaggtttt caccgtcat                               1059

<210> SEQ ID NO 82
<211> LENGTH: 40
<212> TYPE: DNA
<213> ORGANISM: Cyanobacterium sp. ABICyano2

<400> SEQUENCE: 82
tttgaaacat aagtataata aaaggttatt acataattat                                40

<210> SEQ ID NO 83
<211> LENGTH: 451
```

```
<212> TYPE: DNA
<213> ORGANISM: Cyanobacterium sp. ABICyano2

<400> SEQUENCE: 83
gggtgttcag gagtgattta agacttgtaa attaatttca accctatgag gattgaacta      60
gacccataaa ccccaaataa gagcaaaata ccatcagcac agcttccgta cctacctcgc     120
ttataaaccg cttttctctt actttttcat cggcttaaca ttcttacgac tcctatagga    180
gttgtagagt tctaaacaa ttactaaaca attaatattt tttcgttaaa gtcgatggtt     240
atggttgtgt cagaatgcac attagtgttg ggttagtgtg gcggacatca ttatgatctc    300
cactaaatac aattaaaagt ataaaaattt taacggttct cggtttgatt attttccgaa    360
aaaccgataa aataactcaa aatattcaac aagaataacc caaaaaactt atttgaaaca    420
taagtataat aaaaggttat tacataatta t                                    451

<210> SEQ ID NO 84
<211> LENGTH: 30
<212> TYPE: DNA
<213> ORGANISM: Cyanobacterium sp. ABICyano2

<400> SEQUENCE: 84
aaagcgaaac gtgtttcgta tttgtattta                                      30

<210> SEQ ID NO 85
<211> LENGTH: 334
<212> TYPE: DNA
<213> ORGANISM: Cyanobacterium sp. ABICyano2

<400> SEQUENCE: 85
aaagcgaaac gtgtttcgta tttgtattta ataagtctaa aaagtctga tttaagttgt       60 ttaattaggt catcacgctg gcgtagctaa accttagatg gaataaggtc aaaaacatac    120
tacaagacct gatcgcaatt agtaaataaa tgatttattc ttaataagaa atagccaaat    180
tagccctagc cctcttaacc actgaaatat taattagttt gtgagaaagt ttcgtgtcaa    240
gagtgtaacg gaataaagtt ttttcggtta ttaactaaga tatgaactta ttattattgt    300
tccgaaaaaa gtttatgcag tctcttgaca tgaa                                  334

<210> SEQ ID NO 86
<211> LENGTH: 84
<212> TYPE: DNA
<213> ORGANISM: Cyanobacterium sp.

<400> SEQUENCE: 86
atgaacaaac gtataatcac attacaaggg ctagggcgat gtttaagcga agtgataaaa       60
ccaaaccttg aagattcaat ttga                                             84

<210> SEQ ID NO 87
<211> LENGTH: 27
<212> TYPE: PRT
<213> ORGANISM: Cyanobacterium sp.

<400> SEQUENCE: 87

Met Asn Lys Arg Ile Ile Thr Leu Gln Gly Leu Gly Arg Cys Leu Ser
1               5                   10                  15

Glu Val Ile Lys Pro Asn Leu Lys Asp Ser Ile
            20                  25
```

SHUTTLE VECTOR CAPABLE OF TRANSFORMING MULTIPLE GENERA OF CYANOBACTERIA

CROSS-REFERENCE TO RELATED APPLICATIONS

This application is a continuation of International Application No. PCT/US2013/077359, filed Dec. 22, 2013, which claims the benefit of U.S. Provisional Patent Application Ser. No. 61/740,709, filed Dec. 21, 2012, and U.S. Provisional Patent Application Ser. No. 61/835,007, filed Jun. 14, 2013, the disclosures of which are incorporated herein by reference.

REFERENCE TO SEQUENCE LISTING

This application contains a sequence listing comprising 87 sequences, submitted by EFS-Web, thereby satisfying the requirements of 37 C.F.R. §§1.821-1.825. The sequence listing file, named "Universal_vector_PCT_12_06_13_ST25", was created on Nov. 13, 2013, and is 101 kb in size.

STATEMENT REGARDING FEDERALLY SPONSORED RESEARCH

This invention was made in part with United States government support under the Department of Energy grant number DE-EE0002867. The government has certain rights in this invention.

FIELD OF THE INVENTION

The present invention relates to the genetic enhancement of Cyanobacteria. A novel vector is described which is capable of efficiently transforming a broad range of cyanobacterial species.

BACKGROUND OF THE INVENTION

Cyanobacteria can be modified to produce many types of secondary products, such as biofuels, pharmaceuticals, nutrients, carotenoids, etc. The use of cyanobacteria to produce these products can have several benefits. Cyanobacterial growth does not require the costly input of organic carbon, since cyanobacteria are capable of absorbing light and fixing carbon dioxide as a carbon source for autotrophic growth.

The transformation of the cyanobacterial genus *Synechococcus* with genes that encode enzymes that can produce ethanol for biofuel production has been described (U.S. Pat. Nos. 6,699,696 and 6,306,639, both to Woods et al.). The transformation of the cyanobacterial genus *Synechocystis* has been described, for example, in PCT/EP2009/000892, PCT/EP2009/060526, and in U.S. Patent Publication No. US2009/0155871. The cyanobacteria as a whole, however, are a very divergent group of organisms. Due to this diversity, it is often difficult to find a method to effectively and efficiently transform a given host cyanobacterial species. Further, it is also often difficult for the inserted DNA vehicle to replicate adequately once it is present in the host cyanobacterial cell.

Certain strains of cyanobacteria can be naturally transformed. Other cyanobacterial strains can be transformed, for example, by the use of conjugation or electroporation. For a review of cyanobacterial transformation methods, see Vioque, "Transformation of cyanobacteria," Adv. Exp. Med. Biol. 616:12-22 (2007); Elhai et al., "Conjugal transfer of DNA to cyanobacteria," Methods in Enzymology 167:747-754 (1988); and Vermaas, "Molecular genetics of the cyanobacterium *Synechocystis* sp. PCC 6803: Principles and possible biotechnology applications," Jour. Appl. Phycology 8:263-273 (1996).

One commonly used method of gene transfer to cyanobacteria involves the construction of vectors having a backbone derived from the broad-host range plasmid RSF1010. This plasmid has no cyanobacterial origin of replication, however. The RSF1010-based vector has been widely used as a conjugation vector for transforming bacteria, including cyanobacteria (Mermet-Bouvier et al. (1993) "Transfer and replication of RSF1010-derived plasmids in several cyanobacteria of the genera *Synechocystis* and *Synechococcus*" Current Microbiology 27:323-327).

Other vectors for transformation of cyanobacteria include the pDU1-based vectors. The pDU1 origin of replication is best suited for filamentous cyanobacteria, however. Attempts to transform certain species of cyanobacteria with either RSF1010 or pDU1-based shuttle vectors have been unsuccessful.

Several endogenous plasmids from *Synechococcus* sp. PCC 7002 have been utilized as a backbone plasmid to prepare vectors for heterologous gene expression (Xu et al., Photosynthesis Research Protocols 684:273-293; 2011).

A broad-host-range shuttle vector that replicates in *E. coli* and three different cyanobacterial strains was developed by Huang et al. Nucleic Acids Research 38:2577-2593 (2010). Expression of three fluorescent reporter proteins (Cerulean, GFPmut3B and EYFP) was demonstrated. Shuttle vectors capable of replication and selection in both *E. coli* and in the blue green algae *Anabaena* have been constructed (Wolk et al., PNAS 81:1561-1565 (1984)). Transformation of these vectors apparently requires the presence helper plasmids and a broad host-range plasmid RP-4. These vectors contain regions for replication and mobilization derived from plasmid pBR322, as well as the cyanobacterial replicon pDUI. Other types of vectors for cyanobacteria are described, for example, in Schmetterer et al., Gene, 62:101-109 (1988); Walton et al., Nucleic Acids Research, 21 (3) GenBank Accession No. M81382 (1993); Houmard et al., Methods in Enzymology 167:808-847 (1988).

What is needed in the field of genetically modified cyanobacteria is an easy to manipulate plasmid vector that can be used to express genes of interest in a host cyanobacterial cell, which is capable of being transformed efficiently to a broad range of cyanobacterial species.

SUMMARY OF THE INVENTION

In an aspect of the invention, a novel plasmid for transformation of genes of interest to cyanobacteria is provided. Genes, host cyanobacterial cells, and methods of producing compounds of interest in cyanobacteria are also provided.

In an aspect of the invention, a nucleic acid construct for expressing a recombinant gene in a cyanobacterium is provided, having a DNA origin of replication suitable for replication of the nucleic acid construct in cyanobacteria, along with a gene encoding a protein regulating replication of the nucleic acid construct in cyanobacteria by interacting with the DNA origin of replication, where the protein has an amino acid sequence having at least 80%, 85%, 90%, 95%, 97%, 99%, 99.5%, or more sequence identity to the cyanobacterial plasmid replication protein shown in SEQ ID NO: 3, and at least one recombinant gene selected from (i) a production gene encoding a biocatalyst for the production of a chemical compound, (ii) a marker gene able to indicate the presence of the nucleic acid construct in the cyanobacterium, and combinations thereof. The DNA origin of replication can have, for example, a nucleotide sequence having at least 80%, 85%, 90%, 95%, 98%, or more sequence identity to the cyanobacterial origin of plasmid replication shown in SEQ ID NO: 15. The production gene can be, for example, a biosynthetic pathway gene encoding an enzyme catalyzing a metabolic reaction which is not present in the wild-type cyanobacterium. The chemical compound can be chosen from, for example, alkanols, alkanes, alkenes, ethers, polyhydroxyalkanoates such as PHB, fatty acids, fatty acid esters, hydrogen, and their combinations. The chemical compound can be a biofuel, such as ethanol or another alcohol or alkanol. The production gene can be, for example, a gene encoding pyruvate dehydrogenase, a gene encoding alcohol dehydrogenase, and a gene encoding alcohol dehydrogenase E enzyme (AdhE), as well as combinations thereof. the nucleic acid construct can be a closed circular nucleic acid molecule. The *cyanobacterium* can be, for example, *Synechococcus* sp., *Synechocystis* sp., *Cyanobacterium* sp., or *Anabaena* sp. The marker gene can be, for example, a selectable marker (such as an antibiotic resistance gene or a gene conferring prototrophy to an auxotrophic *cyanobacterium*) or a screenable marker, such as a gene encoding a fluorescent protein. The construct can include, for example, a DNA origin of replication for replication of the nucleic acid construct in *Escherichia coli*, such as SEQ ID NO: 10. The construct can also have a DNA origin for conjugational transfer (oriVT), such as SEQ ID NO: 81, for transfer of the nucleic acid construct from a bacterial host to the *cyanobacterium*. The construct can also have a segment of DNA containing a plurality of restriction sites for restriction endonuclease enzymes, each of the plurality of restriction sites occurring only once within the nucleic acid construct, for inserting DNA into the nucleic acid construct. The construct can have a sequence having at least 50% identity to SEQ ID NO: 1. The recombinant gene can have altered codon triplets in comparison to a corresponding wild-type gene in order to enhance translation in the *cyanobacterium*.

In another aspect of the invention, a method for producing a chemical compound of interest with a cyanobacterial cell is provided, by introducing any of the above-described nucleic acid constructs into a cyanobacterial cell, culturing the cell, and obtaining the compound of interest. A headspace can be present above the culture, and the compound of interest can be obtained from the headspace. The cyanobacterial cell can be subjected to sunlight and $CO_2$.

In yet another aspect of the invention, a method of producing a metabolically enhanced cyanobacterial cell is provided, by introducing any of the above-described constructs to the cyanobacterial cell, and recovering the cell. The introducing step can occur, for example, by conjugal transformation or electroporation.

In another aspect of the invention, a metabolically enhanced cyanobacterial cell for the expression of a recombinant gene is provided, having a plasmid with a DNA origin of replication with a nucleotide sequence having at least 80%, 85%, 90%, 95%, 98%, or more sequence identity to SEQ ID NO: 15, and at least one recombinant gene selected from (i) a production gene encoding a biocatalyst for the production of a chemical compound, (ii) a marker gene able to indicate the presence of the nucleic acid construct in the *cyanobacterium*, and a gene encoding a protein regulating replication by interacting with the DNA origin of replication, the protein having an amino acid sequence having at least 80% sequence identity to SEQ ID NO: 3. In an embodiment, the DNA origin of replication and/or the gene encoding a protein regulating replication is not endogenous to the cyanobacterial cell. The plasmid can be a vector. The gene encoding the protein regulating replication can be co-located with the DNA origin of replication and the at least one recombinant gene on the plasmid, or can be located on different genetic elements. The gene encoding the protein regulating replication can also be integrated in the genome of the cyanobacterial cell. The production gene can be a biosynthetic pathway gene encoding an enzyme catalyzing a metabolic reaction which is not present in the wild-type *cyanobacterium*. The chemical compound can be a biofuel, such as an alkanol, alcohol, or ethanol. The chemical compound can be selected from alkanols, alkanes, alkenes, ethers, polyhydroxyalkanoates such as PHB, fatty acids, fatty acid esters, hydrogen, and combinations thereof. The production gene can have at least one gene selected from the group consisting of: a gene encoding pyruvate decarboxylase enzyme, a gene encoding alcohol dehydrogenase, a gene encoding alcohol dehydrogenase E enzyme (AdhE), and combinations thereof. The plasmid further can have a DNA origin of replication for replication of the vector in *Escherichia coli*. The plasmid can further have a DNA origin of transfer (oriT) for conjugational transfer of the vector from a bacterial host to the cyanobacterial cell. The cyanobacterial cell can be, for example, a *Synechococcus* sp., *Synechocystis* sp., *Chlorogloeopsis* sp., *Chroococcidiopsis* sp., or a *Cyanobacterium* sp. cell.

In yet another aspect of the invention, a nucleic acid sequence having at least 95% identity to SEQ ID NO: 2 is provided. The nucleic acid can further have a sequence having at least 70% identity to SEQ ID NO: 82 or SEQ ID NO: 83. The nucleic acid can further have a sequence having at least 70% identity to SEQ ID NO: 84 or SEQ ID NO: 85.

BRIEF DESCRIPTION OF THE DRAWINGS

FIG. 3A(1) through 3A(2) is a physical map of plasmid pABICyano2-2.5 (1-2498 bp) that was captured from *Cyanobacterium* sp. ABICyano2. The complete plasmid nucleotide sequence (SEQ ID NO: 1), as well as the deduced ORF1 nucleic acid sequence (SEQ ID NO: 2) and its amino acid sequence (SEQ ID NO: 3) are shown. Bioinformatically identified transcription factors (TF) are also indicated. Inverted repeats are marked by dashed arrows (reading direction) and numbered based on the order in each of the intergenic regions. Hypothetical promoter boxes (−35 and −10) are highlighted. A potential replication origin is shown in boldface and underlined. A putative motif (ETENYD-VNFD; SEQ ID NO: 4); located in the active site of the Rep protein, is shaded in grey. This motif was predicted based on homology to the consensus sequence of "EXXKYXVKXXD" (SEQ ID NO: 5) (where X can be any amino acid residue) of the active sites of Rep proteins from a group of bacterial plasmids that replicate by a rolling-circle mechanism (Seery et al., 1993). Another putative protein coding region was identified. The location of this sequence, "ORF2" is indicated in the figure. This sequence has a nucleic acid sequence of SEQ ID NO: 86 and an amino acid sequence of SEQ ID NO: 87.

FIGS. 8A and 8B: seven sets of PCR primers listed in Table 4 were used to test wild-type *Cyanobacterium* sp. ABICyano1 and GFP-pVC992S transformants: Set 1 and 2 are specific for *Cyanobacterium* sp. ABICyano1; Set 3 and 4 are specific for PCC 6803; Sets 5-7 are specific for transforming vector GFP-pVC992S. The Arabic number for each lane (1-7) corresponds to the respective primer set listed in Table 4. The lanes marked with an M indicate DNA molecular standard.

FIG. 8C: six sets of PCR primers listed in Table 4 were used to test PCC 7002 wild-type and GFP-pVC992S transformants. The lane makers correspond to primer sets in Table 4 in the following way: lane 1—primer set 5 (specific to PCC 7002); lane 2—primer set 2 (specific to *Cyanobacterium* sp. ABICyano1; lane 3—primer set 3 (specific to PCC 6803); lanes 4-6—primer sets 6-8 (specific to vector GFP-pVC992S). The lanes marked with an M indicate DNA molecular standard.

FIG. 18 is a photograph of a microscopic image of cyanobacterial cells transformed with either the full length (pSA131) or partial length (pCK5) plasmid as described in FIG. 17. Both constructs produced transformants.

DETAILED DESCRIPTION

Figure 1:
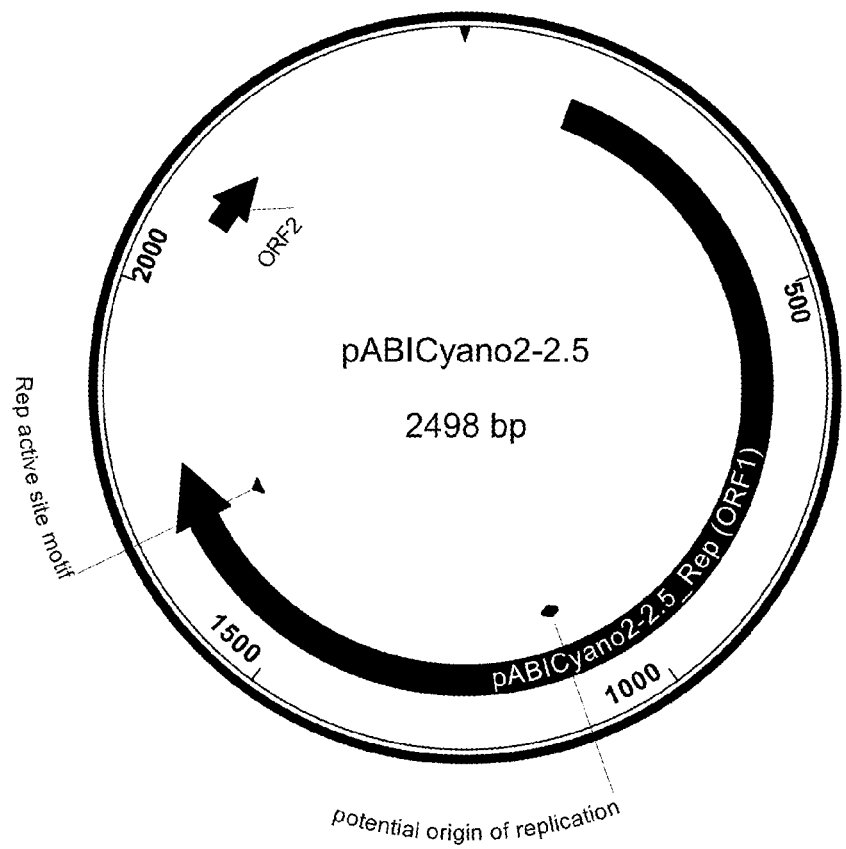
FIG. 1 is a schematic diagram showing the arrangement of relevant genetic regions present in *Cyanobacterium* sp. ABICyano2 plasmid p-2.5. Each ORF is represented with an arrowed box showing the transcriptional direction. Locations of the origin of replication and putative active site motif of the replication protein are also indicated.

A novel shuttle vector system has been developed which can transform a broad range of cyanobacterial species. Further, because the vector is designed to replicate in both cyanobacteria and in *E. coli*, it is relatively easy to genetically manipulate. The broad host range and ease of genetic manipulation of this new shuttle vector makes it an efficient and versatile gene delivery vehicle for genetic engineering in many different types of cyanobacteria.

Definitions

Unless defined otherwise, all technical and scientific terms used herein have the meaning commonly understood by a person skilled in the art to which this invention belongs. As used herein, the following terms have the meanings ascribed to them unless specified otherwise.

The term "about" is used herein to mean approximately, in the region of, roughly, or around. When the term "about" is used in conjunction with a numerical value/range, it modifies that value/range by extending the boundaries above and below the numerical value(s) set forth. In general, the term "about" is used herein to modify a numerical value(s) above and below the stated value(s) by a variance of 20%.

Aspects of the invention utilize techniques and methods common to the fields of molecular biology, microbiology and cell culture. Useful laboratory references for these types of methodologies are readily available to those skilled in the art. See, for example, Molecular Cloning: A Laboratory Manual (Third Edition), Sambrook, J., et al. (2001) Cold Spring Harbor Laboratory Press; Current Protocols in Microbiology (2007) Edited by Coico, R, et al., John Wiley and Sons, Inc.; The Molecular Biology of Cyanobacteria (1994) Donald Bryant (Ed.), Springer Netherlands; Handbook Of Microalgal Culture Biotechnology And Applied Phycology (2003) Richmond, A.; (ed.), Blackwell Publishing; and "The cyanobacteria, molecular Biology, Genomics and Evolution", Edited by Antonia Herrero and Enrique Flores, Caister Academic Press, Norfolk, UK, 2008.

The term "*Cyanobacterium*" refers to a member from the group of photoautotrophic prokaryotic microorganisms which can utilize solar energy and fix carbon dioxide. Cyanobacteria are also referred to as blue-green algae.

The terms "host cell" and "recombinant host cell" are intended to include a cell suitable for metabolic manipulation, e.g., which can incorporate heterologous polynucleotide sequences, e.g., which can be transformed. The term is intended to include progeny of the cell originally transformed. In particular embodiments, the cell is a prokaryotic cell, e.g., a cyanobacterial cell. The term recombinant host cell is intended to include a cell that has already been selected or engineered to have certain desirable properties and suitable for further enhancement using the compositions and methods of the invention.

"Competent to express" refers to a host cell that provides a sufficient cellular environment for expression of endogenous and/or exogenous polynucleotides.

As used herein, the terms "genetically modified" or "genetically enhanced" refers to any change in the endogenous genome of a wild-type cell or to the addition of non-endogenous genetic code to a wild-type cell, e.g., the introduction of a heterologous gene. More specifically, such changes are made by the hand of man through the use of recombinant DNA technology or mutagenesis. The changes can involve protein coding sequences or non-protein coding sequences, including regulatory sequences such as promoters or enhancers.

The term "gene" refers to an assembly of nucleotides that encode a polypeptide, and includes cDNA and genomic DNA nucleic acids. "Gene" also refers to a nucleic acid fragment that expresses a specific protein or polypeptide, including regulatory sequences preceding (5' non-coding sequences) and following (3' non-coding sequences) the coding sequence.

The terms "polynucleotide" and "nucleic acid" also refer to a polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs. It will be understood that, where required by context, when a nucleotide sequence is represented by a DNA sequence (i.e., A, T, G, C), this also includes an RNA sequence (i.e., A, U, G, C) in which "U" replaces "T."

The nucleic acids of this present invention may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications such as uncharged linkages, charged linkages, alkylators, intercalators, pendent moieties, modified linkages, and chelators. Also included are synthetic molecules that mimic polynucleotides in their ability to bind to a designated sequence via hydrogen bonding and other chemical interactions.

The term "nucleic acid" (also referred to as polynucleotide) is also intended to include nucleic acid molecules having an open reading frame encoding a polypeptide, and can further include non-coding regulatory sequences and introns. In addition, the terms are intended to include one or more genes that map to a functional locus. In addition, the terms are intended to include a specific gene for a selected purpose. The gene can be endogenous to the host cell or can be recombinantly introduced into the host cell.

In one aspect the invention also provides nucleic acids which are at least 60%, 70%, 80% 90%, 95%, 99%, or 99.5% identical to the nucleic acids disclosed herein.

The percentage of identity of two nucleic acid sequences or two amino acid sequences can be determined using the algorithm of Thompson et al. (CLUSTALW, 1994, Nucleic Acids Research 22: 4673-4680). A nucleotide sequence or an amino acid sequence can also be used as a so-called "query sequence" to perform a search against public nucleic acid or protein sequence databases in order, for example, to identify further unknown homologous promoters, which can also be used in embodiments of this invention. In addition, any nucleic acid sequences or protein sequences disclosed in this patent application can also be used as a "query sequence" in order to identify yet unknown sequences in public databases, which can encode for example new enzymes, which could be useful in this invention. Such searches can be performed using the algorithm of Karlin and Altschul (1990, Proceedings of the National Academy of Sciences U.S.A. 87: 2,264 to 2,268), modified as in Karlin and Altschul (1993, Proceedings of the National Academy of Sciences U.S.A. 90: 5,873 to 5,877). Such an algorithm is incorporated in the NBLAST and XBLAST programs of Altschul et al. (1990, Journal of Molecular Biology 215: 403 to 410). Suitable parameters for these database searches with these programs are, for example, a score of 100 and a word length of 12 for BLAST nucleotide searches as performed with the NBLAST program. BLAST protein searches are performed with the XBLAST program with a score of 50 and a word length of 3. Where gaps exist between two sequences, gapped BLAST is utilized as described in Altschul et al. (1997, Nucleic Acids Research, 25: 3,389 to 3,402).

Database entry numbers given in the following are for the CyanoBase, the genome database for cyanobacteria (available on the world wide web at bacteria.kazusa.or.jp/cyanobase/index.html); Nakamura et al. "CyanoBase, the genome database for *Synechocystis* sp. Strain PCC 6803: status for the year 2000", Nucleic Acid Research, 2000, Vol. 18, page 72.

The EC numbers cited throughout this patent application are enzyme commission numbers which is a numerical classification scheme for enzymes based on the chemical reactions which are catalyzed by the enzymes.

The term "homologous recombination" refers to the process of recombination between two nucleic acid molecules based on nucleic acid sequence similarity. The term embraces both reciprocal and nonreciprocal recombination (also referred to as gene conversion). In addition, the recombination can be the result of equivalent or non-equivalent cross-over events. Equivalent crossing over occurs between two equivalent sequences or chromosome regions, whereas nonequivalent crossing over occurs between identical (or substantially identical) segments of nonequivalent sequences or chromosome regions. Unequal crossing over typically results in gene duplications and deletions. For a description of the enzymes and mechanisms involved in homologous recombination see Court et al., "Genetic engineering using homologous recombination," Annual Review of Genetics, 36:361-388; 2002.

The term "non-homologous or random integration" refers to any process by which DNA is integrated into the genome that does not involve homologous recombination. It appears to be a random process in which incorporation can occur at any of a large number of genomic locations.

The term "expressed endogenously" refers to polynucleotides that are native to the host cell and are naturally expressed in the host cell.

The term "vector" as used herein is intended to refer to a nucleic acid molecule capable of transporting another nucleic acid to which it has been linked. One type of vector is a "plasmid," which generally refers to a circular double stranded DNA molecule into which additional DNA segments may be ligated, but also includes linear double-stranded molecules such as those resulting from amplification by the polymerase chain reaction (PCR) or from treatment of a circular plasmid with a restriction enzyme.

Certain vectors are capable of autonomous replication in a host cell into which they are introduced (e.g., vectors having an origin of replication which functions in the host cell). Other vectors can be integrated into the genome of a host cell upon introduction into the host cell, and are thereby replicated along with the host genome. Moreover, certain vectors are capable of directing the expression of genes to which they are operatively linked. Such vectors are referred to herein as "recombinant expression vectors" (or simply "expression vectors").

The term "rolling circle DNA replication" is a mechanism for the replication of DNA wherein one strand of a parent dsDNA molecule is nicked, and DNA synthesis proceeds by elongation of the 3'-OH end, with progressive displacement of the 5'-end. The unbroken circular strand acts as the template. The partly replicated intermediate is a double-stranded circular DNA with a single-stranded displaced tail.

The term "replicon" means any DNA sequence or molecule which possesses a replication origin and which is therefore potentially capable of being replicated in a suitable cell.

"RCR replicons" or "rolling circle replicons" are replicons that reproduce by the rolling circle DNA replication mechanism.

A "promoter" is an array of nucleic acid control sequences that direct transcription of an associated polynucleotide, which may be a heterologous or native polynucleotide. A promoter includes nucleic acid sequences near the start site of transcription, such as a polymerase binding site. The promoter also optionally includes distal enhancer or repressor elements which can be located as much as several thousand base pairs from the start site of transcription. The term "promoter" is intended to include a polynucleotide segment that can transcriptionally control a gene of interest, e.g., a pyruvate decarboxylase gene that it does or does not transcriptionally control in nature. In one embodiment, the transcriptional control of a promoter results in an increase in expression of the gene of interest. In an embodiment, a promoter is placed 5' to the gene-of-interest. A heterologous promoter can be used to replace the natural promoter, or can be used in addition to the natural promoter. A promoter can be endogenous with regard to the host cell in which it is used or it can be a heterologous polynucleotide sequence introduced into the host cell, e.g., exogenous with regard to the host cell in which it is used. Promoters of the invention may also be inducible, meaning that certain exogenous stimuli (e.g., nutrient starvation, heat shock, mechanical stress, light exposure, etc.) will induce the promoter leading to the transcription of the gene.

The phrase "operably linked" means that the nucleotide sequence of the nucleic acid molecule or gene of interest is linked to the regulatory sequence(s) in a manner which allows for regulation of expression (e.g., enhanced, increased, constitutive, basal, attenuated, decreased or repressed expression) of the nucleotide sequence and expression of a gene product encoded by the nucleotide sequence (e.g., when the recombinant nucleic acid molecule is included in a recombinant vector, as defined herein, and is introduced into a microorganism). This term refers to a functional relationship between two parts in which the activity of one part (e.g., the ability to regulate transcription) results in an action on the other part (e.g., transcription of the sequence). Thus, a polynucleotide is "operably linked to a promoter" when there is a functional linkage between a polynucleotide expression control sequence (such as a promoter or other transcription regulation sequences) and a second polynucleotide sequence (e.g., a native or a heterologous polynucleotide), where the expression control sequence directs transcription of the polynucleotide.

The term "terminator" refers to a nucleic acid sequence which is able to terminate the transcription of a mRNA. The terminators can exert their function in various ways including, but not limited to forming a hairpin structure in the mRNA transcript, which disrupts the mRNA-DNA RNA polymerase complex during transcription or via forming a recognition site for a transcription termination factor. Non-limiting examples are dsrA from *E. coli*, the oop terminator or the rho terminator.

The term "genome" refers to the chromosomal genome as well as to extrachromosomal plasmids which are normally present in the wild type *cyanobacterium* without having performed recombinant DNA technology. For example, cyanobacteria such as *Synechococcus* PCC 7002 can contain at least up to 6 different extrachromosomal plasmids in their wild type form. Each of the plasmids can have a number of copies per cell.

As used herein, the term "recombinant" refers to nucleic acid sequences and in particular to genes, which are altered by laboratory methods thereby creating combinations of nucleic acid sequences in a host cell which are not found in the respective wild type host cell. This term can apply to nucleic acid sequences which are both endogenous as well as heterologous with respect to the host cell. The term "recombinant" further refers to polynucleotides synthesized or otherwise manipulated in vitro ("recombinant polynucleotides") and to methods of using recombinant polynucleotides to produce gene products encoded by those polynucleotides in cells or other biological systems. For example, a cloned polynucleotide may be inserted into a suitable expression vector, such as a bacterial plasmid, and the plasmid can be used to transform a suitable host cell. A host cell that comprises the recombinant polynucleotide is referred to as a "recombinant host cell" or a "recombinant bacterium" or a "recombinant *cyanobacterium*." The gene is then expressed in the recombinant host cell to produce, e.g., a "recombinant protein." A recombinant polynucleotide may serve a non-coding function (e.g., promoter, origin of replication, ribosome-binding site, etc.) as well.

The term "recombinant nucleic acid molecule" includes a nucleic acid molecule (e.g., a DNA molecule) that has been altered, modified or engineered such that it differs in nucleotide sequence from the native or natural nucleic acid molecule from which the recombinant nucleic acid molecule was derived (e.g., by addition, deletion or substitution of one or more nucleotides). The recombinant nucleic acid molecule (e.g., a recombinant DNA molecule) also includes an isolated nucleic acid molecule or gene of the present invention.

The term "endogenous gene" refers to a native gene in its natural location in the genome of an organism. A "foreign" gene or "heterologous" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

The term "fragment" refers to a nucleotide sequence of reduced length relative to the reference nucleic acid and comprising, over the common portion, a nucleotide sequence substantially identical to the reference nucleic acid. Such a nucleic acid fragment according to the invention may be, where appropriate, included in a larger polynucleotide of which it is a constituent. Such fragments comprise, or alternatively consist of, oligonucleotides ranging in length from at least about 6 to about 1500 or more consecutive nucleotides of a polynucleotide according to the invention.

The term "open reading frame," abbreviated as "ORF," refers to a length of nucleic acid sequence, either DNA, cDNA or RNA, that comprises a translation start signal or initiation codon, such as an ATG or AUG, and a termination codon and can be potentially translated into a polypeptide sequence.

The term "upstream" refers to a nucleotide sequence that is located 5' to reference nucleotide sequence. In particular, upstream nucleotide sequences generally relate to sequences that are located on the 5' side of a coding sequence or starting point of transcription. For example, most promoters are located upstream of the start site of transcription.

The term "downstream" refers to a nucleotide sequence that is located 3' to a reference nucleotide sequence. In particular, downstream nucleotide sequences generally relate to sequences that follow the starting point of transcription. For example, the translation initiation codon of a gene is located downstream of the start site of transcription.

The term "homology" refers to the percent of identity between two polynucleotide or two polypeptide moieties. The correspondence between the sequence from one moiety to another can be determined by techniques known to the art. For example, homology can be determined by a direct comparison of the sequence information between two polypeptide molecules by aligning the sequence information and using readily available computer programs. Alternatively, homology can be determined by hybridization of polynucleotides under conditions that form stable duplexes between homologous regions, followed by digestion with single-stranded-specific nuclease(s) and size determination of the digested fragments.

As used herein, "substantially similar" refers to nucleic acid fragments wherein changes in one or more nucleotide bases results in substitution of one or more amino acids, but do not affect the functional properties of the protein encoded by the DNA sequence. The term "substantially similar" also refers to modifications of the nucleic acid fragments of the instant invention such as deletion or insertion of one or more nucleotide bases that do not substantially affect the functional properties of the resulting transcript.

The terms "restriction endonuclease" and "restriction enzyme" refer to an enzyme that binds and cuts within a specific nucleotide sequence within double stranded DNA.

The term "expression", as used herein, refers to the transcription and stable accumulation mRNA derived from a nucleic acid or polynucleotide. Expression may also refer to translation of mRNA into a protein or polypeptide.

An "expression cassette" or "construct" refers to a series of polynucleotide elements that permit transcription of a gene in a host cell. Typically, the expression cassette includes a promoter and a heterologous or native polynucleotide sequence that is transcribed. Expression cassettes or constructs may also include, e.g., transcription termination signals, polyadenylation signals, and enhancer elements.

The term "codon" refers to a triplet of nucleotides coding for a single amino acid.

The term "codon-anticodon recognition" refers to the interaction between a codon on an mRNA molecule and the corresponding anticodon on a tRNA molecule.

The term "codon bias" refers to the fact that different organisms use different codon frequencies.

The term "codon optimization" refers to the modification of at least some of the codons present in a heterologous gene sequence from a triplet code that is not generally used in the host organism to a triplet code that is more common in the particular host organism. This can result in a higher expression level of the gene of interest.

The term "transformation" is used herein to mean the insertion of heterologous genetic material into the host cell. Typically, the genetic material is DNA on a plasmid vector, but other means can also be employed. General transformation methods and selectable markers for bacteria and cyanobacteria are known in the art (Wirth, Mol Gen Genet. 216:175-177 (1989); Koksharova, Appl Microbiol Biotechnol 58:123-137 (2002). Additionally, transformation methods and selectable markers for use in bacteria are well known (see, e.g., Sambrook et al, supra).

The term "reporter gene" means a nucleic acid encoding an identifying factor that can be identified based upon the reporter gene's effect, in order to determine or confirm that a cell or organism contains the nucleic acid of interest, and/or to measure gene expression induction or transcription. Examples of reporter genes known and used in the art include but are not limited to luciferase (Luc), green fluorescent protein (GFP), chloramphenicol acetyltransferase (CAT), β-galactosidase (LacZ), β-glucuronidase (GUS), and the like. Selectable marker genes may also be considered reporter genes.

The term "GFP" refers to green fluorescent protein or the gene encoding it. This protein emits a bright fluorescence upon excitation with a specific wavelength of light. The GFP protein is often used as a "reporter gene" for cell transformation, gene expression studies, or cellular localization purposes. Several variant sequences are available, having different emission wavelengths or other characteristics to make them suitable for various molecular biology uses.

The term "selectable marker" means an identifying factor, usually an antibiotic or chemical resistance gene, that is able to be selected for based upon the marker gene's effect, i.e., resistance to an antibiotic, resistance to a herbicide, colorimetric markers, enzymes, fluorescent markers, and the like, wherein the effect is used to track the inheritance of a nucleic acid of interest and/or to identify a cell or organism that has inherited the nucleic acid of interest. Examples of selectable marker genes known and used in the art include: genes providing resistance to ampicillin, streptomycin, gentamycin, spectinomycin, kanamycin, hygromycin, and the like.

A "polypeptide" is a polymeric compound comprised of covalently linked amino acid residues. A "protein" is a polypeptide that performs a structural or functional role in a living cell.

A "heterologous protein" refers to a protein not naturally produced in the cell.

An "isolated polypeptide" or "isolated protein" is a polypeptide or protein that is substantially free of those compounds that are normally associated therewith in its natural state (e.g., other proteins or polypeptides, nucleic acids, carbohydrates, lipids).

The term "fragment" of a polypeptide refers to a polypeptide whose amino acid sequence is shorter than that of the reference polypeptide. Such fragments of a polypeptide according to the invention may have a length of at least about 2 to about 300 or more amino acids.

A "variant" of a polypeptide or protein is any analogue, fragment, derivative, or mutant which is derived from a polypeptide or protein and which retains at least one biological property of the polypeptide or protein. Different variants of the polypeptide or protein may exist in nature. These variants may be allelic variations characterized by differences in the nucleotide sequences of the structural gene coding for the protein, or may involve differential splicing or post-translational modification. The skilled artisan can produce variants having single or multiple amino acid substitutions, deletions, additions, or replacements.

As used herein, the phrase "increased activity" refers to any genetic modification resulting in increased levels of enzyme function in a host cell. As known to one of ordinary skill in the art, enzyme activity may be increased by increasing the level of transcription, either by modifying promoter function or by increasing gene copy number, increasing translational efficiency of an enzyme messenger RNA, e.g., by modifying ribosomal binding, or by increasing the stability of an enzyme, which increases the half-life of the protein, leading to the presence of more enzyme molecules in the cell. All of these represent non-limiting examples of increasing the activity of an enzyme. (mRNA Processing and Metabolism: Methods and Protocols, Edited by Daniel R. Schoenberg, Humana Press Inc., Totowa, N.J.; 2004; ISBN 1-59259-750-5; Prokaryotic Gene Expression (1999) Baumberg, S., Oxford University Press, ISBN 0199636036; The Biomedical Engineering Handbook (2000) Bronzino, J. D., Springer, ISBN 354066808X).

The terms "pyruvate decarboxylase" and "PDC" refer to an enzyme that catalyzes the decarboxylation of pyruvic acid to acetaldehyde and carbon dioxide. A "pdc gene" refers to the gene encoding an enzyme that catalyzes the decarboxylation of pyruvic acid to acetaldehyde and carbon dioxide. The terms "Alcohol dehydrogenase" and "ADH" refer to an enzyme that facilitates the interconversion between alcohols and aldehydes or ketones. An "adh gene" refers to the gene encoding an enzyme that facilitates the interconversion between alcohols and aldehydes or ketones, "pdc/adh" refers to the pdc and adh enzymes collectively. A "pdc/adh cassette" refers to a nucleic acid sequence encoding a pdc enzyme and an adh enzyme.

The term "primer" is an oligonucleotide that hybridizes to a target nucleic acid sequence to create a double stranded nucleic acid region that can serve as an initiation point for DNA synthesis under suitable conditions. Such primers may be used in a polymerase chain reaction.

The term "polymerase chain reaction," also termed "PCR," refers to an in vitro method for enzymatically amplifying specific nucleic acid sequences. PCR involves a repetitive series of temperature cycles with each cycle comprising three stages: denaturation of the template nucleic acid to separate the strands of the target molecule, annealing a single stranded PCR oligonucleotide primer to the template nucleic acid, and extension of the annealed primer(s) by DNA polymerase. PCR provides a means to detect the presence of the target molecule and, under quantitative or semi-quantitative conditions, to determine the relative amount of that target molecule within the starting pool of nucleic acids.

Novel Vector for Transformation and Expression in Cyanobacteria

Wild-type cyanobacterial cells and bacterial cells often contain endogenous plasmids, in addition to their chromosomal DNA. In order for plasmid vectors to replicate in a host organism, some type of system to allow the replication of the plasmid is used. Several different systems of replication machinery have been found to exist in various prokaryotic species. One such system is termed "rolling circle replication." The replication system found in the plasmid described herein is thought to work by a rolling circle method. This modified type of plasmid system may be able to replicate in numerous cyanobacterial species, making it a good candidate for genetic enhancement and for the production of compounds of interest in cyanobacteria.

In an embodiment, a novel plasmid vector system has been developed which can transform cyanobacteria from a broad range of genera. For example, the vector has been used to successfully transform several cyanobacterial strains, such as *Cyanobacterium* sp. ABICyano1, *Synechocystis* sp. PCC 6803, and *Synechococcus* sp. PCC 7002. The broad host range of the shuttle vector makes it an efficient and versatile gene delivery vehicle for genetic engineering in cyanobacteria.

Figure 2:
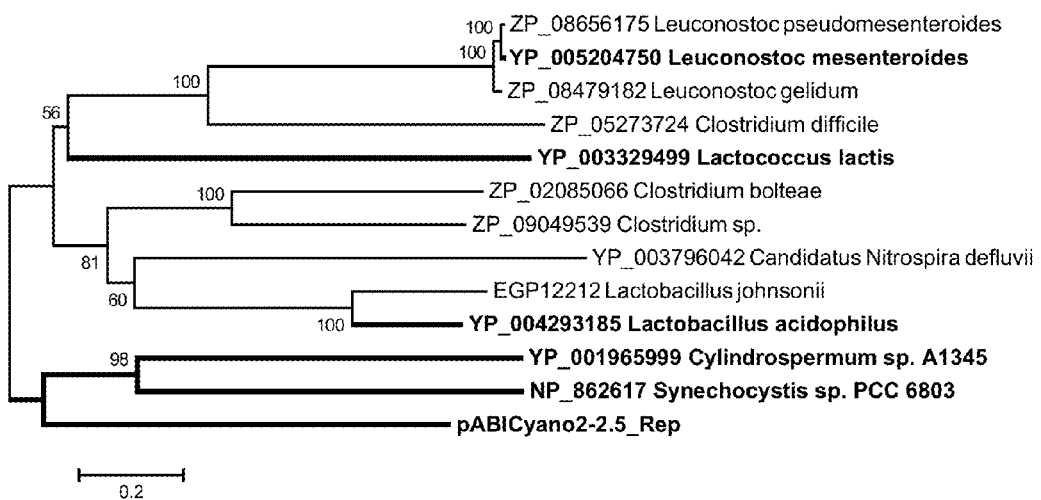
FIG. 2 is a phylogenetic tree showing the relationship between p-ABICyano2-2.5_Rep (ORF1) and significant homologs encoding other replication proteins. The phylogenetic tree was constructed with the MEGA program using the Dayhoff model of amino acid substitutions with 100 bootstraps. Sequence homologs of the ABICyano2-p2.5 plasmid replication protein are represented with their GenBank accession number followed by relevant taxonomic information. Branches and nodes for proteins from a known plasmid are highlighted in bold. The scale bar indicates the number of amino acid substitutions per site.

Characterization of the Original Endogenous plasmid ABICyano2 p-2.5 and its Replication Protein The *Cyanobacterium* sp. ABICyano2 plasmid p-2.5 (SEQ ID NO: 1) was found to carry an open reading frame (Orf1, 1629-bp DNA; SEQ ID NO: 2) that encodes a 542-amino acid replication protein (SEQ ID NO: 3). The replication protein found in the *Cyanobacterium* sp. ABICyano2 plasmid p-2.5 is approximately 40% similar to the replication initiation proteins (Rep) encoded in the pCB2.4 plasmid of *Synechocystis* sp. PCC 6803 (NP_862617.1) and the pCYLM01 plasmid of *Cylindrospermum* sp. A1345 (YP_001965999.1) (FIG. 2). The originally isolated plasmid was sequenced and characterized as detailed further in Example 3.

Although the plasmid is relatively small, at about 2.5 kb, it contains all of the replication machinery to replicate efficiently in cyanobacteria, most likely through the mechanism of rolling circle replication. The ABICyano2 p-2.5 plasmid carries an origin of replication[5'-TAGCAAGAT-ATTTTGATA-3'] (SEQ ID NO: 15) that resembles the nick site of a group of bacterial plasmids that replicate by a rolling circle mechanism (Seery et al., Plasmid 30:185-196; 1993), as evident as a conserved motif that was predicted based on homology to the consensus sequence (EXXKYXVKXXD (SEQ ID NO: 5), where X can be any amino acid) of the active sites of their Rep proteins. Accordingly, replication of the p2.5 plasmid is likely to be initiated by the replication initiation factor domain in the Rep protein, a probable topoisomerase (pfam02486 and COG2946) that makes a sequence-specific single-stranded nick in the plasmid DNA at the origin of replication.

Phylogenetic analysis revealed that the above-described replication initiation protein (REP) of the ABICyano2 plasmid p2.5 evolved earlier than those found in other cyanobacterial plasmids, as shown in FIG. 2. Thus, a conjugational replication protein ancestor may exist for cyanobacteria, which can potentially propagate into different species through horizontal transfer of plasmids.

New Cyanobacterial Plasmid Vector for Inserting DNA to Cyanobacterial Host Cells Due to the putative earlier genetic origin of this plasmid, it may be more likely to replicate and function in many divergent types of cyanobacterial cells. Thus, this plasmid sequence was chosen to be the backbone for the construction of a new modified vector that can be utilized as a gene delivery vehicle to transform various cyanobacterial host cells.

In an embodiment, the above-described vector was used as a starting point for producing the modified vector of the invention. In an embodiment, starting with the backbone of the p2.5 plasmid from *Cyanobacterium* sp. ABICyano2, modifications as described herein can be performed individually or together to increase transformation efficiency, increase the replication rate within the cell, and to increase the production of a desired product from the cyanobacterial cell.

The Plasmid Replication factor and its use in the New Vector

The originally characterized plasmid contains a replication factor involved in the replication of the plasmid, as mentioned above. In an embodiment of the invention, this replication factor can be used to allow the presence of recombinant genes in a host cell. This system can be used to efficiently carry foreign or recombinant genes in a host cell. By use of the gene encoding the replication factor, and, optionally, by use of the nucleic acid regions upstream and downstream of the replication factor, a plasmid, such as a endogenous-based plasmid, or a synthetically prepared plasmid, or a plasmid from another organism, can by arranged to be replicated in a host cyanobacterial cell.

In an embodiment of the invention, the gene sequence (SEQ ID NO: 2) of the replication factor (SEQ ID NO: 3) can be inserted to a host cell. The inserted gene can regulate replication of the plasmid it corresponds to. In another embodiment, the replication factor has a sequence of at least 70%, 75%, 80%, 85%, 90%, 95%, 98%, 99%, or 99.5% identity to the replication factor of SEQ ID NO: 3.

Accordingly, in an embodiment, gene delivery vehicles that are developed using this plasmid, or a portion of it, as a backbone can be used to transform a wide range of cyanobacteria with genes of interest. In another embodiment, the plasmid vector comprises the gene encoding the replication factor (SEQ ID NO: 2). In another embodiment, the plasmid vector comprises the gene encoding the replication factor and at least a portion of its upstream sequence (SEQ ID NO: 82 or SEQ ID NO: 83) and/or its downstream sequence (SEQ ID NO: 84 or SEQ ID NO: 85). Such vectors may also be able to efficiently produce heterologous proteins and products of interest in cyanobacteria.

The replication factor gene can be present at any suitable location in the host cell. In an embodiment, the gene is inserted on the plasmid of interest, or it can be inserted into another plasmid. The replication factor gene can also be located on the chromosome.

The expression of the replication protein (SEQ ID NO: 3) in the cell can allow the replication of a nucleic acid sequence in a circular plasmid vector sequence.

Vector Construction

In some embodiments, the plasmid construct preparation is performed in *E. coli* to allow for ease of genetic manipulation. Once the construct is prepared, the plasmid can then be transferred to the cyanobacterial cell, where it can replicate as an independent plasmid. Methods of genetic engineering of plasmids using *E. coli* are generally known in the art.

The *Cyanobacterium* sp. ABICyano2 p2.5 endogenous plasmid can be used as a backbone for the universal vector. In an embodiment, the entire endogenous plasmid is inserted into the shuttle vector, as shown in Example 5. In another embodiment, a sequence of about 70%, 75%, 80% 85%, 90%, 95%, 98%, 99%, or 99.5% of the entire endogenous plasmid sequence is inserted into a shuttle vector.

Figure 7:
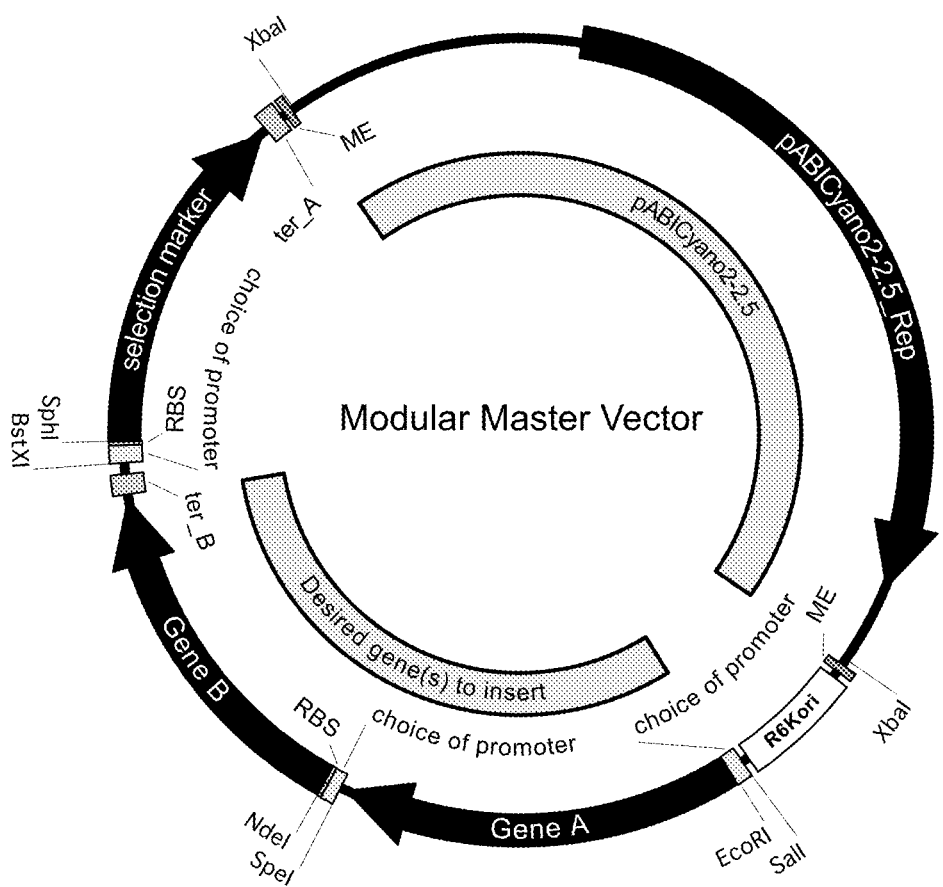
FIG. 7 is a master plasmid map showing the modular nature of the p ABICyano2 p2.5-based plasmid system. Various selection markers, inserted genes, and promoters can be chosen, as indicated. The p2.5-based plasmid region, the selection marker region, R6K origin of replication, and genes of interest are shown.

The universal vector of the invention is designed to have several modular units that can be easily swapped out using specific restriction enzymes. Promoters, genes of interest, selectable markers, and other desired sequences can be moved in and out of the vector as desired, as shown in FIG. 7. This modular design makes genetic experiments faster and more efficient.

In an embodiment, the new vector is a "shuttle" vector, which can replicate in both cyanobacteria and in *E. coli*. The shuttle vector contains a replication unit that can function in a broad range of cyanobacterial genera. The vector also contains a replicon for propagation in *E. coli* for ease of cloning and genetic manipulation using *E. coli*. Thus, in an embodiment, a plasmid shuttle vector is provided which is characterized by being replicable in both *Escherichia coli* and in a cyanobacterial species. The plasmid comprises a promoter capable of functioning in cyanobacteria and a DNA sequence encoding a sequence capable of functioning as a selective marker for both *Escherichia coli* and cyanobacteria. The plasmid shuttle vector enables the efficient transformation of cyanobacteria.

Also disclosed is a recombinant vector in which a gene of interest is operably linked to the vector, and cyanobacterial cells transformed with the recombinant shuttle vector. The shuttle vector is relatively small in size, relatively stable in a cyanobacterial host cell, and can replicate in a variety cyanobacterial species. This new vector is useful for expressing a variety of heterologous genes in cyanobacteria.

In an embodiment, the shuttle vector efficiently expresses a codon-optimized Spectinomycin resistance gene (SpecR) for selection of transformants and a codon-optimized a GFPmut2 (encoding green fluorescence protein) gene as a reporter. The shuttle vector was constructed based on a modular basis, so that all of the key elements (replication ori, AbR gene and reporter gene) are exchangeable via unique restriction sites, providing versatile cloning options and facilitating the delivery of genes of interest to the target organisms.

Other antibiotic resistance genes can be used if desired. For example, genes conferring resistance to ampicillin, gentamycin, kanamycin, or other antibiotics can be inserted into the vector, under the control of a suitable promoter. In some embodiments, the vector contains more than one antibiotic resistance gene.

In an embodiment, the vector of the invention is modified by several factors so that it is capable of efficient replication in multiple types of cyanobacterial species. It has also been organized so that various sequences can be easily replaced with other desired sequences as needed. Thus, a construct having a different gene (or genes) of interest, a different antibiotic, a different promoter, etc. can be made with relative ease. The modified vector allows for rapid testing of various heterologous constructs in a cyanobacterial cell.

In addition to the presence of the cyanobacterial origin of replication, the plasmid vector can also comprise an origin of replication suitable for Enterobacteriaceae, in particular *E. coli*, in order to ensure that the plasmid vector can be modified and propagated in Enterobacteriaceae, such as *E. coli*. Example 3 demonstrates the presence of an *E. coli* origin of replication in the plasmid. This was added for ease of manipulation of the plasmid in *E. coli*.

In an embodiment, the plasmid vector can also contain an origin of transfer (oriT) which is suitable for conjugation. In particular, the plasmid vector can contain a combined origin of replication and an origin of transfer (oriVT), which enables replication in Enterobacteriaceae, in particular *E. coli* and which also enables conjugation with, for example, an *E. coli* donor strain and a cyanobacterial recipient strain. Such an plasmid vector can be used for triparental mating wherein a conjugative plasmid present in one bacterial strain assists the transfer of a mobilizable plasmid, the plasmid vector of the present invention present in a second bacterial strain, into a third recipient strain, such as a host cyanobacterial strain.

Alternatively, the plasmid vector can also be synthesized via solid phase synthesis so that an origin of replication for Enterobacteriaceae does not need to be present in the plasmid vector.

In an embodiment, among the unique features of the new ABICyano2-based shuttle vector is the capability of broad-host range transformation among cyanobacteria, the expression of codon-optimized GFP gene as a reporter for easy confirmation of transformation, and the modular design, allowing the vector to be a versatile cloning tool for multiple species and multiple inserted genetic sequences. In an embodiment, the modular design of the shuttle vector allows complex sequence manipulation in cyanobacteria. In another embodiment, the modular design of the shuttle vector allows for the use (and the ease of replacement) of different promoter sequences, as discussed below.

Promoters

Any suitable promoter can be used to regulate the expression of the genes present in the shuttle vector. Exemplary promoter types include, for example, constitutive promoters, inducible promoters, endogenous promoters, heterologous promoters, and the like. In an embodiment, The SpecR and GFP genes are driven by promoters for photosystem II reaction center protein gene psbA (PpsbA) and phycocyanin beta subunit cpcB (PcpcB), respectively.

The promoter can be upstream of one gene to regulate that gene, or the promoter can be upstream of several genes, so that one promoter regulates the expression of more than one gene. Alternatively, in some embodiments, each inserted gene can be regulated by a separate promoter. In an embodiment, the promoter can be derived from the cyanobacterial host cell, or can be obtained from another cyanobacterial species, or can be obtained from another organism.

Exemplary promoters for expression in Cyanobacteria include but are not limited to Prbc, PpetJ, PpsbD, PnblA, PrpoA, PisiB, PrbcLS, PntcA, PnblA, PisiA, PpetJ, PpetE, PsigB, PlrtA, PhtpG, PhspA, PclpB1, PhliB, PggpS, PpsbA2, PpsaA, PnirA, PcrhC and the like. Examples of constitutive promoters that can be used include but are not limited to PrnpA, Prbs, PrpoA, PpsaA, PpsbA2, PpsbD, PcpcBA, and the like.

Exemplary promoters include, but are not limited to the psbA2 promoter from *Synechocystis* PCC 6803 (SEQ ID NO: 9), cpcBA promoter from *Synechocystis* PCC 6803

(SEQ ID NO: 16), nirA gene promoter (278 bp) from *Cyanobacterium* sp. ABICyano1 (SEQ ID NO: 17), lrtA (light-repressed protein, ribosomal subunit interface protein) gene promoter from *Cyanobacterium* sp. ABICyano1 (SEQ ID NO: 18), mrgA gene promoter (214 bp) from *Cyanobacterium* sp. ABICyano1 (SEQ ID NO: 19), nblA gene promoter (338 bp) from *Cyanobacterium* sp. ABICyano1 (SEQ ID NO: 20), ggpS (glucosylglycerol-phosphate synthase) gene promoter (408 bp) from *Cyanobacterium* sp. ABICyano1 (SEQ ID NO: 21), petJ gene promoter (411 bp) from *Cyanobacterium* sp. ABICyano1 (SEQ ID NO: 22), ppsA (phosphoenolpyruvate synthase gene) promoter (211 bp) from *Cyanobacterium* sp. ABICyano1 (SEQ ID NO: 23), rnpA (Ribonuclease P) gene promoter (542 bp) from *Cyanobacterium* sp. ABICyano1 (SEQ ID NO: 24), the pstS gene promoter (380 bp) from *Cyanobacterium* sp. ABICyano1 (SEQ ID NO: 25), and the like.

Examples of other suitable promoters to drive expression from the new vector include, for instance, the Prps promoter (SEQ ID NO: 26), The $PnblA_{7120}$ promoter from *Nostoc* sp. PCC 7120 (SEQ ID NO: 27), The $PrbcL_{6803}$ promoter from *Synechocystis* sp. PCC 6803 (SEQ ID NO: 28) and the $PsmtA_{7002}$ promoter from *Synechococcus* sp. PCC 7002 (SEQ ID NO: 29).

Many types of inducible promoters can be used. In an embodiment, the promoter is a metal-inducible promoter, such as copper inducible, zinc inducible, cobalt inducible, or nickel inducible. These types of promoters can be turned off when the expression of the compound of interest is not needed, but can be turned on by addition of a small amount of the indicated metal.

In an embodiment, a zinc-inducible promoter such as "PziaA" can be used in the vector to regulate gene expression. For example, the promoter PziaA regulates the expression of the gene ziaA (slr0798), encoding a zinc transporting ATPase ZiaA (NP_442636.1) which can transport zinc ions out of the intracellular space of *Synechocystis* sp. PCC 6803.

In an embodiment, a cobalt-inducible promoter "PcorT" can be used. An example of a cobalt-inducible promoter is the promoter PcorT, which regulates the expression of the gene corT (slr0797), which encodes a cobalt transporting ATPase (NP_442633.1) from *Synechocystis* PCC 6803 can be used in the vector to regulate gene expression.

In an embodiment, a nickel-inducible promoter can be used in the vector to regulate gene expression. For example, the promoter that regulates expression of the gene nrsB (slr0793), which encodes a protein involved in a multiprotein nickel resistance system in *Synechocystis* PCC 6803 can be used.

Several additional types of zinc-inducible, cobalt-inducible, and nickel-inducible promoters (as well as promoter/repressor systems) are described, for example, in U.S. Provisional Patent Application No. 61/581,928, which is incorporated herein by reference in its entirety.

Exemplary inducible promoters include but are not limited to PpetJ, PnblA, and PisiB, and the like. Differentially expressed promoters like PlrtA, PmrgA, PpstS, as well as synthetic promoters can also be used.

The promoters hspA, clpB1, and hliB, for example, can be induced by heat shock (for example, by raising the growth temperature of the host cell culture from 30° C. to 40° C.), cold shock (for example, by reducing the growth temperature of the cell culture from 30° C. to 20° C.), oxidative stress (for example, by adding oxidants such as hydrogen peroxide to the culture), or osmotic stress (for example by increasing the salinity). The promoter sigB can be induced by stationary growth, heat shock, and osmotic stress. The promoters ntcA and nblA can be induced by decreasing the concentration of nitrogen in the growth medium.

The promoters PpsaA and PpsbA2 can be induced by low light or high light conditions. The promoter htpG can be induced by osmotic stress and heat shock. The promoter PcrhC can be induced by cold shock.

The promoter petE can be induced by an increase in copper concentration. Alternatively, the promoter petJ can be induced by decreasing the copper concentration.

The chosen promoter elements can be combined with any of the genes encoding any of the enzymes of the invention by using standard molecular cloning techniques. Further description and characterization of constitutive or inducible promoters that can be useful in combination with the genes inserted onto the shuttle vector of the invention can include, for example: Samartzidou et al., "Transcriptional and Post-transcriptional Control of mRNA from lrtA, a Light-repressed Transcript in *Synechococcus* sp. PCC 7002," Plant Physiol. 117:225-234 (1998); Duran et al., "The Efficient Functioning of Photosynthesis and Respiration in *Synechocystis* sp. PCC 6803 Strictly Requires the Presence of either Cytochrome c6 or Plastocyanin," Journal of Biological Chemistry 279:7229-7233 (2004); Singh et al., "The Heat Shock Response in the *Cyanobacterium Synechocystis* sp. Strain PCC 6803 and Regulation of Gene Expression by HrcA and SigB," Arch Microbiol. 186:273-286 (2006); Imamura et al., "Antagonistic Dark/light-induced SigB/SigD, Group 2 Sigma Factors, Expression Through Redox Potential and their Roles in Cyanobacteria," FEBS Lett. 554:357-362 (2003); Imamura et al., "Growth Phase-dependent Activation of Nitrogen-related Genes by a Control Network of Group 1 and Group 2 Sigma Factors in a *Cyanobacterium*," Jour. Biol. Chem. 281:2668-2675 (2006); Agrawal et al., "Light-dependent and Rhythmic psbA Transcripts in Homologous/heterologous Cyanobacterial Cells," Biochem. Biophys. Res. Commun. 255:47-53 (1999); Mohamed et al., "Influence of Light on Accumulation of Photosynthesis-specific Transcripts in the *Cyanobacterium Synechocystis* 6803," Plant Mol. Biol. 13:693-700 (1989); Muramatsu et al., "Characterization of High-light-responsive Promoters of the psaAB Genes in *Synechocystis* sp. PCC 6803," Plant Cell Physiol. 47:878-890 (2006); Marin et al., "Gene Expression Profiling Reflects Physiological Processes in Salt Acclimation of *Synechocystis* sp. strain PCC 6803," Plant Physiol. 136:3290-3300 (2004). Marin et al., "Salt-dependent Expression of Glucosylglycerol-phosphate Synthase, Involved in Osmolyte Synthesis in the *Cyanobacterium Synechocystis* sp. Strain PCC 6803," Jour. Bacteriol. 184:2870-2877 (2002). Qi et al., "Application of the *Synechococcus* nirA Promoter to Establish an Inducible Expression System for Engineering the *Synechocystis* Tocopherol Pathway," Appl. Environ. Microbiol. 71:5678-5684 (2005); Maeda et al., "cis-acting Sequences Required for NtcB-dependent, Nitrite-responsive Positive Regulation of the Nitrate Assimilation Operon in the *Cyanobacterium Synechococcus* sp. Strain PCC 7942," Jour. Bacteriol. 180: 4080-4088 (1998); and Herranen et al., "Regulation of Photosystem I Reaction Center Genes in *Synechocystis* sp. Strain PCC 6803 During Light Acclimation," Plant Cell Physiol. 46:1484-1493 (2005; Buikema et al., "Expression of the *Anabaena* hetR gene from a Copper-regulated Promoter Leads to Heterocyst Differentiation under Repressing Conditions," Proc. Natl. Acad. Sci. USA. 98:2729-2734 (2001). Mary et al., "Effects of High Light on Transcripts of Stress-associated Genes for the Cyanobacteria *Synechocystis* sp. PCC 6803 and *Prochlorococcus* MED4 and MIT9313," Microbiology 150:1271-1281 (2004); He et al., "The High Light-inducible Polypeptides in *Synechocystis* PCC 6803. Expression and Function in High Light," Jour. Biol. Chem. 276:306-314 (2001); Fang et al., "Expression of the Heat Shock Gene hsp16.6 and Promoter Analysis in the *Cyanobacterium, Synechocystis* sp. PCC 6803," Curr Microbiol. 49:192-198 (2004); Kappell et al., "The Response Regulator RpaB Binds the High Light Regulatory 1 Sequence Upstream of the High-light-inducible hliB Gene from the *Cyanobacterium Synechocystis* PCC 6803," Arch. Microbiol. 187:337-342 (2007).

Reporter Genes

In an embodiment, a reporter gene can be used to confirm the transformation and successful production of a heterologous protein in the host cyanobacterial cell. A number of reporter genes are known in the art. Among some of the most commonly used reporter genes are those encoding luciferase, β-glucuronidase (GUS), and Green fluorescent protein (GFP) and its variant fluorescent proteins.

GFP from the jellyfish *Aequorea victoria* has emerged as a versatile reporter gene and in situ cell marker over the past two decades. Several variants of the GFP protein have been developed for the specific applications. One of these variants is GFPmut2 (Genbank Accession No. AF108217; nucleic acid SEQ ID NO: 14; amino acid SEQ ID NO: 13). This variant has an emission maxima of 511 nm when excited by blue light (481 nm), conferring a greatly increased (100-fold vs. wild-type GFP) fluorescence intensity, making it very useful for a number of applications (Cormack et al., Gene 173:33-38; 1996. In addition, unlike GFPuv, GFPmut2 is not excited by UV light, a difference that allows differential imaging of the reporter proteins in the same sample. The use of the new ABICyano2-based vector for transformation of several cyanobacterial species with a codon-optimized gene (nucleic acid SEQ ID NO: 12) encoding GFP is shown in examples 5, 7, 9, 14, 15, and 16.

Production of Compounds of Interest in Cyanobacteria

The new vector can be modified to carry one or more genes of interest into a new host cyanobacterial cell. In an embodiment, the added gene or genes are part of a biochemical pathway to produce a compound of interest in the cyanobacterial host cell. One, two, three, four, five, six, or seven or more heterologous genes can be added to the vector. In an embodiment, the compound of interest is a biofuel. In another embodiment, the compound of interest is ethanol.

The universal vector of the invention can harbor one or more genes for the production of a protein or a compound of interest in the host cell. In an embodiment, the GFP protein is produced, as shown herein in Examples 14 through 16. In an embodiment, genes that are involved in a biosynthetic pathway are inserted.

The universal vector of the invention can be used to carry a gene or genes involved in other biosynthetic pathways to produce a compound of interest. Exemplary compounds include but are not limited to organic carbon compounds, alcohols, fatty acids, oils, carotenoids, proteins, enzymes, biofuels, nutraceuticals, pharmaceuticals, and the like.

Use of the Vector for the Production of Ethanol in Cyanobacteria

In an embodiment of the invention, genes involved in the production of ethanol can be inserted into the vector. The genes can be codon optimized for cyanobacteria, and can utilize any suitable promoter and regulatory sequences. In an embodiment, the ethanol-producing genes are pyruvate decarboxylase (pdc) alcohol dehydrogenase (adh). In an embodiment, the adh and/or pdc genes can be obtained from an alcohol-fermenting organism, such as, for example, *Zymomonas mobilis, Zymobacter palmae*, and the like. The adh and/or pdc genes can also be obtained from a cyanobacterial species. In an embodiment, the adh and/or pdc genes are obtained from cyanobacterial species such as *Synechocystis* sp. PCC 6803, *Synechococcus* sp. PCC 7002, and the like. In an embodiment, the gene encoding the PDC enzyme is from *Zymomonas* or *Zymobacter*, while the gene encoding ADH is from *Synechocystis* sp PCC 6803. The genes can also be obtained, for example, from eukaryotes such as the yeast *Saccharomyces cerevisiae*.

In an embodiment, the enzyme involved in the biosynthetic pathway for ethanol production is a pyruvate decarboxylase. Pyruvate decarboxylase converts pyruvate to acetaldehyde. In an embodiment, the PDC enzyme is EC 4.1.1.1. In an embodiment, the amino acid sequence of the PDC enzyme is at least 80%, 85%, 90%, 95%, 98%, or 99% identical to the PDC sequence derived from *Zymomonas mobilis* (SEQ ID NO: 41). In an embodiment, the nucleic acid sequence encoding the PDC enzyme is at least 80%, 85%, 90%, 95%, 98%, or 99% identical to SEQ ID NO: 40 (*Zymomonas mobilis* wild-type) or SEQ ID NO: 42 (codon-optimized).

Other exemplary pyruvate decarboxylase enzymes from various organisms include, for example, pyruvate decarboxylase (EC 4.1.1.1) 568 amino acid protein from *Zymomonas mobilis*, Accession: AAA27697.1 or AAA27685.1; pyruvate decarboxylase (EC 4.1.1.1), CBF76546.1; 568 amino acid protein from *Aspergillus nidulans*; pyruvate decarboxylase isozyme 1 (EC 4.1.1.1), 589 amino acid protein from *Cryptosporidium muris* RN66, Accession: EEA05305.1.

Additional accession numbers of exemplary pyruvate decarboxylase proteins include but are not limited to: YP_163095.1; YP_005622002.1; CAA42157.1; AAA27697.1; AAD19711.1; AEH63551.1; YP_005278583.1; YP_006165964.1; YP_006165972.1; YP_006165980.1; YP_006165988.1; YP_006165996.1; YP_006166004.1; YP_006166012.1; YP_006166020.1; YP_006166028.1; YP_006166036.1; YP_006166044.1; YP_006166052.1; YP_006166060.1; YP_006166076.1; YP_006166100.1; AAA27696.2; ADX51519.1; AFH18612.1; AFH18628.1; AFH18708.1; YP_003226937.1; BAF76067.1; ADK13058.1; YP_006519091.1; AAA27685.1; and the like.

In a further embodiment, the enzyme involved in the biosynthetic pathway for ethanol production is an alcohol dehydrogenase. Alcohol dehydrogenase converts acetaldehyde to ethanol. The alcohol dehydrogenases can be $Zn^{2+}$ or iron dependent alcohol dehydrogenases, for example ADHI, ADHII from *Zymomonas mobilis*, SynADH from *Synechocystis* PCC 6803 or even ADHE, which is able to directly convert acetyl coenzyme A into ethanol. In an embodiment, the ADH enzyme is EC 1.1.1.2 or EC 1.1.1.1. In an embodiment, the amino acid sequence of the ADH enzyme is at least 80%, 85%, 90%, 95%, 98%, or 99% identical to SEQ ID NO: 45. In an embodiment, the nucleic acid sequence encoding the ADH enzyme is at least 80%, 85%, 90%, 95%, 98%, or 99% identical to SEQ ID NO: 44 or 46.

Additional examples of alcohol dehydrogenases belonging to the above-mentioned enzyme class EC 1.1.1.1 include, for example, accession numbers CBW73784.1; CBG24634.1; CAR33004.1; and CAR37359.1.

Additional examples of alcohol dehydrogenases belonging to enzyme class EC 1.1.1.2 include YP_002344920.1; GI: 218563141; CAL35648.1; CAD96758.1; and CAA16130.1.

Use of the Vector for the Production of Other Compounds in Cyanobacteria

Two other alcohols which are relatively widespread are propanol and butanol. Similar to ethanol, they can be produced by fermentation processes. The following enzymes are involved in isopropanol fermentation and can be encoded first and/or second recombinant genes: acetyl-CoA acetyltransferase (EC:2.3.1.9), acetyl-CoA:acetoacetyl-CoA transferase (EC:2.8.3.8), acetoacetate decarboxylase (EC:4.1.1.4) and isopropanol dehydrogenase (EC:1.1.1.80).

The following enzymes are involved in isobutanol fermentation: acetolactate synthase (EC:2.2.1.6), acetolactate reductoisomerase (EC:1.1.1.86), 2,3-dihydroxy-3-methyl-butanoate dehydratase (EC:4.2.1.9), a-ketoisovalerate decarboxylase (EC:4.1.1.74), and alcohol dehydrogenase (EC:1.1.1.1).

In an embodiment of the invention, the inserted genes can encode enzymes involved in the biosynthesis of ethylene as a chemical compound. The at least one recombinant gene encodes an enzyme for ethylene formation, in particular the ethylene-forming enzyme 1-aminocyclopropane-1-carboxylate oxidase (EC 1.14.17.4), which catalyzes the last step of ethylene formation, the oxidation of 1-aminocyclopropane-1-carboxylic acid to ethylene. The substrate for the ethylene-forming enzyme is synthesized by the enzyme 1-aminocyclopropane-1-carboxylic acid synthase (EC 4.4.1.14) from the amino acid methionine.

In an embodiment of the invention, the inserted genes can encode enzymes involved in the biosynthesis of an isoprenoid compound, such as isoprene. The at least one recombinant gene encodes an enzyme such as isoprene synthase. Isoprene synthase (EC 4.2.3.27) catalyzes the chemical reaction from dimethylallyl diphosphate to isoprene and diphosphate.

In an embodiment of the invention, the inserted genes can encode enzymes involved in the biosynthesis of terpene. The terpenes are a large and very diverse class of organic compounds, produced primarily by a wide variety of plants, particularly conifers. Terpenes are derived biosynthetically from units of isoprene and are major biosynthetic building blocks in nearly every living organism. For example, steroids are derivatives of the triterpene squalene. When terpenes are modified chemically, such as by oxidation or rearrangement of the carbon skeleton, the resulting compounds are generally referred to as terpenoids. Terpenes and terpenoids are the primary constituents of the essential oils for many types of plants and flowers. Examples of biosynthetic enzymes are farnesyl pyrophosphate synthase (EC 2.5.1.1), which catalyzes the reaction of dimethylallylpyrophosphate and isopentenyl pryrophosphate yielding farnesyl pyrophosphate. Another example is geranylgeranyl pyrophosphate synthase (EC 2.5.1.29), which catalyzes the reaction between transfarnesyl diphosphate and isopentenyl diphosphate yielding diphosphate and geranylgeranyl diphosphate.

In the case that the chemical compound is hydrogen, the first and/or second recombinant genes can for example code for hydrogenase an enzyme catalyzing the following reaction:

12H$^+$+12X reduced→6 H$_2$+12X oxidized, wherein X is an electron carrier such as ferredoxin.

Further examples of valuable chemical compounds that can be produced in cyanobacteria are the so-called non-ribosomal peptides (NRP) and the polyketides (PK). These compounds are synthesized by plants, fungi and only a few bacteria such as actinomycetes, myxobacteria and cyanobacteria. They are a group of structurally diverse secondary metabolites and often possess bioactivities of high pharmacological relevance. Hybrids of non-ribosomal peptides and polyketides also exist, exhibiting both a peptide and a polyketide part. Recombinant genes for the production of non-ribosomal peptides as the first chemical compounds are for example gene clusters encoding for non-ribosomal peptide synthetases (NRPS). NRPS are characteristic modular multidomain enzyme complexes encoded by modular non-ribosomal peptide synthetase gene clusters. Examples for non-ribosomal peptide synthetases are Actinomycin Synthetase and Gramicidin Synthetase.

In general there are two distinct groups of polyketides (PK), the reduced polyketides of type I, the so-called macrolides and the aromatic polyketides of type II. Type I polyketides are synthesized by modular polyketide synthases (PKS), which are characteristic modular multidomain enzyme complexes encoded by modular PKS gene clusters. Examples for recombinant genes for the production of type I polyketides are the Rapamycin Synthase gene cluster and the Oleandomycin Synthase gene cluster. One example for a recombinant gene for type II polyketides is the Actinorhodin polyketide synthase gene cluster. Examples for recombinant genes for the production of hybrids of polyketides and non-ribosomal peptides are the Microcystin Synthetase gene cluster, Microginin Synthetase gene cluster, and Myxothiazole Synthetase gene cluster.

Further examples of valuable chemical compounds are the alkaloids. Accordingly, in an embodiment of the invention, the inserted genes can encode enzymes involved in alkaloid biosynthesis. Alkaloids have highly complex chemical structures and pronounced pharmacological activities. Examples for biosynthetic enzymes for alkaloids which can be encoded by recombinant genes for the production of the chemical compound are strictosidine synthase, which catalyzes the stereoselective Pictet-Spengler reaction of tryptamine and secologanin to form 3a(S)-strictosidine. The primary importance of strictosidine is not only its precursor role for the biosynthetic pathway of ajmaline but also because it initiates all pathways leading to the entire monoterpene indol alkaloid family. Another example of an enzyme encoded by a recombinant gene is strictosidine glucosidase from the ajmaline biosynthetic pathway. This enzyme is able to activate strictosidine by deglycosylation thus generating an aglycon. This aglycon of strictosidine is the precursor for more than 2,000 monoterpenoid indol alkaloids.

Further examples of enzymes encoded by at least one recombinant gene are:
- (R,S)-3'-hydroxy-N-methylcoclaurine 4'-O-methyl ¬ transferase (4'OMT) central to the biosynthesis of most tetrahydrobenzyh¬isoquinolin-derived alkaloids;
- Berberine bridge enzyme (BBE) specific to the sanguinarine pathway;
- (R,S)-reticuline 7-O-methyltransferase (7OMT) specific to laudanosine formation;
- Salutaridinol 7-O-acetyltransferase (SalAT) and codeinone reductase that lead to morphine.

Vitamins, as further examples of chemical compounds, are organic compounds that are essential nutrients for certain organisms and act mainly as cofactors in enzymatic reactions but can also have further importance, e.g. as anti oxidants in case of vitamin C. Vitamin C can be synthesized via the L-Ascorbic acid (L-AA) biosynthetic pathway from D-glucose in plants. The following enzymes are involved in vitamin C synthesis and can be encoded by recombinant genes on the vector:

Hexokinase, Glucose-6-phosphate isomerase, Mannose-6-phosphate isomerase, Phosphomannomutase, Mannose-1-phosphate guanylyltransferase, GDP-mannose-3,5-epimerase, GDP-L-galactose phosphorylase, L-Galactose 1-phosphate phosphatase, L-galactose dehydrogenase, L-galactono-1,4-lactone dehydrogenase.

In an embodiment of the invention, the inserted genes can encode enzymes that are involved in the biosynthesis of lactams. These compounds are cyclic amides whereas the prefixes indicate how many carbon atoms (apart from the carbonyl moiety) are present in the ring: β-lactam (2 carbon atoms outside the carbonyl, 4 ring atoms in total), γ-lactam (3 and 5), δ-lactam (4 and 6). One example for a γ-lactam is Pyrrolidone, a colorless liquid which is used in industrial settings as a high-boiling, non-corrosive, polar solvent for a wide variety of applications. It is also an intermediate in the manufacture of polymers such as polyvinylpyrrolidone and polypyrrolidone.

In an embodiment of the invention, the inserted genes can encode enzymes that are involved in the biosynthesis of ethers. Ethers are a class of organic compounds that contain an ether group—an oxygen atom connected to two alkyl or aryl groups—of general formula:

R—O—R.

A well-known example is Tetrahydrofuran (THF), a colorless, water-miscible organic liquid. This heterocyclic compound is one of the most polar ethers with a wide liquid range, it is a useful solvent. Its main use, however, is as a precursor to polymers.

One example for the natural occurring ethers are the divinyl ether oxylipins. The main enzymes involved in their biosynthesis are the lipoxygenase and especially the divinyl ether synthase.

In an embodiment of the invention, the inserted genes can encode enzymes that are involved in the biosynthesis of alkanes. Alkanes (also known as saturated hydrocarbons) are chemical compounds that consist only of the elements carbon (C) and hydrogen (H) (i.e., hydrocarbons), wherein these atoms are linked together exclusively by single bonds (i.e., they are saturated compounds). Each carbon atom must have 4 bonds (either C—H or C—C bonds), and each hydrogen atom must be joined to a carbon atom (H—C bonds). The simplest possible alkane is methane, $CH_4$. There is no limit to the number of carbon atoms that can be linked together. Alkanes, observed throughout nature, are produced directly from fatty acid metabolites. A two-gene pathway widespread in cyanobacteria is responsible for alkane biosynthesis and can be included in the first recombinant genes. An acyl-ACP reductase (EC: 1.3.1.9) converts a fatty acyl-ACP into a fatty aldehyde that is subsequently converted into an alkane/alkene by an aldehyde decarbonylase (EC: 4.1.99.5).

In an embodiment of the invention, the inserted genes can encode enzymes that are involved in the biosynthesis of a biopolymer molecule. Biopolymers such as polyhydroxyalkanoates or PHAs are linear polyesters produced in nature by bacterial fermentation of sugar or lipids. They are produced by the bacteria to store carbon and energy. The simplest and most commonly occurring form of PHA is the fermentative production of poly-3-hydroxybutyrate (P3HB) but many other polymers of this class are produced by a variety of organisms: these include poly-4-hydroxybutyrate (P4HB), polyhydroxyvalerate (PHV), polyhydroxyhexanoate (PHH), polyhydroxyoctanoate (PHO) and their copolymers. The main enzymes involved in PHA synthesis are as follows: For P3HB synthesis two molecules of acetyl-CoA were condensed by a β-ketothiolase (EC:2.3.1.9) to synthesize acetoacetyl-CoA, which is converted to (R)-3-hydroxybutyryl-CoA (3HBCoA) by NADPH-dependent acetoacetyl-CoA reductase (EC:1.1.1.36). The 3HBCoA is subsequently polymerized by poly(3-hydroxyalkanoate) synthase (EC:2.3.1.-) and converted to (P3HB).

In an embodiment of the invention, the inserted genes can encode enzymes that are involved in the biosynthesis of esters. The simple esters with lower chain alcohols (methyl-, ethyl-, n-propyl-, isopropyl- and butyl esters) are used as emollients in cosmetics and other personal care products and as lubricants. Esters of fatty acids with more complex alcohols, such as sorbitol, ethylene glycol, diethylene glycol and polyethylene glycol are consumed in foods, personal care, paper, water treatment, metal working fluids, rolling oils and synthetic lubricants. Fatty acids are typically present in the raw materials used for the production of biodiesel. A fatty acid ester (FAE) can be created by a transesterification reaction between fats or fatty acids and alcohols. The molecules in biodiesel are primarily fatty acid methyl esters FAMEs, usually obtained from vegetable oils by transesterification with methanol. The esterification of the ethanol with the acyl moieties of coenzyme A thioesters of fatty acids can be realized enzymatically by an unspecific long-chain-alcohol O-fatty-acyltransferase (EC 2.3.1.75) from *Acinetobacter baylyi* strain ADP1.

Cyanobacterial host cells according to certain embodiments of the invention can comprise a whole sequence of recombinant genes coding for proteins for the production of the chemical compound in the case that a cascade, for example of different enzymes, is necessary to produce the chemical compound. In particular, the first protein encoded by the first recombinant gene can produce a first intermediate which is further converted by the second protein encoded by the second recombinant gene into another second intermediate, which then in turn is further converted by a third protein encoded by a third recombinant gene into a third intermediate, so that a sequence of consecutive recombinant biocatalysts, which provide intermediates for the next recombinant enzyme for the production of the chemical compound can be introduced into the cyanobacterial host cell.

According to an embodiment of the invention, the compound can be an alcohol or an alkanol, particularly ethanol. In an embodiment, genes that are involved in expression of a marker protein, such as GFP, are inserted into the vector. Genes involved in the biosynthetic pathway for the production of other compounds can be inserted into the vector. Additional information on the compounds that can be produced from cyanobacteria can be found, for example, in PCT/EP2009/000892, filed Feb. 9, 2009, and in PCT/EP2009/060526, filed Aug. 13, 2009, both of which are incorporated by reference herein in their entirety.

In an embodiment, the compounds of interest that are produced from the recombinant cyanobacteria can be removed from the culture medium continuously or intermittently as the culture grows, or the compounds can be separated at the end of a batch growth period. The cultures can be grown indoors, or can be grown outdoors in enclosed containers such as plastic or glass bioreactors, or in another suitable type of container.

In an embodiment of the invention, the shuttle vector comprises one or more genes that encode enzymes involved in the biosynthetic pathway for ethanol production.

Codon Optimization of the Inserted Sequences

At least some of the nucleic acid sequences to be expressed in the cyanobacterial cell can be codon optimized for optimal expression in the target cyanobacterial strain. The underlying rationale is that the codon usage frequency of highly expressed genes is generally correlated to the host cognate tRNA abundance. (Bulmer, Nature 325:728-730; 1987). In an embodiment, the codon optimization is based on the *cyanobacterium Cyanobacterium* sp. ABICyano1 (as well as its close relative species) codon usage frequency (host codon bias), in order to achieve desirable heterologous gene expression (Sharp et al., Nucleic Acids Res. 15:1281-1295).

The codon optimization can be performed with the assistance of publicly available software, such as Gene Designer (DNA 2.o). Additional modifications to minimize unwanted restriction sites, internal Shine-Dalgarno sequences, and other sequences such as internal termination sequences and repeat sequences can also be performed. These general codon-optimization methods have been shown to result in up to approximately 1000 fold higher expression of heterologous genes in target organisms (Welch et al., PLoS One 4, e7002; 2009; and Welch et al., Journal of the Royal Society; Interface 6 (Suppl 4), S467-S476; 2009).

Accordingly, in an embodiment of the invention, the nucleic acid sequences of the inserted genes are modified so that they will have optimal expression in cyanobacteria. For example, the selectable marker gene that encodes spectinomycin resistance (nucleic acid SEQ ID NO: 30; amino acid SEQ ID NO: 31) was codon optimized for higher expression in cyanobacteria (nucleic acid SEQ ID NO: 7; amino acid SEQ ID NO: 8). The gene that encodes the GFP marker (nucleic acid SEQ ID NO: 14) was also codon optimized for higher expression in cyanobacteria using this method (nucleic acid SEQ ID NO: 12; amino acid SEQ ID NO: 13).

Transformation Methods

Figure 4:
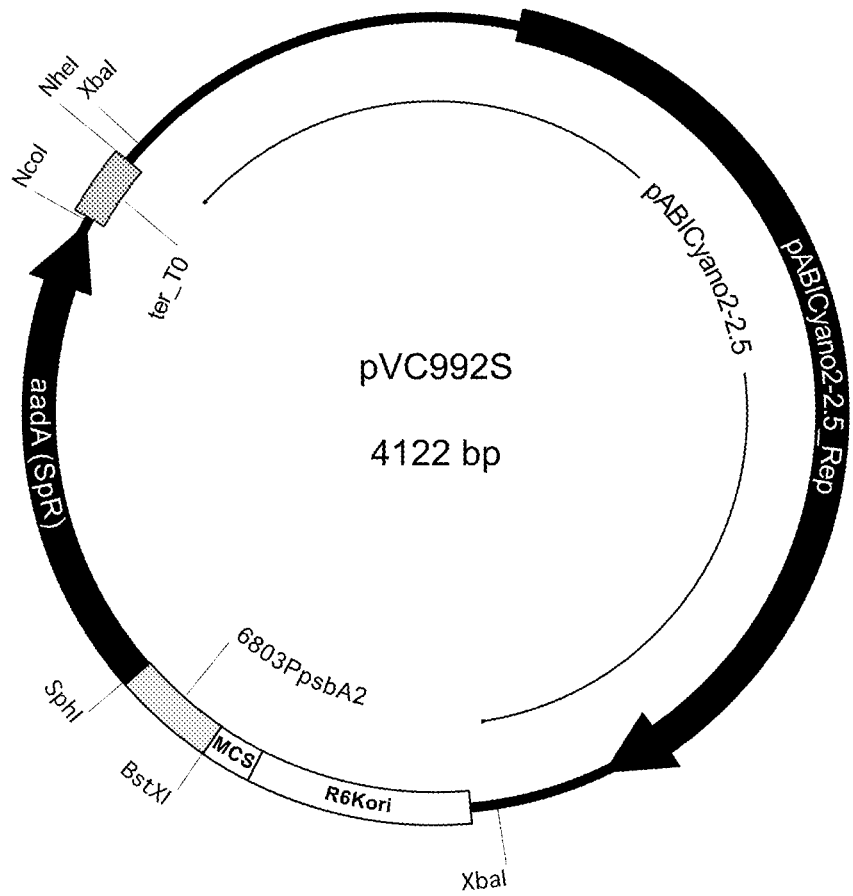
FIG. 4 is a map of the 4122 bp "pVC992S" plasmid construct (SEQ ID NO: 6). The map indicates the location of the spectinomycin resistance gene (aadA; nucleic acid SEQ ID NO: 7; amino acid SEQ ID NO: 8), driven by a promoter derived from the PCC 6803 psbA2 gene (SEQ ID NO: 9), an *E. coli* origin of replication site (R6KOri; SEQ ID NO: 10), the parent plasmid isolated from *Cyanobacterium* sp. ABI-Cyano2, including the open reading frame (ORF1) encoding the putative plasmid replication factor. MCS: multiple cloning site.
Figure 5:
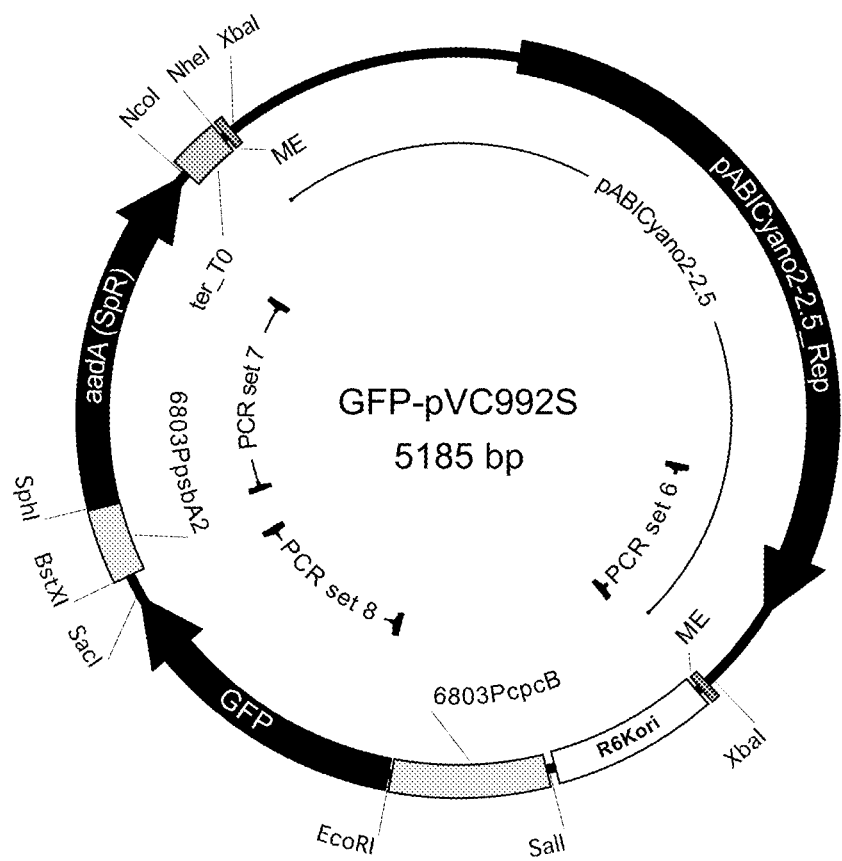
FIG. 5 is a map of the 5185 bp plasmid "GFPopti-pVC992S (SEQ ID NO: 11). This plasmid contains pVC992S as the parental vector, but additionally contains a GFPmut2 gene (nucleic acid SEQ ID NO: 12; amino acid SEQ ID NO: 13), which is a codon-optimized version of the original GFPmut2 (SEQ ID NO: 14). The sequence has been codon-optimized for expression in cyanobacteria, driven by a phycocyanin beta subunit (cpcB) promoter (SEQ ID NO: 16) that originated from *Synechocystis* strain PCC 6803. The location of the recognition sites of several restriction enzymes chosen for the modular design is shown. Specific PCR primer sets that were used to test various components of the vector are shown on the map. The two mosaic end (ME) sites for in vivo transposition are also indicated.
Figure 6:
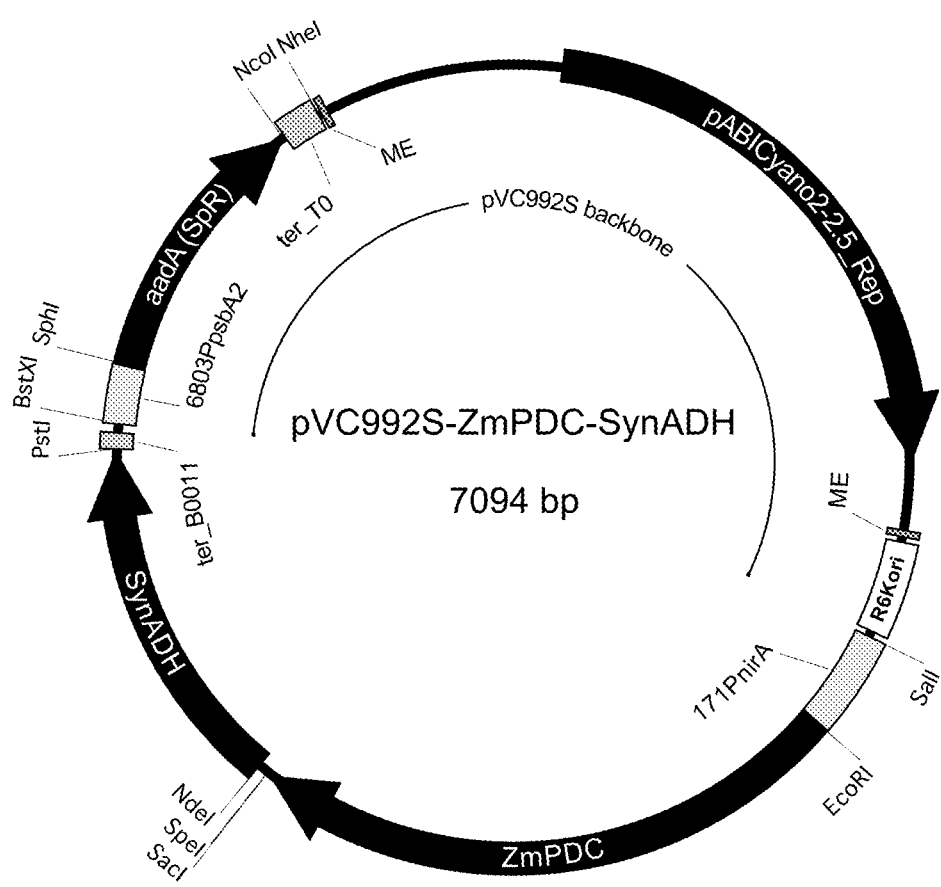
FIG. 6 is a plasmid map of one example of the ethanologenic shuttle vectors that carry the pdc and adh gene cassette on the pVC992S plasmid backbone. Both ZmPDC and SynADH are the codon-optimized version of the original PDC and ADH genes from *Zymomonas mobilis* and *Synechocystis* sp. PCC 6803, respectively, driven by a PnirA promoter derived from *Cyanobacterium* sp. ABICyano1.

The transformation of the shuttle vector to the host cell can utilize any of several methods, such as natural transformation, conjugation (bi- or tri-parental mating), electroporation, or any other suitable methods. Certain genera of cyanobacteria, such as *Synechocystis* and *Synechococcus*, can be transformed by natural uptake of exogenous DNA. In addition to electroporation, the vector can be modified to allow for integration into the cyanobacterial chromosome by adding an appropriate DNA sequence homologous to the target region of the host genome, or through in vivo transposition by introducing the mosaic ends (ME) to the vector (FIG. 4). The ABICyano2 p2.5/R6kori-based shuttle vector can also be modified to allow for conjugal transformation by adding the OriT or OriVT bom site derived from pBR322.

Once the plasmid is established in the host cell, it can be present, for example, at a range of from 1 to many copies per cell. In an embodiment, from 1, 5, 10, 20, 30, 40, 50, 60, 70, 80, 90, 100, 110, 150, 175, or 200 plasmid copies are present in each of the transformed host cells.

Selecting for Successful Transformation

The presence of the new vector in the transformed cell can be selected for using any suitable means, such as an antibiotic resistance system. For example, the vector can comprise a foreign gene conferring antibiotic resistance. The presence of the vector in the transformed host cell can be selected for by placing the putative transformed cells into an amount of the corresponding antibiotic, and harvesting the cells that survive.

Determination of the Production of the Reporter Protein GFP in Cyanobacterial Cultures In an embodiment, the foreign gene to be carried by the new vector is a reporter gene. The presence of the reporter gene and the protein it encodes can be determined in many ways. For example, the presence of the gene encoding the GFP protein in the vector and its production in the cyanobacterial cell can be confirmed by visualization using a fluorescence microscope fitted with an FITC fluorescence filter set. Other reporters can be confirmed by following the manufacturer's instructions or by following procedures commonly known in the art.

Host Cyanobacterial Strains

The vector of the invention can be used to transform many cyanobacterial species. Several exemplary host cyanobacterial strains are discussed below.

*Cyanobacterium* sp. "ABIcyano1" refers to a proprietary strain of the genus *Cyanobacterium*. A deposit of the Algenol Biofuels Inc. proprietary strain of *Cyanobacterium* sp., strain ABICyano1, disclosed herein and recited in the appended claims has been made with the American Type Culture Collection (ATCC), 10801 University Boulevard, Manassas, Va. 20110. The date of deposit was Nov. 9, 2012. The ATCC Accession Number is #PTA-13311. The deposit includes 25 2-ml vials, each containing about 1.5 ml of cryopreserved cyanobacterial cells at a concentration of about $2.39 \times 10^7$ cells per mL. All restrictions will be removed upon granting of a patent, and the deposit is intended to meet all of the requirements of 37 C.F.R. §§1.801-1.809. The deposit will be maintained in the depository for a period of thirty years, or five years after the last request, or for the enforceable life of the patent, whichever is longer, and will be replaced as necessary during that period.

This strain (*Cyanobacterium* sp. "ABIcyano1") is tolerant of high light intensities and high temperatures. The strain also grows relatively quickly, and is relatively resistant to contamination by microorganisms. The strain tolerates a wide range of salinities. The strain contains an endogenous, 6.8 kb plasmid. Because of its hardiness, this strain may be a good choice of a cyanobacterial host organism for scale-up production of products such as ethanol from recombinant genes. However, the strain has been difficult to transform using traditional cyanobacterial transformation methods.

PCC 6803 refers to a strain of *Synechocystis* sp. The strain is publicly available through ATCC as ATCC strain designation number #27184.

PCC 7002 refers to a strain of *Synechococcus* sp. The strain is publicly available through ATCC as ATCC strain designation number #27264.

PCC 7942 (*Synechococcus elongatus*) refers to another strain of *Synechococcus* sp. The strain is publicly available through ATCC as ATCC strain designation number #33912.

The novel plasmid vector of the invention is capable of transforming and replicating in several different types of cyanobacteria. Exemplary cyanobacterial genera that can be transformed with the nucleic acids described herein include, but are not limited to, *Synechocystis, Synechococcus, Acaryochloris, Anabaena, Thermosynechococcus, Chamaesiphon, Chroococcus, Cyanobacterium, Cyanobium, Dactylococcopsis, Gloeobacter, Gloeocapsa, Gloeothece, Microcystis, Prochlorococcus, Prochloron, Chroococcidiopsis, Cyanocystis, Dermocarpella, Myxosarcina, Pleurocapsa, Stanieria, Xenococcus, Arthrospira, Borzia, Crinalium, Geitlerinema, Halospirulina, Leptolyngbya, Limnothrix, Lyngbya, Microcoleus, Cyanodictyon, Aphanocapsa, Oscillatoria, Planktothrix, Prochlorothrix, Pseudanabaena,*

*Spirulina, Starria, Symploca, Trichodesmium, Tychonema, Anabaenopsis, Aphanizomenon, Calothrix, Cyanospira, Cylindrospermopsis, Cylindrospermum, Nodularia, Nostoc, Chlorogloeopsis, Fischerella, Geitleria, Nostochopsis, Iyengariella, Stigonema, Rivularia, Scytonema, Tolypothrix, Cyanothece, Phormidium, Adrianema*, and the like.

Post Transformation Confirmation Methods and Characterization

Examples 11 and 12 demonstrate how the presence of the desired plasmid construct in the host cell can be confirmed using PCR. Other methods may also be used. Examples include transcript analysis to confirm the presence and expression of the added genes, a western blot to confirm the presence of the new protein, fluorescence microscopy to confirm the presence of the GFP marker gene or its variants, and survival in the presence of an antibiotic to confirm the presence of the selectable marker.

As mentioned above, the presence of a foreign gene encoding antibiotic resistance can be determined by adding a suitable amount of the corresponding antibiotic to the culture medium. The successful transformation of a fluorescent reporter gene, such as a "marker gene" such as GFP or a variant thereof can be determined by viewing the cells under a fluorescence microscope following the manufacturer's instructions for the specific reporter gene. For example, the presence of GFPmut2 can be determined using a FITC filter set (approximately 488 nm excitation; approximately 509 nm emission). Demonstration that other specific proteins are produced can be performed, for example, using an immunoblot. Demonstration that a transcript of interest is made in the cell can be performed, for example, using reverse transcription PCR or a northern blot.

Production of a Compound of Interest: Demonstration Using Ethanol Production

The compound of interest that is produced can be chosen from a number of compounds, wherein a biosynthetic pathway for the production of the compound in known. In an embodiment, the inserted genes are derived from the genes that are present in a biochemical pathway in a prokaryote or a eukaryote. In an embodiment, the pathway genes are derived from a prokaryote such as *E. coli*. In another embodiment, the pathway genes are derived from a eukaryotic cell, such as a yeast. The genes can be derived from one organism, or can be derived from multiple organisms. Some of the genes can be derived, for example, from a cyanobacterial cell.

In an embodiment, the vector can harbor genes for ethanol production. For example, a gene encoding a PDC enzyme, along with a gene encoding an ADH enzyme, in addition to at least one operably linked promoter, can be inserted into the vector. The cells are cultured, and ethanol can then be produced.

The ethanol that is produced can be quantitated by several methods. In one method, gas chromatography is used, following methods derived from blood alcohol quantitation methods, as described in Example 21. In another method, the ethanol can be measured by an assay that measures the amount of NADH that is formed is a chemical reaction, which is described in Example 22. In another method, ethanol is measured by a commercially available ethanol determination kit.

Cyanobacterial Growth Medium

A number of known recipes for cyanobacterial growth medium can be used. In an embodiment, BG-11 medium, shown below in Tables 1 and 2, is used for growing cyanobacteria. In an embodiment, the cyanobacterial strain is a fresh water strain, and the general medium recipe below (BG-11) is used. In another embodiment, the cyanobacterial strain is a salt-water strain, and NaCl is added to the medium as desired for growth and/or production of the product of interest.

TABLE 1

| Compound | Amount (per liter) | Final Concentration |
| --- | --- | --- |
| $NaNO_3$ | 1.5 g | 17.6 mM |
| $K_2HPO_4$ | 0.04 g | 0.23 mM |
| $MgSO_4 \cdot 7H_2O$ | 0.75 g | 3.04 mM |
| $CaCl_2 \cdot 2H_2O$ | 0.036 g | 0.24 mM |
| Citric acid | 0.006 g | 0.031 mM |
| Ferric ammonium citrate | 0.006 g | — |
| EDTA (disodium salt) | 0.001 g | 0.0030 mM |
| $NaCO_3$ | 0.02 g | 0.19 mM |
| Trace metal mix A5 | 1.0 ml | — |

TABLE 2

| Trace Metal mix A5 | Amount | Final Concentration in Working Medium |
| --- | --- | --- |
| $H_3BO_3$ | 2.86 g | 46.26 μM |
| $MnCl_2 \cdot 4H_2O$ | 1.81 g | 9.15 μM |
| $ZnSO_4 \cdot 7H_2O$ | 0.222 g | 0.772 μM |
| $NaMoO_4 \cdot 2H_2O$ | 0.39 g | 1.61 μM |
| $CuSO_4 \cdot 5H_2O$ | 0.079 g | 0.32 μM |
| $Co(NO_3)_2 \cdot 6H_2O$ | 49.4 mg | 0.170 μM |
| Distilled water | 1.0 L | — |

The present invention is further described by the following non-limiting examples. However, it will be appreciated that those skilled in the art, on consideration of this disclosure, may make modifications and improvements within the spirit and scope of the present invention.

EXAMPLES

Example 1

General Methods

In general, the manipulation of constructs as well as PCR, ligation into cloning vectors, insertion of antibiotic resistance cassettes and transformation into *E. coli* were performed using standard procedures or according to the manufacturer's instructions.

Restriction endonucleases were purchased from New England Biolabs (New England Biolabs (NEB), Ipswich, Mass.), unless otherwise noted. PCR was performed using an Eppendorf Mastercycler thermocycler (Eppendorf, Hauppauge, N.Y.), using Phusion polymerase (NEB) for high fidelity amplifications. Cloning was performed in *E. coli* using Pir-116 Electro-competent cells (Illumina/Epicentre; San Diego, Calif., USA) following the manufacturer's protocol.

BG-11 stock solution was purchased from Sigma Aldrich (Sigma Aldrich, St. Louis, Mo.). Marine BG-11 (MBG-11) was prepared by dissolving 35 g Crystal Sea Marinemix (Marine Enterprises International, Inc., MD) in 1 L water and supplementing with BG-11 stock solution. Vitamin B12 (Sigma Aldrich) was supplemented to MBG-11 to achieve a final concentration of 1 μg/L, as needed. Stock solutions of the antibiotic spectinomycin (100 mg/ml) was purchased from Teknova (Hollister, Calif.).

Example 2

Capture of the Endogenous 2.5 kb Plasmid from Cyanobacterium sp. ABICyano2

Genomic DNA from *Cyanobacterium* sp. ABICyano2 cells was extracted using a QIAGEN Genomic-tip DNA extraction kit (QIAGEN GmbH, Germany) following the manufacturer's instructions. The cyanobacterial plasmid DNA was prepared using plasmid-safe ATP-dependent DNase (Illumina/Epicentre; San Diego, Calif., USA), according to the manufacturer's instructions. The plasmid DNA was then gel-purified from agarose gel-electrophoresis. The 2.5 kb cyanobacterial endogenous plasmid was captured by an in vitro transposition reaction with EZ-Tn5 R6K γ Ori/Kan-2 transposition kit (Illumina/Epicentre; San Diego, Calif., USA).

Example 3

Sequence Characterization of the Endogenous 2.5 kb Plasmid and Preparation of a Shuttle Vector Based on the Endogenous Plasmid The sequence and size of the above-described captured 2.5 kb plasmid was confirmed and validated by PCR methods and by comparison with available genome sequence data. Preliminary sequence analysis and annotation was performed using gene prediction programs Glimmer, RAST and NCBI BLAST tools. The full length DNA sequence of the endogenous plasmid is shown in SEQ ID NO: 1. The main gene present in the plasmid is a 1629 nucleotide sequence which encodes a 542-amino acid polypeptide. The polypeptide is approximately 40% similar to the replication initiation proteins (Rep) encoded in the pCB2.4 plasmid of *Synechocystis* sp. PCC 6803 (NP_862617.1) and the pCYLM01 plasmid of *Cylindrospermum* sp. A1345 (YP_001965999.1).

The 2.5 kb endogenous plasmid was modified so that it could be used as a shuttle vector for transformation of multiple cyanobacterial species. An *E. coli* origin of replication was added for ease of manipulation of the plasmid in *E. coli*. Codon-optimized antibiotic resistance genes were prepared as shown below in Example 4. Multiple cloning sites to ease replacement and swapping of nucleic acid sequences were also added. Promoters, terminators, and ribosome binding sites were inserted (FIG. 7).

Example 4

Codon Optimization

Codon optimization of the heterologously-derived genes (such as the genes encoding GFP, antibiotic resistance genes, and the production genes, such as genes in the ethanologenic cassette) was conducted using the software Gene Designer (DNA 2.0, Menlo Park, Calif.), guided by a *Cyanobacterium* sp. ABICyano1 codon usage table derived from ribosomal proteins and highly expressed genes (such as photosynthesis genes). The resulting optimized sequences were further modified and optimized to avoid the presence of the following: 1) any known or predicted putative *Cyanobacterium* sp. ABICyano1 endonuclease restriction sites (AvaI, BsaHI, KasI, XhoI etc.); 2) internal Shine-Dalgarno sequence and RNA destabilizing sequences; 3) internal terminator sequence; 4) repeat sequence (>10 bp) (Welch et al., PLoS One 4, e7002; 2009; and Welch et al., Journal of the Royal Society; Interface 6 (Suppl 4), S467-S476; 2009).

The results of the codon analysis of various genes to be inserted is shown below in Table 3. The GC % of the optimized antibiotic resistance genes decreased from 40-53% to 33-40%, which is similar to that of the cyanobacterial strain *Cyanobacterium* sp. ABICyano1 coding genes (about 36% on average). The codon adaptation index (CAI) of the codon-optimized antibiotic resistance genes is significantly improved from less than 0.4 to greater than 0.7, which is similar to that of *Cyanobacterium* sp. ABICyano1 native genes. The codon optimized antibiotic resistance genes were aadA, which confers spectinomycin resistance (nucleic acid SEQ ID NO: 7, amino acid SEQ ID NO: 8); aphA7, which confers kanamycin/neomycin resistance (original nucleic acid SEQ ID NO: 32, amino acid SEQ ID NO: 33, codon optimized nucleic acid SEQ ID NO: 34, and codon optimized amino acid SEQ ID NO: 35); and accC1, which confers gentamycin resistance (original nucleic acid SEQ ID NO: 36, amino acid SEQ ID NO: 37, codon optimized nucleic acid SEQ ID NO: 38, and codon optimized amino acid SEQ ID NO: 39).

The codon optimized GFPmut2 gene is shown in SEQ ID NO: 12.

Regarding the PDC sequence, the original nucleic acid sequence from *Zymomonas mobilis* is shown in SEQ ID NO: 40; amino acid SEQ ID NO: 41. The codon optimized nucleic acid sequence is shown in SEQ ID NO: 42, while the translation of the codon optimized sequence is shown in SEQ ID NO: 43.

Regarding ADH, the original sequence from *Synechocystis* PCC 6803 is shown in original nucleic acid sequence from *Zymomonas mobilis* is shown in SEQ ID NO: 44; amino acid SEQ ID NO: 45). The codon optimized nucleic acid sequence is shown in SEQ ID NO: 46, while the translation of the codon optimized amino acid is shown in SEQ ID NO: 47).

The codon optimization was guided by a *Cyanobacterium* sp. ABICyano1-based codon usage table derived from ribosomal proteins and other highly expressed genes (such as the photosynthesis reaction center proteins).

TABLE 3

| Gene | Function | Source | GeneBank Accession | Original % GC | Original CAI | Optimized % GC | Optimized CAI |
|---|---|---|---|---|---|---|---|
| aadA | streptomycin adenyltransferase (StrR and SpR) | *Shigella flexneri* Plasmid R100 (Class I integron) | AP000342 | 53.0 | 0.397 | 40.7 | 0.750 |
| aphA7 | kanamycin phosphotransferase (KmR and NeoR) | *Campylobacter jejuni* 14kb plasmid | M29953 | 32.8 | 0.551 | 33.6 | 0.723 |

TABLE 3-continued

| Gene | Function | Source | GeneBank Accession | Original % GC | Original CAI | Optimized % GC | Optimized CAI |
|---|---|---|---|---|---|---|---|
| accC1 | gentamicin acetyltransferase (GmR) | *Pseudomonas aeruginosa* Plasmid R1033 (Tn1696) | X15852 | 54.3 | 0.427 | 40.6 | 0.755 |
| GFPmut2 | green fluorescent protein | GFP variant from *Aequorea victoria* | AF108217 | 43.6 | 0.498 | 35.3 | 0.670 |
| ZmPDC | pyruvate decarboxylase | *Zymomonas mobilis* | YP163095 | 52.2 | 0.498 | 39.8 | 0.774 |
| SynADH | alcohol dehydrogenase | *Synechocystis* sp. PCC 6803 (slr1192) | NP443028 | 52.7 | 0.467 | 38.8 | 0.780 |

Example 5

Construct Preparation of the GFP Vector

The codon optimized aadA gene (SEQ ID NO: 7), driven by PCC 6803 psbA2 gene promoter (SEQ ID NO: 9) was first subcloned into pVC101 (Ver.2) (SEQ ID NO: 70) at the SphI and NcoI sites. The PCR-amplified full length cyanobacteria plasmid ABICyano2-p2.5 (using primers: XbaI-ABICyano2-p2-1958F: 5'-tagttctagaAGCCCTCTTAAC-CACTGAAATATTAATTAGTTTGT-3' (SEQ ID NO: 50) and: XbaI-ABICyano2-p2-1957R: 5'-tgattcta-gaAGGGCTAATTTGGCTATTTCTTAT-TAAGAATAAATCA-3' (SEQ ID NO: 51) was then ligated with XbaI digested pVC101-Opti-aadA (SpcR) to obtain the shuttle vector pVC992S (SEQ ID NO: 6).

The codon-optimized GFPmut2 gene driven by the PCC 6803 cpcBA gene promoter (SEQ ID NO: 16), was retrofitted into pVC992S between SalI and SacI sites to obtain fluorescence shuttle vector GFP-pVC992S (SEQ ID NO: 11).

*E. coli* strain Pir-116 (Illumina/Epicentre; San Diego, Calif., USA) [F-mcrA Δ(mrr-hsdRMS-mcrBC) φ80dlacZΔM15 ΔlacX74 recA1 endA1 araD139 Δ(ara, leu) 7697 galU galK λ-rpsL (StrR) nupG pir-116(DHFR)] was used to for gene subcloning and to prepare plasmid DNA for transformation, following standard molecular biology protocols.

Example 6

Culture Growth Conditions

Culture medium: *Cyanobacterium* sp. ABICyano1 cells were grown at 30° C. in 100 ml of liquid BG-11 medium in a 250 ml Erlenmeyer flask as described earlier, supplemented with 10 mM HEPES (pH 7.5), 0.3% $Na_2S_2O_3$, and 3.5 g/L Crystal Sea (about 3 ppt salinity, termed "Cs3BG11" hereafter) with shaking at 120 rpm under constant light of about 50 µE $m^{-2}$ $s^{-1}$.

*Synechocystis* sp. PCC 6803 was grown under the same conditions as *Cyanobacterium* sp. ABICyano1 described above. *Synechococcus* sp. PCC 7002 was grown under the same conditions as above except that MBG-11 medium (BG-11 medium supplemented with 35 g/L Crystal Sea Marinemix) was used.

Example 7

Natural Transformation of *Synechococcus* Strain PCC 7002

*Synechococcus* strain PCC 7002 was transformed using natural transformation following the method of Xu et al., Methods Mol Biol. 684:273-93; 2011. Briefly, 5 µl purified plasmid DNA (0.5 µg/µl) was added to 1 ml of exponentially growing PCC 7002 cells in MBG-11 medium in a fresh, sterile tube. The cells were incubated under illumination (about 150 µE $m^{-2}$ $s^{-1}$) at 37° C. overnight with vigorous shaking.

After the incubation period, the cells were transferred to a microcentrifuge tube and centrifuged at 5,000 g for 5 minutes. The supernatant was removed, and the cells were resuspended in 1 ml MBG-11 broth. The suspension was mixed with 5 ml pre-warmed (37° C.) Top Agar (0.7% low melting Ultra Pure Agarose [Invitrogen] in MBG11 medium) and poured onto pre-warmed (37° C.) selection agar plates containing 100 µg/ml Spectinomycin. After solidification, the plates were placed under constant light at about 80-100 µE $m^{-2}$ $s^{-1}$ at 37° C. for transformants clone to appear (typically 7-14 days). The putative transformants clones were lifted and re-streaked again onto the same selection agar plates. The cells were then scaled up in liquid MBG-11 medium (containing 100 µg/ml Spectinomycin) and grown under the same conditions with shaking at 120 rpm. Putative transformants were tested further as described in Example 12, below.

Example 8

Preparation of Host Cells for Electro-Transformation

In contrast to the natural transformation described in the above example, the cyanobacterial strains *Cyanobacterium* sp. ABICyano1 and *Synechocystis* strain PCC 6803 were transformed using electro-transformation methods. To prepare electro-competent cells of strain *Cyanobacterium* sp. ABICyano1, Poly-L-lysine hydrobromide (Sigma) was added to an exponentially growing culture in BG-11 medium (Table 1 and 2) at a final concentration of 50 µg/ml in order to weaken the cell walls and sensitize the cells for electroporation. The cells were incubated under illumination (about 150 µE $m^{-2}$ $s^{-1}$) at 37° C. for 6 hours. The exponentially growing *Cyanobacterium* sp. ABICyano1 cells were then harvested by centrifugation at 5,000 g at 4° C. for 10 minutes. To further facilitate uptake of exogenous DNA, the cell pellet was resuspended in Cs3BG11 with 6% DMSO and incubated on ice for 30 minutes, then pelleted and snap-frozen in liquid nitrogen for 30 minutes.

*E. coli* strain Pir-116 (Illumina/Epicentre; San Diego, Calif., USA) [F-mcrA Δ(mrr-hsdRMS-mcrBC) φ80dlacZΔM15 ΔlacX74 recA1 endA1 araD139 Δ(ara, leu) 7697 galU galK λ-rpsL (StrR) nupG pir-116(DHFR)] was used to prepare plasmid DNA for transformation as well as for plasmid rescue from the cyanobacteria transformants in this study, following standard molecular biology protocols.

Example 9

Electro-Transformation of *Cyanobacterium* Sp. ABICyano1 and *Synechocystis* Strain PCC 6803 with the New Vector Containing a GFP Reporter Gene The frozen cyanobacterial cell pellets from Example (above) were thawed by adding 30 ml of room temperature 1 mM HEPES (pH 7.5) in order to weaken the cell wall for uptake of foreign DNA. The cells were washed again with 1 mM HEPES (pH 7.5) and ETM buffer (Electro-Transformation Buffer: 0.1 mM HEPES pH 7.5, 0.2 mM $K_2HPO_4$, 0.2 mM $MgCl_2$) by repeat centrifugation at 15,000 g for 5 minutes. The cells were further concentrated by centrifugation at 20,000 g for 5 minutes. All of the washes and centrifugations were carried out on ice or in a pre-chilled centrifuge (4° C.). The resulting cell suspension concentration typically is $3~5\times10^8$ cells $ml^{-1}$. For each electroporation procedure, 3 μg of plasmid DNA was added to 100 μl of cell concentrate and transferred into a 0.2 cm cuvette (BioRad). The electroporation was conducted at 1.8 kV/2 mm, with the capacity of 10 μF and resistance of 600Ω. The actual charge was about 1789 V with pulse time of 5.2-5.8 ms. After the electroporation procedure, the cells were resuspended and transferred into a vented culture vessel containing 15 ml Cs3BG11. The cells were incubated at 30° C. under dim light (about 20 $\mu E\ m^{-2}\ s^{-1}$) overnight. The cells were further recovered by incubating under the normal growth conditions (as aforementioned) for 24 hours. The transformants were selected on the same media agar plates (1% Bacto Agar containing Spectinomycin at 10 μg/ml) and regrown in liquid Cs3BG-11 containing up to 500 μg/ml Spectinomycin.

Example 10

Selection of Transformants

For selection of positive transformants, cells were harvested by centrifugation at 5,000 g for 10 minutes at room temperature and resuspended in 3 ml CsBG11 broth described in Example 6. The suspension was mixed with 7 ml pre-warmed (37° C.) Top Agar (0.7% low melting Ultra Pure Agarose (Invitrogen) in Cs3BG11 medium) and poured onto pre-warmed (37° C.) selection agar plates containing 10 μg/ml Spectinomycin. The cells that were subjected to electroporation without DNA were also plated onto selection plates as a control. After solidification, the plates were placed under constant light of about 80-100 $\mu E\ m^{-2}\ s^{-1}$ at 40° C. (for strain *Cyanobacterium* sp. ABICyano1 or 30° C. (for strain PCC 6803). Putative transformant clones appeared in about 7-14 days, and were then lifted and re-streaked onto the same selection agar plates. The cultures were then scaled up in liquid Cs3BG-11 medium (from 20 up to 500 μg/ml Spectinomycin) and grown under the same conditions as described above with shaking at 120 rpm.

Example 11

PCR Confirmation of Putative *Cyanobacterium* Sp. ABICyano1 and *Synechocystis* PCC 6803 Transformants To prepare the DNA templates for PCR, a 10 ml aliquot of cyanobacteria cells grown in Cs3BG11 broth containing Spectinomycin (100 μg/ml) was washed twice in cold TE buffer (Tris 10 mM, EDTA 1 mM, pH 8.0) and resuspended in 4 ml Buffer B1. The total genomic DNA was extracted using a QIAGEN Genomic-tip DNA extraction kit (QIAGEN GmbH, Germany) following the manufacturer's instructions. Three PCR primer sets were used in the PCR assay, as shown below:

The first primer set confirmed the presence of the aadA gene and its promoter, with primers 6803PpsbA2-88F: 5'-AGCTTTACAAAACTCTCAT-3' (SEQ ID NO: 52) and aadA-670R: 5'-ACGGGTTGATATTGGGCGGGTAA-3' (SEQ ID NO: 53), the expected PCR product is 761 bp;

A second primer set confirmed the presence of the shuttle vector on (ABICyano2-p2.5 Rep gene for Cyano while R6K for *E. coli*), with primers p2.5-F: 5'-TTTATTTAC-CCAAGATGAACTCCA-3' (SEQ ID NO: 54) and R6K-R: 5'-GTACTATCAACAGGTTGAACTGCT-3' (SEQ ID NO: 55), the expected amplicon is 558 bp;

Another primer set allowed the confirmation of the GFP reporter gene. The primers GFP-69F: 5'-TGGGCATAAGTTTAGTGTTTCTGGTGAA-3' (SEQ ID NO: 56) and GFP-696R: 5'-ACCATGTGTTATTCCA-GCGGCAGTA-3' (SEQ ID NO: 57) were used. The expected amplicon length is 628 bp.

All of the PCR reactions were conducted using Fusion High-fidelity Taq PCR Kit (NEB). For each of the PCR reactions, 1 μg of extracted transformant genomic DNA in a 50 μl volume was used as a template. The same quantity of extracted genomic DNA of wild-type *Cyanobacterium* sp. ABICyano1 was included as negative control. PCR mix containing no DNA served as a no template control (NTC), while 1 ng of plasmid DNA was included as a positive control. The PCR primer sets were amended at 0.5 μM for each reaction. The 35-cycle PCR program involved the following steps: denaturing at 98° C. for 15 seconds, annealing at 65° C. for 15 seconds, and extension at 72° C. for 30 seconds. The PCR reaction concluded with a final extension at 72° C. for 10 minutes. The material was then held at 4° prior to electrophoretic analyses.

Figure 8A:
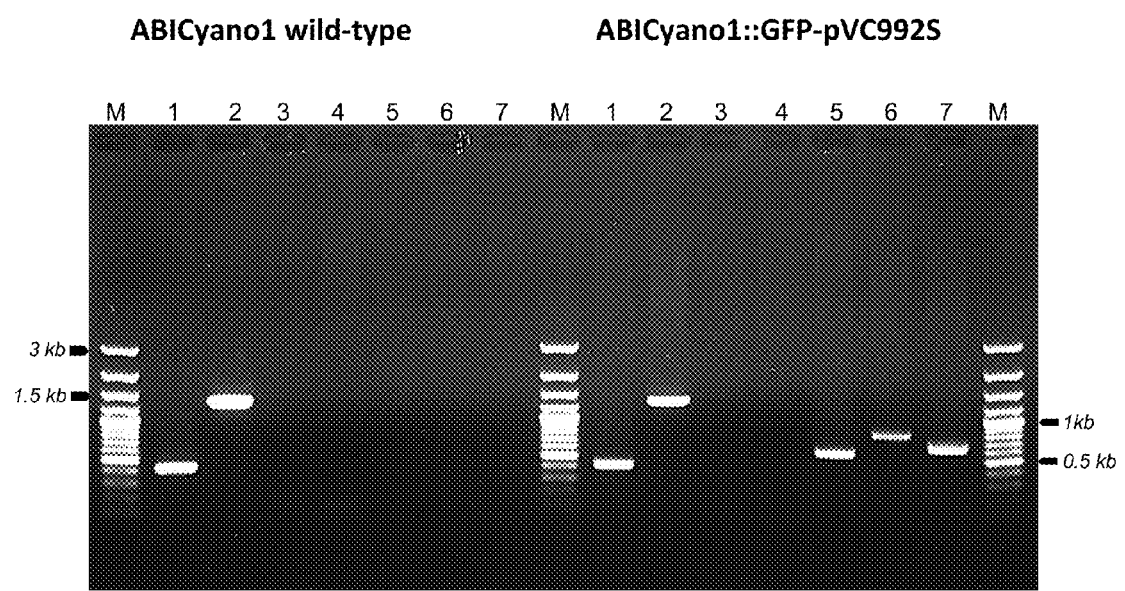
FIG. 8A through 8C is a panel of photographs of an electrophoretic DNA separation showing the PCR confirmation of the transformation of the GFP-pVC992S plasmid in cyanobacterial strains *Cyanobacterium* sp. ABICyano1 (FIG. 8A), PCC 6803 (FIG. 8B), and PCC 7002 (FIG. 8C). Specific PCR amplification of the three sets of PCR primers specific for GFP-pVC992S vector was observed for *Cyanobacterium* sp. ABICyano1, PCC 6803, and PCC 7002 transformants, but not for wild-type cells.
Figure 8B:
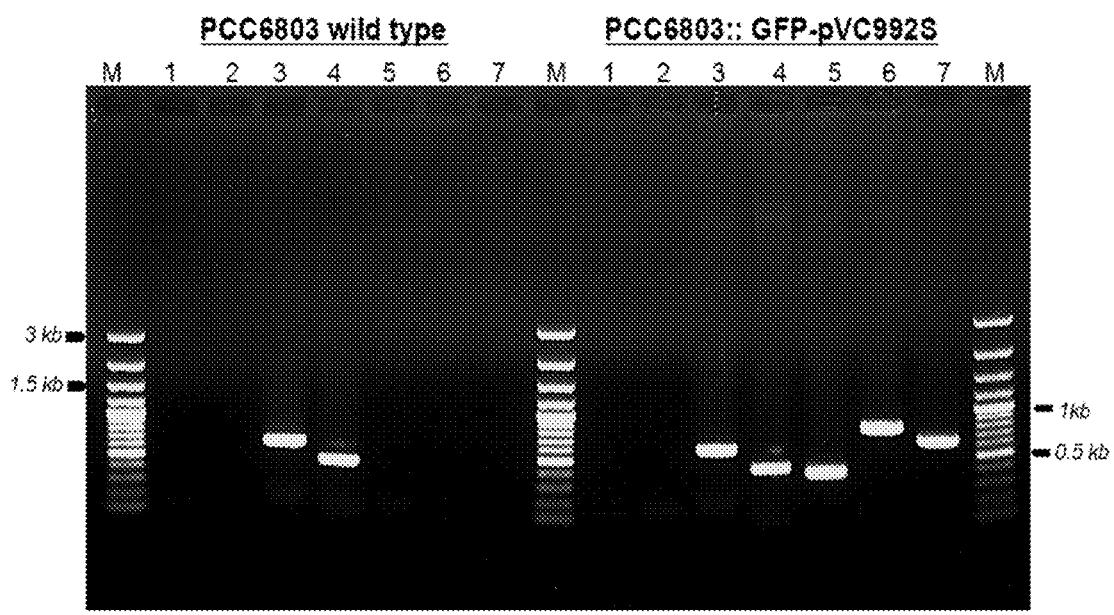

A photograph of the resulting electrophoretic separation is shown in FIGS. 8A and 8B. As shown in Table 4, below, seven sets of PCR primers were used to test *Cyanobacterium* sp. ABICyano1 wild-type or *Synechocystis* wild-type versus the GFP-pVC992S transformants: Set 1 and 2 (SEQ ID NO: 58, SEQ ID NO: 59, SEQ ID NO: 60, and SEQ ID NO: 61) are specific for the *Cyanobacterium* sp. ABICyano1 strain. Sets 3 and 4 (SEQ ID NO: 62, SEQ ID NO: 63, SEQ ID NO: 64, and SEQ ID NO: 65) are specific for *Synechocystis* PCC 6803. Sets 6-8 (SEQ ID NO: 52, SEQ ID NO: 53, SEQ ID NO: 54, SEQ ID NO: 55, SEQ ID NO: 56, and SEQ ID NO: 57) are specific for the transforming vector GFP-pVC992S.

Specific PCR amplification of the three sets of PCR primers specific for GFP-pVC992S vector was observed in *Cyanobacterium* sp. ABICyano1 and PCC 6803 transformants, but not in the wild-type cells. No cross-contamination or mixing between *Cyanobacterium* sp. ABICyano1 and PCC 6803 transformants occurred, as indicated by a strain-specific PCR test.

Example 12

PCR Confirmation of *Synechococcus* 7002 Transformants

Figure 8C:
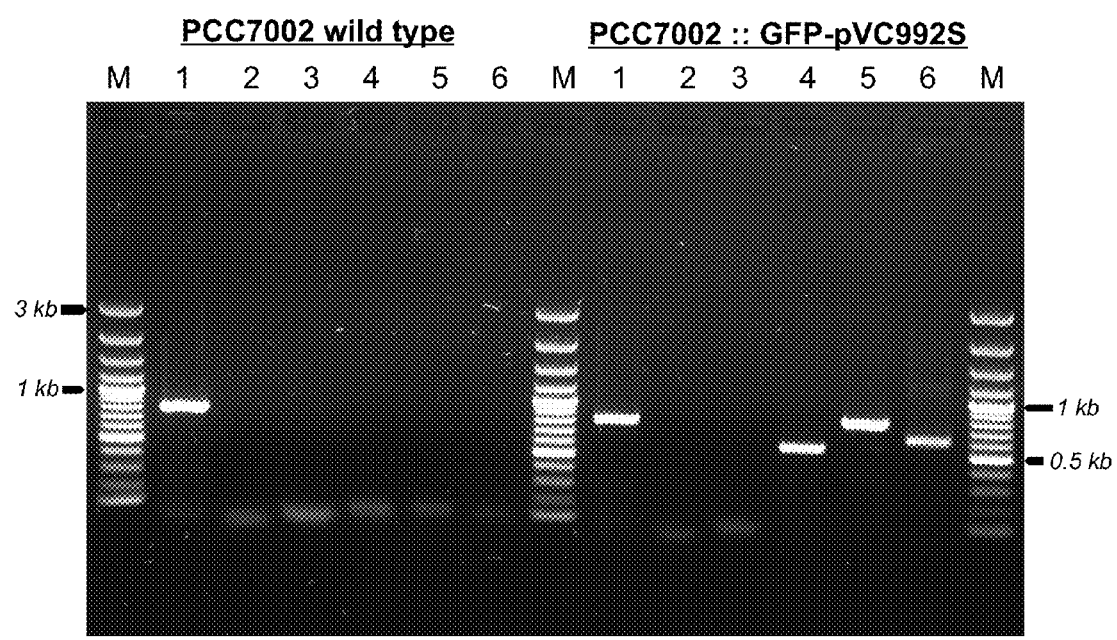

To prepare the DNA templates for PCR confirmation of the transformation of *Synechococcus* PCC 7002, a 10 ml aliquot of cyanobacteria cells grown in Cs3BG11 broth containing Spectinomycin (100 μg/ml) was washed twice in cold TE buffer (Tris 10 mM, EDTA 1 mM, pH 8.0) and resuspended in 4 ml Buffer B1, the total genomic DNA was extracted using a QIAGEN Genomic-tip DNA extraction kit (QIAGEN GmbH, Germany) following the manufacturer's instructions. A photograph of the resulting electrophoretic separation is shown in FIG. 8C. Six sets of PCR primers were used to test PCC 7002 wild-type and GFP-pVC992S transformants, as shown below in Table 4: Set 2 is specific for *Cyanobacterium* sp. ABICyano1; Set 3 is specific for PCC 6803; Set 5 is specific for PCC 7002; Sets 6-8 are specific for the transforming vector GFP-pVC992S.

Specific PCR amplification of the three sets of PCR primers specific for the GFP-pVC992S vector was observed for PCC 7002 transformants, but not for wild-type cells. No strain-contamination was observed for the PCC 7002 cells, as indicated by strain-specific PCR test (Sets 2, 3, and 5).

Figure 9:
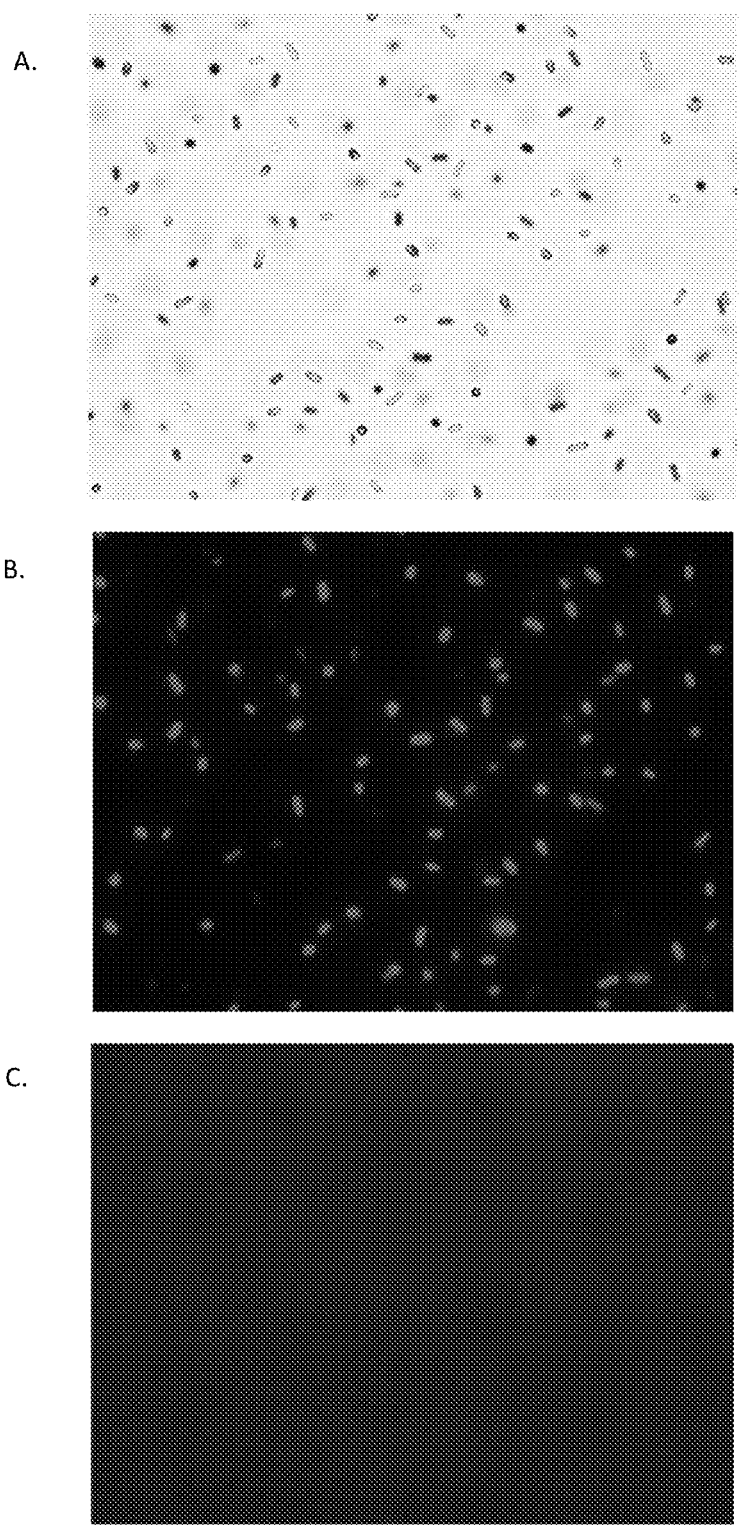
FIG. 9 is a panel of three microscope images of the negative control *Cyanobacterium* sp. ABICyano1 cells transformed with a non-GFP vector. Panel A: a light microscope image of the *Cyanobacterium* sp. ABICyano1 cells; Panel B: Microscopic image of the cyanobacterial cells using the TRITC filter which indicates chlorophyll fluorescence; Panel C: Microscopic image using an FITC filter for GFP fluorescence. The lack of fluorescence confirms that there is no visualization of fluorescent cells in the negative control.
Figure 10:
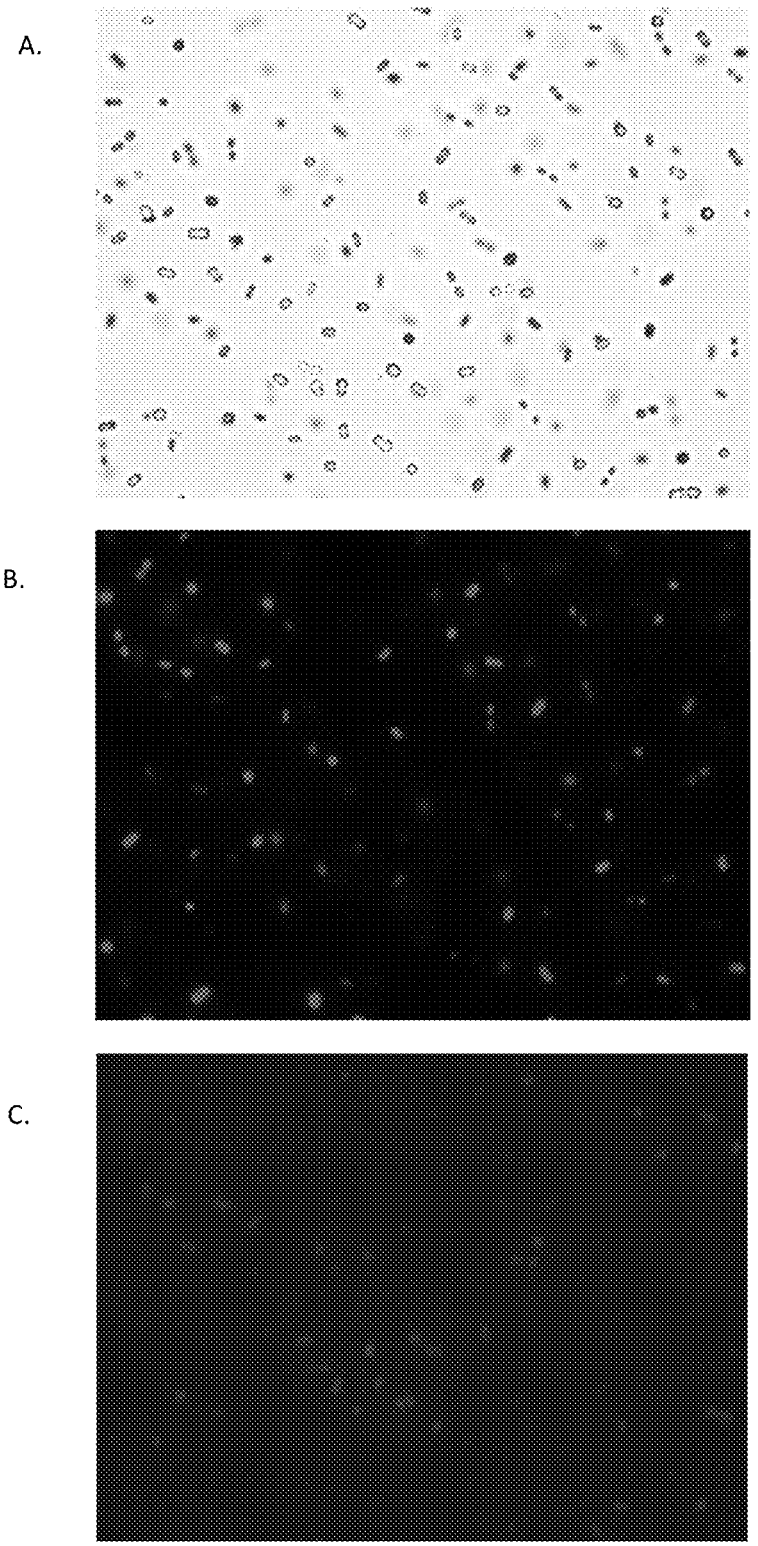
FIG. 10 is a panel of three microscope images of the *Cyanobacterium* sp. ABICyano1 cells transformed with the GFP vector. Panel A: a light microscope image; Panel B: Microscopic image using the TRITC filter which indicates chlorophyll fluorescence; Panel C: FITC filter to visualize GFP fluorescence. Several GFP-positive cells can be seen in the photograph.
Figure 11:
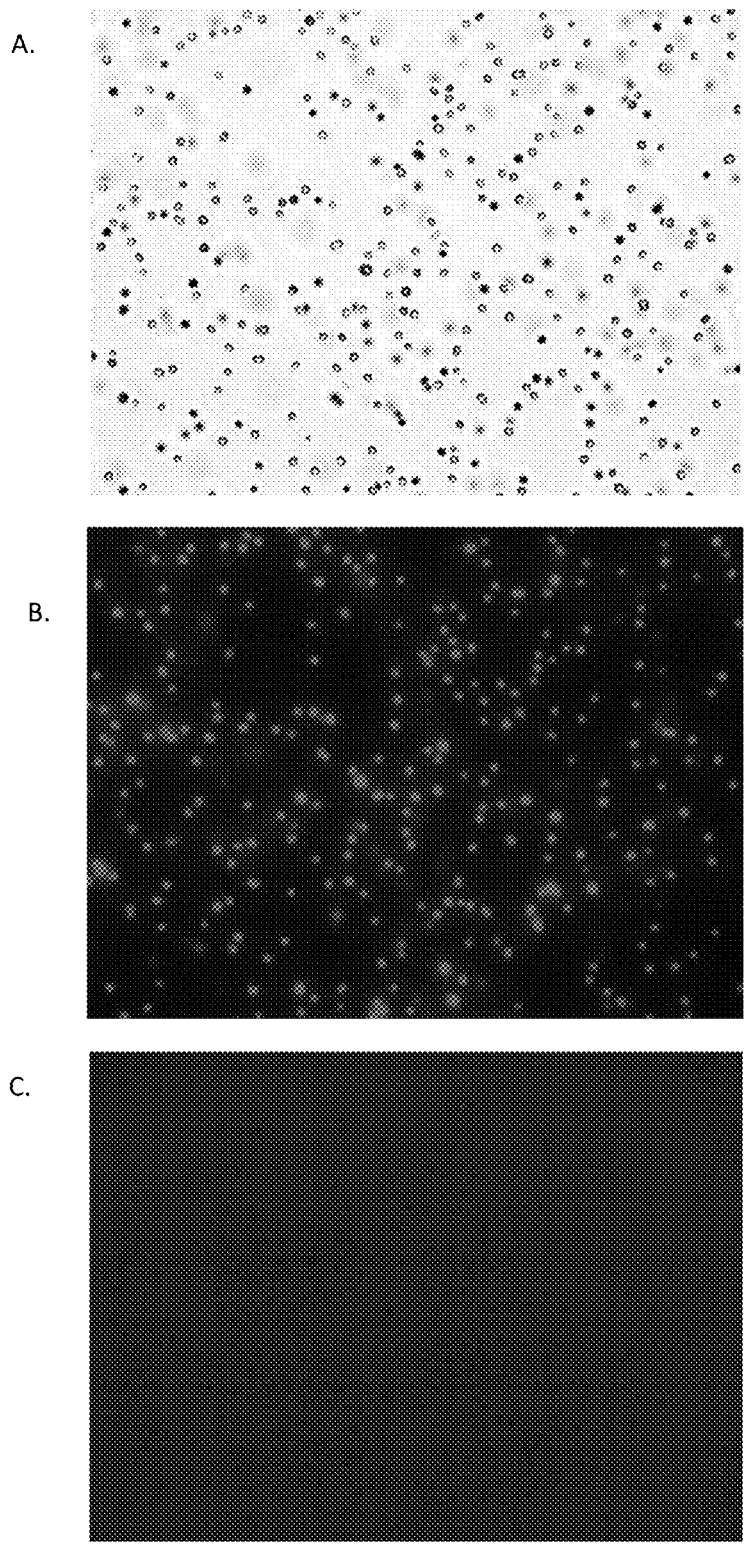
FIG. 11 is a panel of three microscope images of the negative control *Synechocystis* sp. 6803 cells transformed with a non-GFP vector. Panel A: a light microscope image; Panel B: Microscopic image of the cyanobacterial cells using the TRITC filter which indicates chlorophyll fluorescence; Panel C: Microscopic image using an FITC filter for GFP fluorescence. The lack of fluorescence confirms that there is no visualization of fluorescent cells in the negative control.

Cs3BG11 medium containing spectinomycin 100 μg/ml for 2 weeks (FIG. 10) was further confirmed via epifluorescence microscopy and compared with a reference transformed strain grown under the same conditions (FIG. 9). Panel A: bright light. Panel B: Visualization of chlorophyll using the TRITC filter set. Panel C: FITC filter set for GFP fluorescence visualization. Compared with wild-type cells, *Cyanobacterium* sp. ABICyano1:GFP-pVC992S cells emitted a strong fluorescence signal under FITC excitation/emission filter (FIG. 10C).

Example 15

GFP Protein Production in *Synechocystis* sp. PCC 6803 Transformants

Figure 12:
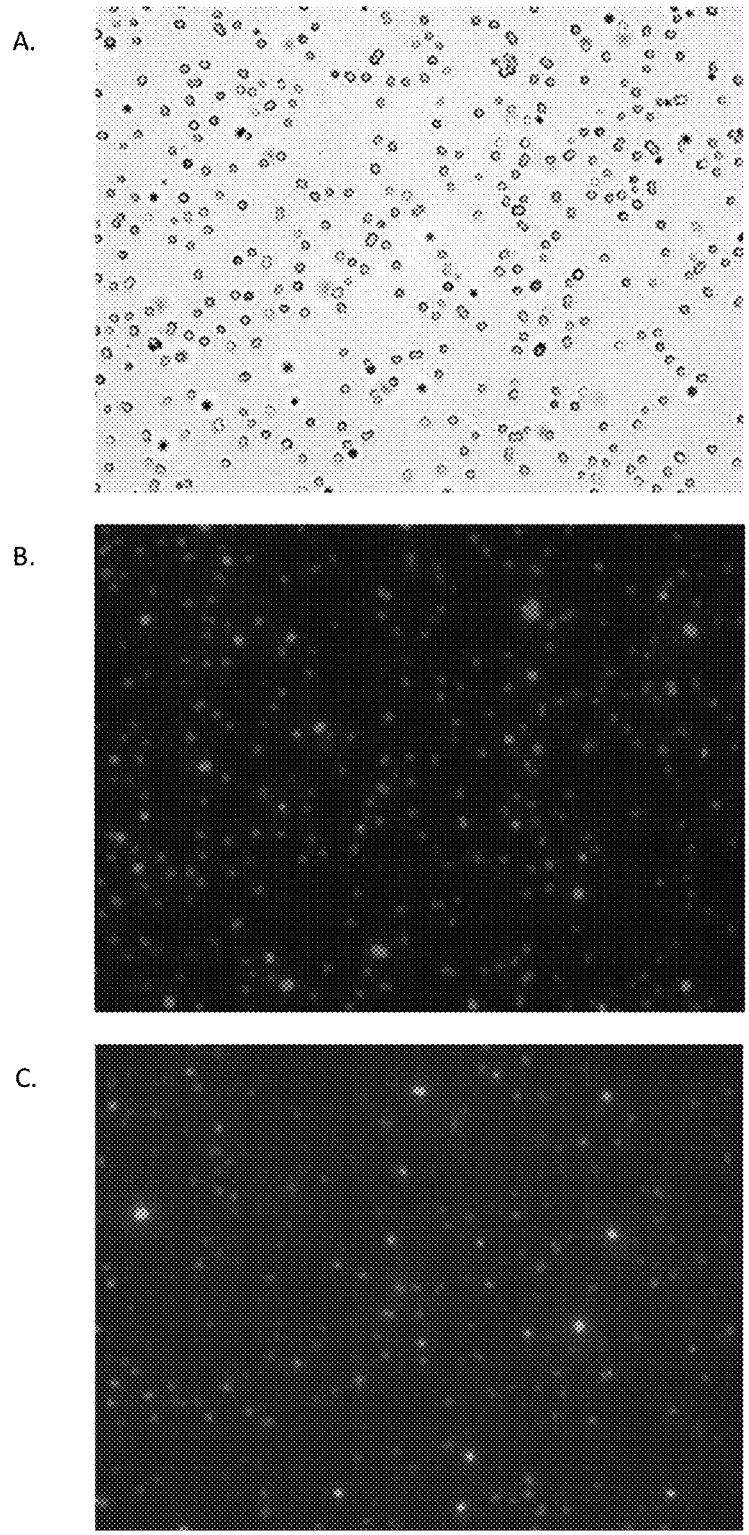
FIG. 12 is a panel of three microscope images of the *Synechocystis* sp. PCC 6803 cells transformed with the GFP vector. Panel A: a light microscope image; Panel B: Microscopic image using the TRITC filter which indicates chlorophyll fluorescence; Panel C: FITC filter to visualize GFP fluorescence. Several GFP-positive cells can be seen in the photograph.

The expression of codon-optimized GFPmut2 gene in *Synechocystis* sp. PCC 6803 transformants (FIG. 12) was

TABLE 4

PCR Primers for Confirmation of Transformation of *Cyanobacterium* sp. ABICyano1, *Synechocystis* sp. PCC 6803, and *Synechococcus* sp. PCC 7002

| Set # | Target | Primer Name | Sequence (5'-3') | SEQ ID NO: | Amplicon Size (bp) | Specificity |
|---|---|---|---|---|---|---|
| 1 | PpetE | PpetE-ABICyano1-F | CCGTCGACGAGAAGGGGAACAG | 58 | 392 | *Cyanobacterium* sp. ABICyano1 |
|   |       | PpetE-ABICyano1-R | CCGAATTCATTGTGTTTTTTTATT | 59 |     |                  |
| 2 | p6.8_Rep | p6.8-1766F | TGCCGTCAAAAGGTAAAGGAATA | 60 | 1278 | *Cyanobacterium* sp. ABICyano1 |
|   |          | p6.8-3044R | GTCTCAAGCCAAATGCCGTGCGA | 61 |     |                  |
| 3 | 6803PpsaA | 6803PpsaA-F | TCAACCAAGGGTTTTTAACCTCC | 62 | 569 | PCC 6803 |
|   |           | 6803PpsaA-R | GCAGGGTTCTCCTCGCTCGACAA | 63 |     |          |
| 4 | 6803Adh | Adh-102F | GTATTGTGGGTGTGCCACAGTG | 64 | 418 | PCC 6803 |
|   |         | Adh-519R | AATGCCGATCACTGCCACTTTTG | 65 |     |          |
| 5 | 7002pAQ1 | pAQ1-2762F | AGTGGATTCTTGGCAGAACG | 66 | 794 | PCC 7002 |
|   |          | pAQ1-3555R | CAGCAGTGAAAATAGCGTATACA | 67 |     |          |
| 6 | p-2.5_Re | p2.5-F | TTTATTTACCCAAGATGAACTCC | 54 | 558 | GFP-pVC992S |
|   |          | R6K-R | GTACTATCAACAGGTTGAACTGC | 55 |     |             |
| 7 | aadA | 6803PpsbA2-88F | AGCTTTACAAAACTCTCAT | 52 | 761 | GFP-pVC992S |
|   |      | aadA-670R | ACGGGTTGATATTGGGCGGGTAA | 53 |     |             |
| 8 | GFPmut2 | GFP-69F | TGGGCATAAGTTTAGTGTTTCTG | 56 | 628 | GFP-pVC992S |
|   |         | GFP-696R | ACCATGTGTTATTCCAGCGGCAG | 57 |     |             |

Example 13

Plasmid Rescue and Sequence Confirmation

One microgram of extracted genomic DNA from the putative cyanobacterial transformants was introduced to Pir-116 *E. coli* cells via electroporation. The subsequent rescue clone selection and plasmid amplification followed standard molecular protocols. The rescued plasmid DNA was sequenced with eight primers to cover the full length of the vector. The sequence analyses were conducted using the SeqMan program implemented in the Lasergene 9 software package (DNAStar).

Example 14

GFP Protein Production in *Cyanobacterium* sp. ABICyano1 Transformants

The expression of codon-optimized GFPmut2 gene in *Cyanobacterium* sp. ABICyano1 transformants grown in further confirmed via epifluorescence microscopy. Panel A: bright light. Panel B: Visualization of chlorophyll using the TRITC filter set. Panel C: FITC filter set for GFP fluorescence visualization. Compared with wild-type cells, the transformed cells emitted a strong fluorescence signal under FITC excitation/emission filter (FIG. 12C).

Example 16

GFP Protein Production in *Synechococcus* sp. PCC 7002 Transformants

Figure 13:
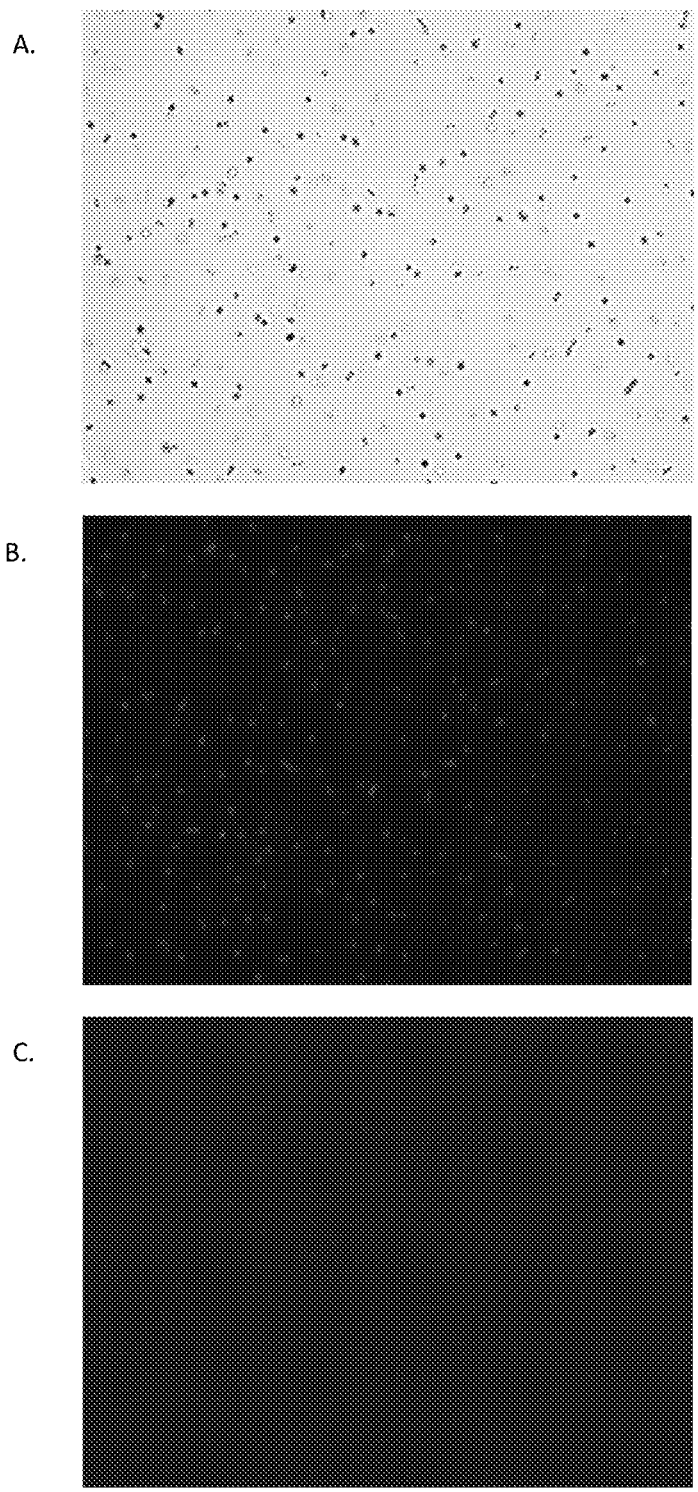
FIG. 13 is a panel of three microscope images of the negative control *Synechococcus* PCC 7002 cells transformed with a non-GFP vector. Panel A: a light microscope image; Panel B: Microscopic image of the cyanobacterial cells using the TRITC filter which indicates chlorophyll fluorescence; Panel C: Microscopic image using an FITC filter for GFP fluorescence. The lack of fluorescence confirms that there is no visualization of fluorescent cells in the negative control.
Figure 14:
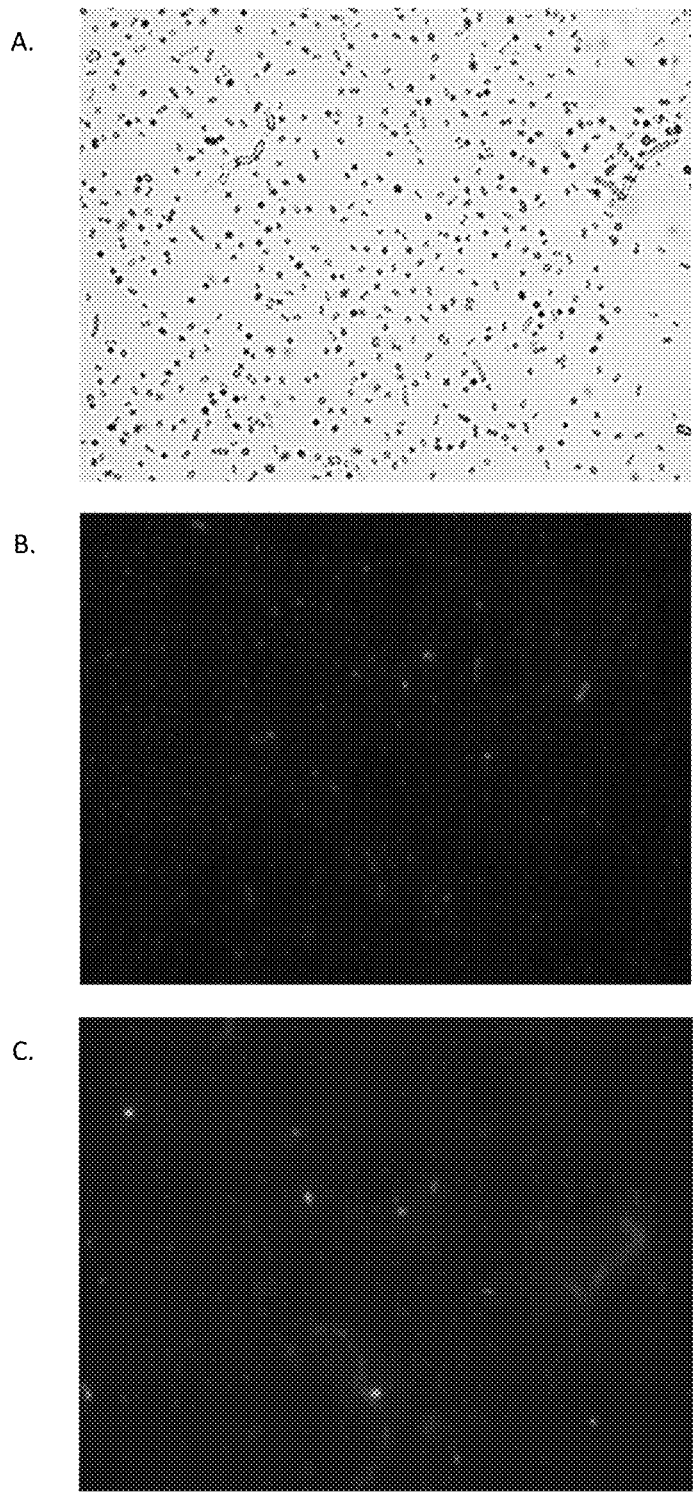
FIG. 14 is a panel of three microscope images of the *Synechococcus* sp. PCC 7002 cells transformed with the GFP vector. Panel A: a light microscope image; Panel B: Microscopic image using the TRITC filter which indicates chlorophyll fluorescence; Panel C: FITC filter to visualize GFP fluorescence. Several GFP-positive cells can be seen in the photograph.

The expression of codon-optimized GFPmut2 gene in *Synechococcus* sp. PCC 7002 transformants was further confirmed via epifluorescence microscopy (FIG. 14) and compared with a wild-type strain grown under the same conditions (FIG. 13). Panel A: bright light. Panel B: Visualization of chlorophyll using the TRITC filter set. Panel C: FITC filter set for GFP fluorescence visualization. Compared with wild-type cells, the transformed cells emitted a strong fluorescence signal under FITC excitation/emission filter (FIG. 14C), confirming that the GFP protein is produced and can successfully fluoresce in the transformant cyanobacterial cells.

Example 17

Preparation of Vector Constructs for the Production of Ethanol in Cyanobacteria

Several ethanologenic plasmid constructs were prepared using the new vector, each designed with different promoters to drive the ethanologenic genes. The ethanologenic cassette contains a gene encoding PDC and a gene encoding ADH. In an initial construct, both genes were placed under the regulatory control of the *Cyanobacterium* sp. ABICyano1 PnirA promoter (SEQ ID NO: 17). Other constructs were prepared as above, except that the promoter sequence was substituted with one of the following promoters: *Cyanobacterium* sp. ABICyano1 PlrtA (SEQ ID NO: 18), *Cyanobacterium* sp. ABICyano1 PmrgA (SEQ ID NO: 19), *Cyanobacterium* sp. ABICyano1 PnblA (SEQ ID NO: 20), *Cyanobacterium* sp. ABICyano1 PggpS (SEQ ID NO: 21), *Cyanobacterium* sp. ABICyano1 PpetJ (SEQ ID NO: 22), *Cyanobacterium* sp. ABICyano1 PcpcBA (SEQ ID NO: 69), *Cyanobacterium* sp. ABICyano1 PppsA (SEQ ID NO: 23), *Cyanobacterium* sp. ABICyano1 PrnpA (SEQ ID NO: 24), or *Cyanobacterium* sp. ABICyano1 PpstS (SEQ ID NO: 25). The constructs were confirmed using PCR.

The several above-described ethanologenic cassette constructs are transformed to Cyanobacterial host cells from several genera (*Synechocystis* PCC 6803, *Synechococcus* PCC 7002, and *Cyanobacterium* sp. ABICyano1), in order to determine the effect of each of the constructs on ethanol production among cyanobacterial species.

Example 18

Transformation of *Synechocystis* PCC 6803 with the New Vector Containing an Ethanologenic Cassette The several above-described ethanologenic cassette constructs were transformed to *Synechocystis* PCC 6803 host cells in order to confirm ethanol production in the transformed host cells. The ethanologenic gene cassettes were fitted with various promoters linked to codon-optimized versions of the genes encoding *Zymomonas mobilis*-derived PDC and *Synechocystis*-derived ADH (promoter-PDCZm-ADH6803), inserted into the new ABICyano2-based vector (SEQ ID NO: 68). The transformants were selected on BG-11 agar plates containing 10 µg/ml of spectinomycin, and were further purified by re-streaking.

Figure 15:
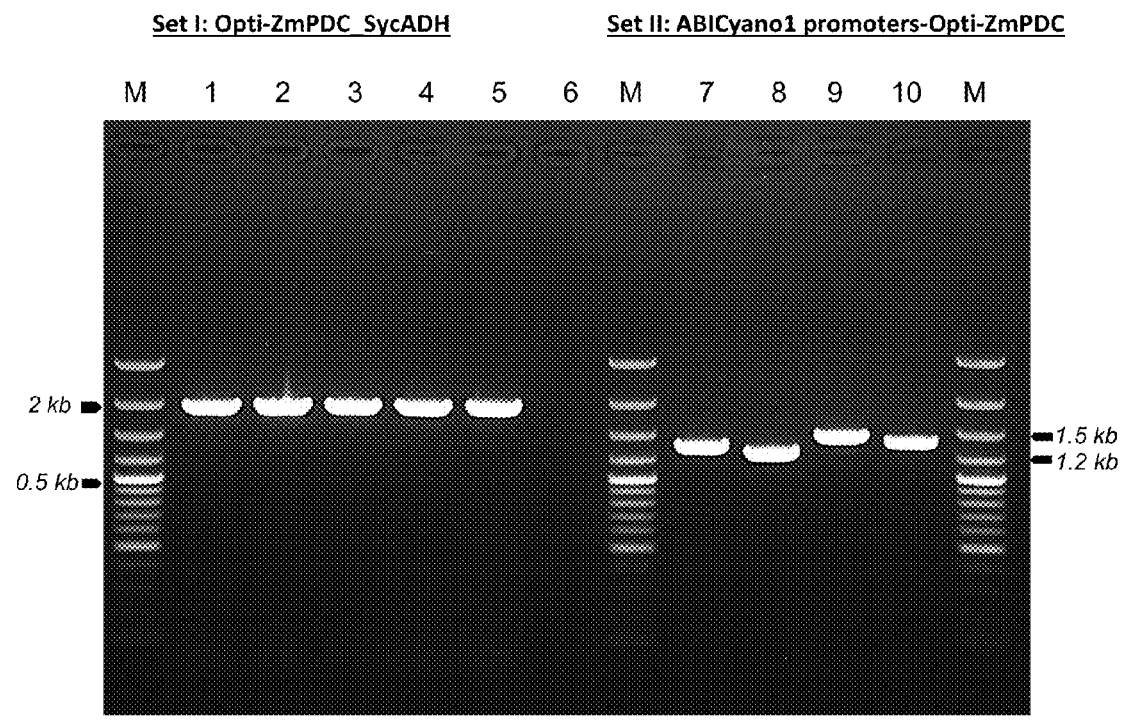
FIG. 15 is a photograph of an electrophoretic DNA separation showing the PCR confirmation of the transformation of *Synechocystis* PCC 6803 with an ABICyano2-based vector harboring an ethanologenic cassette having genes encoding PDC and ADH, linked to various promoters which were obtained from *Cyanobacterium* sp. ABICyano1. The promoters include a nirA promoter (SEQ ID NO: 17), an lrtA promoter (SEQ ID NO: 18), a ggpSA promoter (SEQ ID NO: 21), and a cpcB promoter (SEQ ID NO: 16). Lanes 1 and 7: PCC 6803::pVC221 [ABICyano1-PnirA-ZmPD-Copti_SycADHopti] transformant DNA. Lanes 2 and 8: PCC 6803::pVC222 [ABICyano1-PlrtA-ZmPDCopti_SycADHopti] transformant DNA. Lanes 3 and 9: PCC 6803::pVC225 [ABICyano1-PggpSA-ZmPDCopti_SycADHopti] transformant DNA. Lanes 4 and 10: PCC 6803::pVC227 [ABICyano1-PcpcB-ZmPDCopti_SycADHopti] transformant DNA. Lane 5: Plasmid pVC210 Ctr. [ZmPDCopti_SycADHopti, promoter less]. Lane 6: wt PCC 6803 DNA.

The transformation and ethanol production in cyanobacteria was confirmed by PCR (FIG. 15). Total DNA was extracted from the putative transformants as templates. Using primers specific to the ethanologenic genes (PDC and ADH) and the spectinomycin resistance gene as shown below in Table 5, the PCR products were amplified from the putative *Synechocystis* PCC 6803 transformants, but not from the wild-type *Synechocystis* PCC 6803 cells.

TABLE 5

PCR Primers for Confirmation of Transformation of *Synechocystis* PCC 6803 with the ABICyano2-based Vector Harboring Various Ethanologenic Cassettes

| Set # | Gene | Primer Name | Sequence (3'-->3') | SEQ ID | Tm (° C.) | Amplicon Size (bp) |
|---|---|---|---|---|---|---|
| 1 | Zm-ADHopti cassette | ZmPDCopti-552F | GTGCAGCTCCTGGACCTGCT | 71 | 69 | 1917 |
|  |  | SycADHopti-684R | GAATTTTCCCTCTGCACTAG CGAT | 72 | 67 |  |
| 2 | ABICyano1-PnirA_ZmPDCopti | ABICyano1-PnirA-280F | ACCGTACGGGTCGACAATT AATAACT | 73 | 67 | 1320 |
|  |  | ZmPDCopti-1037R | AAGAAATCGAGTGCGCCAG TCT | 74 | 68 |  |
| 3 | ABICyano1-PlrtA_ZmPDCopti | ABICyano1-PlrtA-F205 | TAGAGTATGATAAAATGAC AAGGAAAGGAT | 75 | 61 | 1240 |
|  |  | ZmPDCopti-1037R | AAGAAATCGAGTGCGCCAG TCT | 76 | 68 |  |
| 4 | ABICyano1-PggpS_ZmPDCopti | ABICyano1-PggpS-F408 | GTTGAGGTATTAATAGAGC TTGATAAATGATA | 77 | 63 | 1450 |
|  |  | ZmPDCopti-1037R | AAGAAATCGAGTGCGCCAG TCT | 78 | 68 |  |
| 5 | ABICyano1-PcpcB_ZmPDCopti | ABICyano1-PcpcB-F327 | TGAGAAAAAGTGTAAAC AAATATTAAGA | 79 | 59 | 1360 |
|  |  | ZmPDCopti-1037R | AAGAAATCGAGTGCGCCAG TCT | 80 | 68 |  |

Detection of transcription of the ethanologenic genes (PDC and ADH) and the antibiotic resistance gene in the putative transformant grown in BG-11 was then performed using RT-PCR, where cDNA was reverse-transcribed from the total RNA.

As shown in FIG. 15, the four putative transformants were confirmed to be positive for the optimized PDC and ADH ethanologenic cassette genes. PCR amplification of the codon optimized EtOH cassette (ZmPDC-SycADH) was evident for the four PCC 6803 transformants (Lanes 1-4), but not for wild-type cells (Lane 6), using the primer Set 1 (ZmPDCopti-552F and SycADHopti-684R). Lane 5: Plasmid pVC210 DNA as positive Control. These four ethanologenic transformants were further PCR confirmed by using four primer sets specific for *Cyanobacterium* sp. ABI-Cyano1 promoters (Set#2-5) driving the EtOH cassettes, as shown in Lanes 7-10.

Lanes 1 and 7: PCC 6803::pVC221 [ABICyano1-PnirA-ZmPDCopti_SycADHopti] transformant DNA. Lanes 2 and 8: PCC 6803::pVC222 [ABICyano1-PlrtA-ZmPDCopti_SycADHopti] transformant DNA. Lanes 3 and 9: PCC 6803::pVC225 [ABICyano1-PggpSA-ZmPDCopti_SycADHopti] transformant DNA. Lanes 4 and 10: PCC 6803::pVC227 [ABICyano1-PcpcB-ZmPDCopti_SycADHopti] transformant DNA. Lane 5: Plasmid pVC210 control [ZmPDCopti_SycADHopti, promoter less]. Lane 6: wild-type PCC 6803 DNA.

Example 19

Transformation of *Synechococcus* PCC 7002 with the New Vector Containing an Ethanologenic Cassette The several above-described ethanologenic cassette constructs are transformed to *Synechococcus* PCC 7002 host cells in order to confirm ethanol production in the transformed host cells. The ethanologenic gene cassettes are fitted with various promoters linked to codon-optimized versions of the genes encoding *Zymomonas mobilis*-derived PDC and *Synechocystis*-derived ADH (promoter-PDCZm-ADH6803), inserted into the new ABICyano2-based vector (SEQ ID NO: 68). The transformants are selected on BG-11 agar plates containing 10 µg/ml of spectinomycin, and are further purified by re-streaking.

The transformation and ethanol production in cyanobacteria is then confirmed by PCR. Total DNA is extracted from the putative transformants as templates. Using primers specific to the ethanologenic genes (PDC and ADH) and the spectinomycin resistance gene, the PCR products are amplified from the putative *Synechococcus* PCC 7002 transformants, but not from the wild-type *Synechococcus* PCC 7002 cells.

Example 20

Transformation of *Cyanobacterium* sp. with the New Vector Containing an Ethanologenic Cassette The several above-described ethanologenic cassette constructs are transformed to *Cyanobacterium* sp. ABICyano1 host cells in order to confirm ethanol production in the transformed host cells. The ethanologenic gene cassettes are fitted with various promoters linked to codon-optimized versions of the genes encoding *Zymomonas mobilis*-derived PDC and *Synechocystis*-derived ADH (promoter-PDCZm-ADH6803), inserted into the new ABICyano2-based vector (SEQ ID NO: 68). The transformants are selected on BG-11 agar plates containing 10 µg/ml of spectinomycin, and are further purified by re-streaking.

The transformation and ethanol production in the *Cyanobacterium* sp. ABICyano1 host cells can then be confirmed by PCR. Total DNA is extracted from the putative transformants as templates. Using primers specific to the ethanologenic genes (PDC and ADH) and the spectinomycin resistance gene, the PCR products are amplified from the putative *Cyanobacterium* sp. ABICyano1 transformants, but not from the wild-type *Cyanobacterium* sp. ABICyano1 cells. By use of this method, successful transformation is confirmed.

Example 21

Determination of Ethanol Production using Headspace Gas Chromatography with Flame Ionization Detection The *Synechocystis* PCC 6803 host cells transformed with the ethanol cassette-containing universal vector of the invention were tested to determine the level of ethanol production. A 20 ml culture of each of the four transformants was grown BG-11 medium under continuous light, with mixing set at 120 rpm, for 1 week.

A 2 ml sample of culture was taken from the 20 ml test culture when the cells were 1 week old, growing at mid-log phase ($OD_{750}$=about 1). The sample was placed into a 10 ml GC vial with a crimped top. The concentration of ethanol was determined by gas chromatography using a 0.32 mm by 30 m DB-ALC1 GC capillary column having a film thickness of 1.80 µm, using flame ionization detection on an Agilent Gas Chromatograph (Agilent Technologies, model number 7890A) configured with a headspace sampler (Agilent Technologies, model number 7697A). The method followed the manufacturer's instructions for blood alcohol quantitation (Agilent application note number 5990-9021EN, entitled "Analysis of Ethanol in Blood with the Agilent 7820A GC and 7697A headspace sampler." The samples were heated to 85° C. for 15 minutes. The N2 column flow was 12 ml/minute. The analyte concentration of each sample was determined by application of a $1/x^2$ weighted least squares linear calibration model to the measured response of each analyte.

Calibration method: The calibration model is generated by fitting the detector response of calibration standards to their known, or true, concentration. The calibration standards are prepared in volumetric glassware from ACS reagent grade (minimum 99.5% purity) ethanol and acetaldehyde at levels of 0.001, 0.01, 0.1, and 1.0% v/v. Since a sample matrix can affect analyte response, care is taken to ensure that calibration standards are prepared in an identical media/matrix as are the samples to be analyzed. Calibration is performed each time a sample set is analyzed, as is the confirmatory analysis of third-party certified reference materials. By use of this method, ethanol levels can be quantitated within the range of 0.001%-1.0% v/v within about 15% accuracy, as confirmed by analysis of third-party certified standard reference materials.

Figure 16:
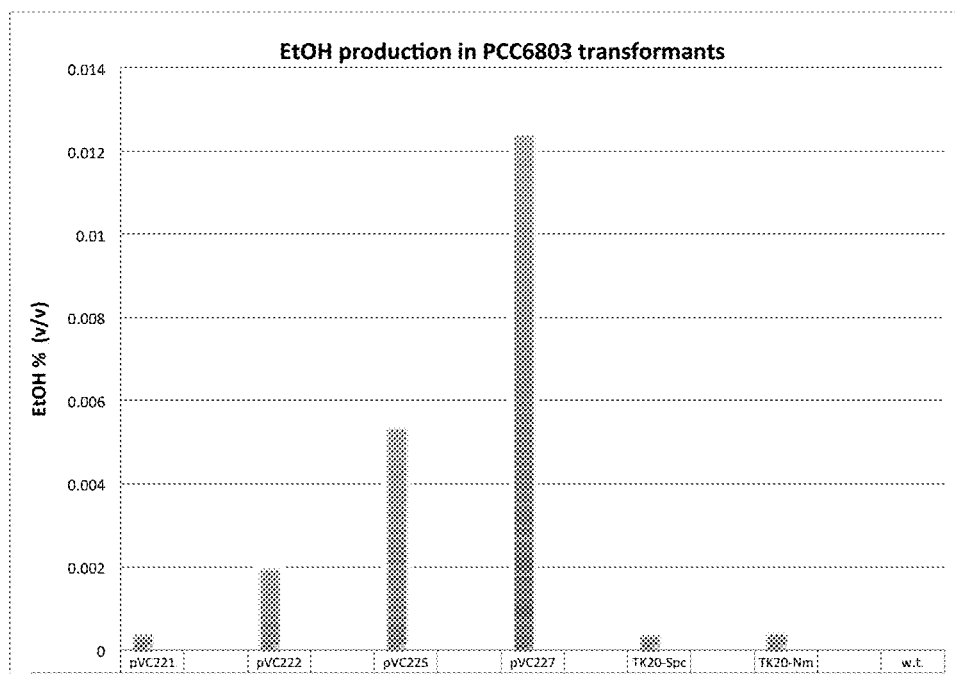
FIG. 16 is a bar graph showing the amount of ethanol production (% v/v) in *Synechocystis* PCC 6803 cells transformed with an ABICyano2-based plasmid backbone carrying various ethanologenic constructs as listed in FIG. 15. The ethanol concentration (v/v %) of four transformants (pVC221, 222, 225 and 227) was measured. The ethanol production of a control reference *Synechocystis* PCC 6803 ethanol producer (harboring vector TK20) as well as wild-type *Synechocystis* PCC 6803, were also determined.

The results of the ethanol quantitation are shown in FIG. 16. Briefly, three of the four transformants (pVC222, pVC225, and pVC227) produced a high amount of ethanol, with the most being produced by pVC227, at about 0.012% (v/v), or 0.0015% v/v per day (based on 8 days of ethanol production). Calculated differently, the ethanol produced reached about 0.2565 mmol ethanol/(liter-day).

Example 22

Determination of Ethanol Production by an Optical Enzymatic Method

The following method can also be used to determine the amount of ethanol in the cyanobacterial culture. Ethanol is measured daily during the growth experiment according to the optical enzymatic method described herein ("Ethanol UV method" test kit by Boehringer Mannheim/R-Biopharm, Darmstadt, Germany). The principle of this quantitation method is:

Reaction 1: Ethanol is oxidized by nicotinamide-adenine dinucleotide (NAD+) to acetaldehyde in a reaction which is catalyzed by the enzyme alcohol dehydrogenase (ADH).

Reaction 2: The acetaldehyde formed in the above reaction is quantitatively oxidized to acetic acid by the enzyme aldehyde dehydrogenase (Al-DH).

In reactions (1) and (2) reduced nicotinamide-adenine dinucleotide (NADH) is formed. The amount of NADH formed is proportional to the amount of ethanol in the sample. NADH is easily quantified by means of its light absorbance. The absorbance is measured at 340 nm, Hg 365 nm or Hg 334 nm.

Ethanol Quantitation Procedure: Preparation of solutions: Solution 1: 1.3 mg/ml NAD and 0.27 U aldehyde dehydrogenase in potassium diphosphate buffer, pH 9.0. Solution 2: Suspension of alcohol dehydrogenase (ADH) with approximately 4000 U/ml. Alternatively, the chemicals and solutions of the ethanol determination kit of Boehringer Mannheim/R-Biopharm (Cat. No. 10176290035) can be used.

Sample and solution 1 are mixed in a ratio of 3 ml solution 1 and 0.1 ml sample (if necessary the sample is diluted with water). After 3 minutes the absorbance is measured (A1). The reaction is then started by the addition of ADH suspension (solution 2, 0.050 ml for 3 ml solution 1 and 0.1 ml sample). After completion of the reaction (approximately 5 to 10 minutes) the absorbance is measured again (A2). The absorption measurements can be performed using a photometer or a microplate reader.

From the measured absorbance difference $\Delta A = (A2 - A1)$ the ethanol concentration in the sample is calculated with the equation:

$$c = \frac{V \times MG}{\varepsilon \times d \times v \times 2 \times 1000} \times \Delta A$$

where c=ethanol concentration [g/L]; V=total volume [mL]; MG=molecular weight of ethanol (46.07 g/mol); $\varepsilon$=extinction coefficient (6.3 L×mmol$^{-1}$×cm$^{-1}$ at 340 nm); d=light path [cm]; v=sample volume [mL]

Literature: Protocol of the kit Ethanol, UV method for the determination of ethanol in foodstuff and other materials, Cat. No. 10176290035, R-Biopharm AG, Darmstadt, Germany; Beutler et al., in: Methods in Enzymatic Analysis (Bergmeyer, H. U. ed.) 3rd ed. 6:598-606, Verlag Chemie, Weinheim, Germany (1984).

Example 23

Production of Ethanol in a Cyanobacterial Culture

After the confirmation of the presence of the PDC and ADH genes in the transformed host cells, the cells can be scaled-up to large scale, long term, commercial production. The cells are scaled-up to a 100 ml scale, then to a 100 liter scale, then to a 500 liter outdoor cyanobacterial culture, using MBG-11 medium. The cultures grow for 3 months, with ethanol removed from the culture intermittently. Ethanol that can be used for biofuel is produced by use of this method.

Example 24

Plasmid Vector for Production in Cyanobacteria Comprising the Replication Factor from the ABICyano2-p2.5 Plasmid It is possible that an effective production plasmid for transformation to a cyanobacterial host cell can be constructed which contains only a portion of the initially characterized plasmid (SEQ ID NO: 1). For example, the gene encoding the replication factor, alone, without the surrounding upstream and downstream regions, or with shortened upstream and downstream regions, can be used to construct the plasmid. To determine whether this can be done, and whether the resulting plasmid is capable of being replicated when transformed to a host cyanobacterial cell, the following experiment was performed. Two types of constructs were prepared—one containing the full length original endogenous plasmid; the other containing a shortened version, having the replication protein. The results of the two constructs were examined.

I. Ethanologenic Shuttle Vector Construction and Transformation of *Cyanobacterium* sp. ABICyano1

Figure 17:
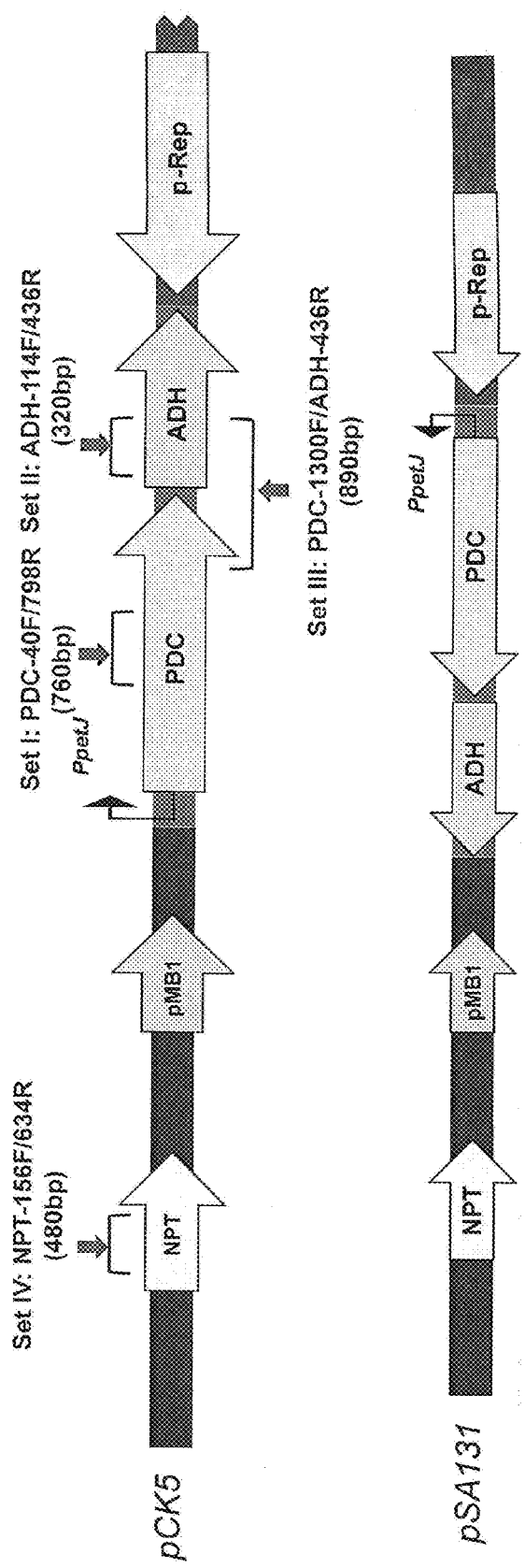
FIG. 17 is a schematic view of two ethanologenic shuttle vector constructs, one (pSA131) having the full length native plasmid sequence, and the other (pCK5) having the sequence of the gene region of the replication protein portion of the native plasmid, but not the remaining plasmid regions. Both plasmids were transformed to cyanobacterial host cells.

The ethanologenic gene cassette (PpetJ6803-PDCZm-ADH6803) was subcloned into parental RSF1010-based shuttle vectors pSA109 and pSA122, and the resulting ethanologenic shuttle vectors, named pSA131 (containing the full length native plasmid) and pCK5 (containing only the replication protein portion of the native plasmid) were made (FIG. 17). The constructs were transformed to the host cyanobacterial strain *Cyanobacterium* sp. ABICyano1. Putative transformants were selected on BG-11 agar plates containing 5 μg/ml of kanamycin (Km), and were further purified by re-streaks.

Figure 19:
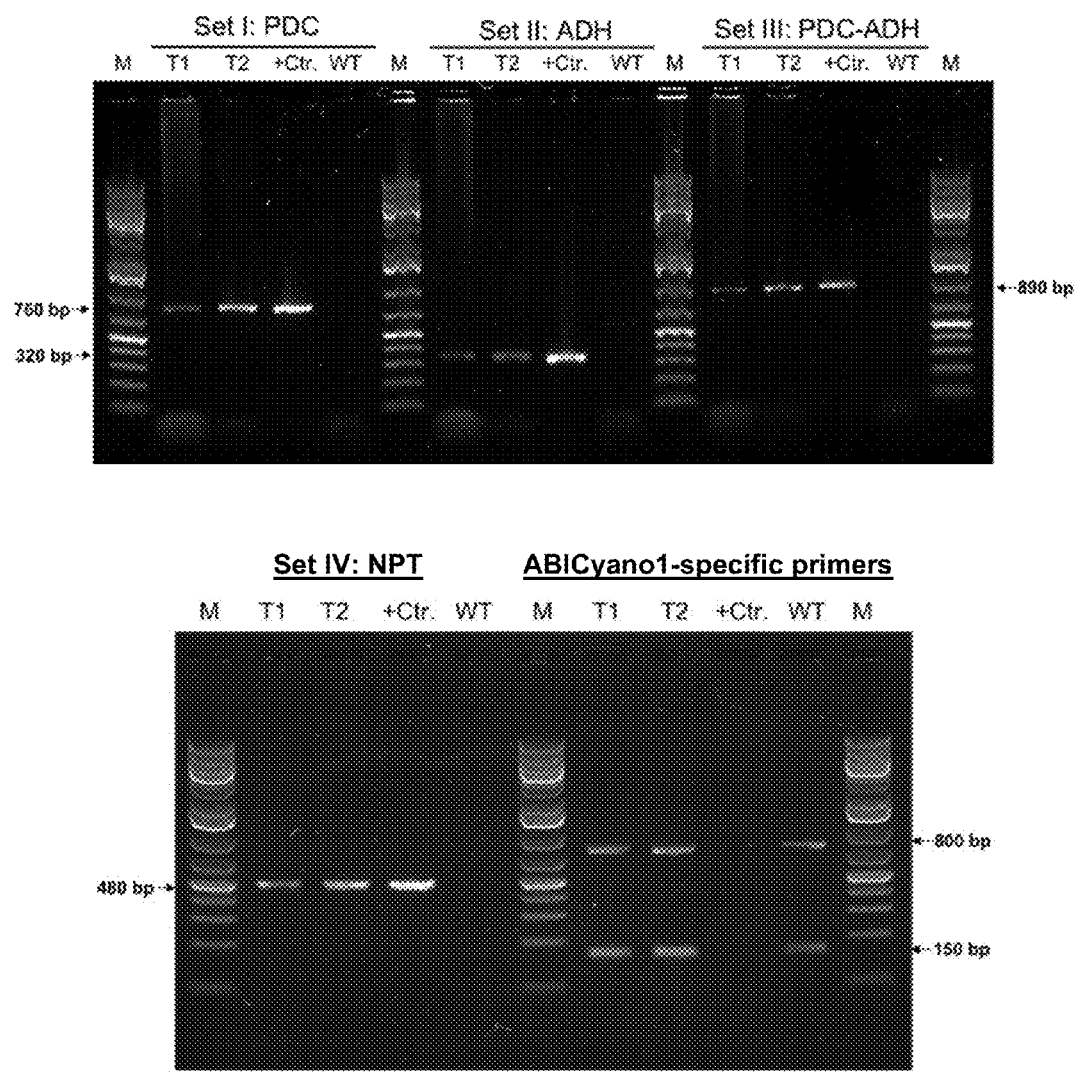
FIG. 19 is a photograph of the PCR confirmation of delivery of the shuttle vectors pSA131 and pCK5 to cyanobacterial host cells (*Cyanobacterium* sp. ABICyano1. The various PCR primer sets are specific to: region within PDC gene (760 bp), region within ADH gene (320 bp), region spanning the PDC-ADH genes (890 bp), the KmR NPT gene (480 bp), and the *Cyanobacterium* sp. ABICyano1 specific chromosomal gene M.AvaIII (150 bp) and native plasmid ABICyano1-p6.8 Rep gene (800 bp). The samples are labeled as: T1: ABICyano1::pSA131; T2: ABICyano1::pCK5; +Ctr.: pCK5; WT: wild-type *Cyanobacterium* sp. ABICyano1; M: DNA ladder.

The identity and purity of the putative transformants was first examined under microscopy (FIG. 18). The above selected transformant cultures were grown in liquid BG-11 medium containing 3 μg/ml of Km under constant light (60 μE m$^{-2}$ s$^{-1}$) at 37° C. with mixing at 120 rpm. The cells were then scaled up in selection medium broth for further PCR analyses (FIG. 19).

II. PCR Confirmation of the Delivery of Ethanologenic Shuttle Vectors into Cyanobacterial Host Cells PCR was used to confirm the delivery of the ethanologenic shuttle vectors into *Cyanobacterium* sp. ABICyano1 host cells, using the total DNA extracted from the putative transformants as templates. Using primers specific to the ethanologenic genes as indicated in FIG. 17 (Sets I-III: PDC and ADH) and the KmR gene (Set IV: NPT), expected PCR products were amplified from the putative transformants *Cyanobacterium* sp. ABICyano1::pSA131 and *Cyanobacterium* sp. ABICyano1::pCK5, but not from the wild-type cells. Additionally, using primers specific to *Cyanobacterium* sp. ABICyano1 genome (Set V), specific PCR amplicons were detected from both the transformants and wild-type cells, but not from the shuttle vector (as a plasmid positive control).

Although the present invention has been described in considerable detail with reference to certain embodiments thereof, other embodiments are possible. Therefore, the spirit and scope of the appended claims should not be limited to the description of the embodiments contained therein.

What is claimed is:

1. A nucleic acid construct for expressing a recombinant gene in a *cyanobacterium*, comprising:
    a. a DNA origin of replication for replication of the nucleic acid construct in cyanobacteria;
    b. a gene encoding a protein regulating replication of the nucleic acid construct in cyanobacteria by interacting with the DNA origin of replication, the protein comprising an amino acid sequence having at least 80% sequence identity to SEQ ID NO: 3; and
    c. at least one recombinant gene selected from (i) a production gene encoding a biocatalyst for the production of a chemical compound, (ii) a marker gene able to indicate the presence of the nucleic acid construct in the *cyanobacterium*, and combinations thereof, wherein said at least one recombinant gene is operably linked to at least one promoter.

2. The nucleic acid construct of claim 1, wherein the DNA origin of replication comprises a nucleotide sequence having at least 80% sequence identity to SEQ ID NO: 15.

3. The nucleic acid construct of claim 1, wherein said production gene is a biosynthetic pathway gene encoding an enzyme catalyzing a metabolic reaction which is not present in the wild-type *cyanobacterium* for the production of a chemical compound in the *cyanobacterium*.

4. The nucleic acid construct of claim 3, wherein the chemical compound is selected from the group consisting of: alcohols, alkanes, alkenes, ethers, polyhydroxyalkanoates such as PHB, fatty acids, fatty acid esters, hydrogen, and combinations thereof.

5. The nucleic acid construct of claim 4, wherein the alcohol is ethanol.

6. The nucleic acid construct of claim 1, wherein the production gene comprises at least one gene selected from the group consisting of: a gene encoding pyruvate decarboxylase enzyme (Pdc) converting pyruvate into acetaldehyde, a gene encoding alcohol dehydrogenase enzyme (Adh) converting acetaldehyde to ethanol, and a gene encoding alcohol dehydrogenase E enzyme (AdhE) converting Acetyl-CoA to ethanol, and combinations thereof.

7. The nucleic acid construct of claim 1, wherein the nucleic acid construct comprises a closed circular nucleic acid molecule.

8. The nucleic acid construct of claim 1, wherein the *cyanobacterium* is selected from the group consisting of: *Synechococcus* sp., *Synechocystis* sp., *Cyanobacterium* sp., and *Anabaena* sp.

9. The nucleic acid construct of claim 1, wherein the marker gene is a selectable marker.

10. The nucleic acid construct of claim 9, wherein selectable marker is an antibiotic resistance gene or a gene conferring prototrophy to an auxotrophic *cyanobacterium*.

11. The nucleic acid construct of claim 1, wherein the marker gene is a screenable marker.

12. The nucleic acid construct of claim 11, wherein the screenable marker is a gene encoding a fluorescent protein.

13. The nucleic acid construct of claim 1, further comprising a DNA origin of replication for replication of the nucleic acid construct in *Escherichia coli*.

14. The nucleic acid construct of claim 13, wherein said DNA origin of replication for replication in *E. coli* comprises SEQ ID NO: 10.

15. The nucleic acid construct of claim 1, further comprising a DNA origin for conjugational transfer (oriVT) of the nucleic acid construct from a bacterial host to the *cyanobacterium*.

16. The nucleic acid construct of claim 15, wherein the DNA origin of transfer (oriVT) sequence comprises SEQ ID NO: 81.

17. The nucleic acid construct of claim 1, further comprising a segment of DNA containing a plurality of restriction sites for restriction endonuclease enzymes, each of the plurality of restriction sites occurring only once within the nucleic acid construct, for inserting DNA into the nucleic acid construct.

18. The nucleic acid construct of claim 1, comprising a sequence having at least 50% identity to SEQ ID NO: 1.

19. The nucleic acid construct of claim 1, wherein the recombinant gene comprises altered codon triplets in comparison to a corresponding wild-type gene in order to enhance translation in the *cyanobacterium*.

20. The nucleic acid construct of claim 19, wherein the gene has a GC content of less than 42.5%.

21. The nucleic acid construct of claim 1, comprising a sequence having at least 70% identity to a sequence selected from the group consisting of SEQ ID NO: 82, SEQ ID NO: 83, SEQ ID NO: 84, and SEQ ID NO: 85.

22. A method of producing a metabolically enhanced cyanobacterial cell, comprising:
    a. obtaining the nucleic acid construct of claim 1;
    b. introducing the nucleic acid construct into the cyanobacterial cell; and
    c. recovering the transformed cyanobacterial cell.

23. A method for producing a chemical compound of interest with a cyanobacterial cell, comprising:
    a. introducing the nucleic acid construct of claim 1 into a cyanobacterial cell;
    b. culturing the cyanobacterial cell, the cell thereby producing the compound of interest; and
    c. obtaining the compound of interest from the culture.

24. A metabolically enhanced cyanobacterial cell for the expression of a recombinant gene, comprising:
    a. a plasmid comprising a DNA origin of replication with a nucleotide sequence having at least 80% sequence identity to SEQ ID NO: 15 and at least one recombinant gene selected from (i) a production gene encoding a biocatalyst for the production of a chemical compound, (ii) a marker gene able to indicate the presence of the nucleic acid construct in the *cyanobacterium*, and combinations thereof; and
    b. a gene encoding a protein regulating replication by interacting with said DNA origin of replication, the protein comprising an amino acid sequence having at least 80% sequence identity to SEQ ID NO: 3.

25. The metabolically enhanced cyanobacterial cell of claim 24, wherein at least one of said DNA origin of replication and said gene encoding a protein regulating replication is not endogenous to said cyanobacterial cell.

26. The metabolically enhanced cyanobacterial cell of claim 25, wherein said plasmid is a vector.

* * * * *